(12) United States Patent
Martin et al.

(10) Patent No.: US 8,114,681 B2
(45) Date of Patent: Feb. 14, 2012

(54) HIGHLY MULTIPLEXED PARTICLE-BASED ASSAYS

(75) Inventors: Jason Martin, Hartland, WI (US); Quan Ngoc Nguyen, San Ramon, CA (US)

(73) Assignee: Affymetrix, Inc., Santa Clara, CA (US)

( * ) Notice: Subject to any disclaimer, the term of this patent is extended or adjusted under 35 U.S.C. 154(b) by 359 days.

(21) Appl. No.: 12/287,062

(22) Filed: Oct. 2, 2008

(65) Prior Publication Data

US 2009/0131269 A1 May 21, 2009

Related U.S. Application Data

(60) Provisional application No. 60/997,949, filed on Oct. 5, 2007.

(51) Int. Cl.
*G01N 33/543* (2006.01)
*G01N 21/76* (2006.01)

(52) U.S. Cl. ............ 436/523; 435/6; 435/7.1; 435/7.94; 435/973; 435/287.2; 435/288.3; 435/288.4; 436/518; 436/524; 436/528; 436/172

(58) Field of Classification Search ............... 435/6, 7.1, 435/7.92, 7.94, 973, 287.2, 288.4, 288.3; 436/517, 518, 523, 524, 528, 172
See application file for complete search history.

(56) References Cited

U.S. PATENT DOCUMENTS

| | | | |
|---|---|---|---|
| 4,868,105 A | 9/1989 | Urdea et al. | |
| 5,093,232 A | 3/1992 | Urdea et al. | |
| 5,124,246 A | 6/1992 | Urdea et al. | |
| 5,635,352 A | 6/1997 | Urdea et al. | |
| 5,681,697 A | 10/1997 | Urdea et al. | |
| 5,681,702 A | 10/1997 | Collins et al. | |
| 5,712,383 A | 1/1998 | Sheridan et al. | |
| 5,747,244 A | 5/1998 | Sheridan et al. | |
| 5,780,227 A | 7/1998 | Sheridan et al. | |
| 5,849,481 A | 12/1998 | Urdea et al. | |
| 5,981,180 A | 11/1999 | Chandler et al. | |
| 6,232,462 B1 | 5/2001 | Collins et al. | |
| 6,235,465 B1 | 5/2001 | Kolberg et al. | |
| 6,449,562 B1 | 9/2002 | Chandler et al. | |
| 6,913,935 B1 * | 7/2005 | Thomas | 436/518 |

(Continued)

FOREIGN PATENT DOCUMENTS

WO    WO 2006/072033 A2    7/2006

(Continued)

OTHER PUBLICATIONS

Laher et al. (2006) "Development and evaluation of a rapid multianalyte particle-based flow cytometric assay for the quantification of meningococcal serogroup B-specific IgM antibodies in sera for nonculture case confirmation, " FEMS Immunol. Med. Microbiol., 48:34-43.

(Continued)

*Primary Examiner* — Gail R Gabel
(74) *Attorney, Agent, or Firm* — Quine Intellectual Property Law Group, P.C.; Monicia Elrod-Erickson

(57) ABSTRACT

Methods are provided for detecting and optionally quantitating multiple analytes, including nucleic acid and/or polypeptide analytes, in particle-based assays that can be highly multiplexed. Compositions, systems, and kits related to the methods are also featured.

11 Claims, 19 Drawing Sheets

U.S. PATENT DOCUMENTS

| | | | |
|---|---|---|---|
| 6,916,661 | B2 * | 7/2005 | Chandler et al. ............... 436/63 |
| 6,924,113 | B2 | 8/2005 | Li |
| 7,033,758 | B2 | 4/2006 | Kenny et al. |
| 7,803,541 | B2 | 9/2010 | Luo et al. |
| 2006/0263769 | A1 | 11/2006 | Luo et al. |
| 2006/0286583 | A1 | 12/2006 | Luo et al. |
| 2007/0015188 | A1 | 1/2007 | Luo et al. |
| 2007/0161015 | A1 | 7/2007 | Zheng et al. |
| 2007/0161020 | A1 | 7/2007 | Luo et al. |
| 2008/0050746 | A1 | 2/2008 | McMaster et al. |
| 2008/0176242 | A1 | 7/2008 | McMaster et al. |
| 2009/0298709 | A1 | 12/2009 | Ma |

FOREIGN PATENT DOCUMENTS

| | | |
|---|---|---|
| WO | WO 2006/105409 A2 | 10/2006 |
| WO | WO 2007/044427 A2 | 4/2007 |

OTHER PUBLICATIONS

Martens et al. (1999) "A generic particle-based nonradioactive homogeneous multiplex method for high-throughput screening using microvolume fluorimetry," Anal. Biochem., 273:20-31.

Vignali (2000) "Multiplexed particle-based flow cytometric assays," J. Immunol. Meth., 243:243-255.

Bender MedSystems, "Product Information and Manual, FlowCytomix Human Basic Kit," May 9, 2007, pp. 1-41.

Bushnell et al. (1999) "ProbeDesigner: for the design of probe sets for branched DNA (bDNA) signal amplification assays," Bioinformatics, 15:348-355.

Camilla et al. (2001) "Flow cytometric microsphere-based immunoassay: Analysis of secreted cytokines in whole-blood samples from asthmatics," Clinical and Diagnostic Laboratory Immunology, 8(4):776-784.

Carson and Vignali (1999) "Simultaneous quantitation of 15 cytokines using a multiplexed flow cytometric assay," J. Immunol. Meth., 227(1-2):41-52.

Collins et al. (1998) "Branched DNA (bDNA) technology for direct quantification of nucleic acids: Design and performance," in Gene Quantification, F Ferre, ed.

Csaki et al. (2002) "Gold nanoparticles as novel label for DNA diagnostics" Expert Rev. Mol. Diagn. 2:187-193.

Dubertret et al. (2002) In vivo imaging of quantum dots encapsulated in phospholipid micelles, Science, 298(5599):1759-1762.

Fitzgerald (2001) "Assays by the score," The Scientist 15(11):25.

Flagella et al. (2006) "A multiplex branched DNA assay for parallel quantitative gene expression profiling," Anal. Biochem., 352(1):50-60.

Forman-Kay and Pawson (1999) "Diversity in protein recognition by PTB domains" Curr. Opin. Struct. Biol., 9(6):690-695.

Fu et al. (2000) "14-3-3 Proteins: Structure, Function, and Regulation" Annual Review of Pharmacology and Toxicology 40(1):617-647.

Fulton et al. (1997) "Advanced multiplexed analysis with the FlowMetrix™ system," Clinical Chemistry, 43(9):1749-1756.

Geiss et al. (2008) "Direct multiplexed measurement of gene expression with color-coded probe pairs," Nature Biotechnology, 26:317-325.

Genospectra "QuantiGene® Plex Reagent System Instruction Manual," product literature, Oct. 14, 2004, pp. 1-26.

Gordon and McDade (1997) "Multiplexed quantification of human IgG, IgA, and IgM with the FlowMetrix™ system," Clinical Chemistry, 43(9):1799-1801.

Jaiswal et al. (2003) "Long-term multiple color imaging of live cells using quantum dot bioconjugates," Nature Biotechnology, 21(1):47-51.

Jones et al. (2002) "Multiplex assay for detection of strain-specific antibodies against the two variable regions of the G protein of respiratory syncytial virus," Clinical and Diagnostic Laboratory Immunology, 9(3):633-638.

Kellar and Iannone (2002) "Multiplexed microsphere-based flow cytometric assays" Experimental Hematology 30(11):1227-1237.

Kopf et al. (2005) "Panorama ab microarray cell signaling kit: a unique tool for protein expression analysis," Proteomics, 5(9):2412-2416.

Kuriyan and Cowburn (1997) "Modular peptide recognition domains in eukaryotic signaling," Annu. Rev. Biophys. Biomol. Struct. 26:259-288.

Martins (2002) "Development of internal controls for the Luminex instrument as part of a multiplexed seven-analyte viral respiratory antibody profile," Clinical and Diagnostic Laboratory Immunology, 9(1):41-45.

Nolte (1998) "Branched DNA signal amplification for direct quantitation of nucleic acid sequences in clinical specimens," *Advances in Clinical Chemistry*, 33(1):201-235.

Oliver et al. (1998) "Multiplexed analysis of human cytokines by use of the FlowMetrix system," Clinical Chemistry, 44(9):2057-2060.

Panomics, Inc., "Procarta Transcription Factor Assay Kit," user manual, 2006, iii-23.

Panomics, Inc., "Procarta™ SH2 Domain Plex," user manual, 2007, pp. iii-22.

Pawson et al. (2001) "SH2 domains, interaction modules and cellular wiring," Trends in Cell Biol. 11(12):504-511.

Reece et al. (2006) "Characterization of differential gene expression profiles in diabetic embryopathy using DNA microarray analysis," Am. J. Obstetrics & Gynecology, 195(4):1075-1080.

Sharma et al. (2002) "Protein-protein interactions: Lessons learned," Curr. Med. Chem.—Anti-Cancer Agents, 2(2):311-330.

Van Cleve et al. (1998) "Direct quantitation of HIV by flow cytometry using branched DNA signal amplification" Molecular and Cellular Probes 12:243-247.

Wang et al. (1997) "Regulation of insulin preRNA splicing by glucose" Proc Nat Acad Sci USA 94:4360-4365.

Wilber and Urdea (1998) "Quantification of HCV RNA in clinical specimens by branched DNA (bDNA) technology," Methods in Molecular Medicine: Hepatitis C, 19:71-78.

Wu et al. (2003) "Immunofluorescent labeling of cancer marker Her2 and other cellular targets with semiconductor quantum dots," Nature Biotechnology, 21(1):41-46.

Yang et al. (2001) "BADGE, Beads Array for the Detection of Gene Expression, a high-throughput diagnostic bioassay," Genome Res. 11:1888-1898.

Yang et al. (2006) "In silico and microarray-based genomic approaches to identifying potentional vaccine candidates against Leptospira interrogans," BMC Genomics, 7(1):293.

Yaoi et al. (2006) "Src Homology 2 Domain-based High Throughput Assays for Profiling Downstream Molecules in Receptor Tyrosine Kinase Pathways," Molecular & Cellular Proteomics 5.5, 959-968.

* cited by examiner

HIGHLY MULTIPLEXED PARTICLE-BASED ASSAYS

CROSS-REFERENCE TO RELATED APPLICATIONS

This application is a non-provisional utility patent application claiming priority to and benefit of the following prior provisional patent application: U.S. Ser. No. 60/997,949, filed Oct. 5, 2007, entitled "HIGHLY MULTIPLEXED PARTICLE-BASED ASSAYS" by Martin and Nguyen, which is incorporated herein by reference in its entirety for all purposes.

FIELD OF THE INVENTION

The present invention is in the field of analyte detection. The invention includes methods for detecting and optionally quantitating multiple analytes, including nucleic acid and/or polypeptide analytes, in assays that can be highly multiplexed. Compositions, systems, and kits related to the methods are also featured.

BACKGROUND OF THE INVENTION

A variety of assays have been developed in which proteins or nucleic acids are captured to particles and then detected, including multiplex assays in which multiple proteins or nucleic acids are captured from a single sample on different sets of distinguishable particles. See, e.g., Kellar and Iannone (2002) "Multiplexed microsphere-based flow cytometric assays" Experimental Hematology 30:1227-1237. The utility of such particle-based assays for high throughput applications has been limited, however, by such factors as the long read times required for typical instruments to process such assays and by the prohibitively high cost of reagents used to detect analytes captured on the particles.

The present invention overcomes the above-noted difficulties and facilitates rapid and inexpensive multiplexed particle-based assays, including highly multiplexed assays of analytes from different samples. A complete understanding of the invention will be obtained upon review of the following.

SUMMARY OF THE INVENTION

One aspect of the present invention provides methods for detecting and optionally quantitating multiple analytes in various assays, particularly particle-based assays. The assays can be highly multiplexed and can detect analytes from a number of samples simultaneously. Compositions, kits, and systems related to or useful in the methods are also described.

A first general class of embodiments provides methods of detecting analytes of interest. The methods include a) capturing a first analyte from a first sample on a first subset of particles (microspheres, microbeads, etc.), and separately capturing a second analyte from a second sample on a second subset of particles, wherein the particles of the second subset are distinguishable from those of the first subset; b) after step a), combining the first and second subsets of particles; and c) after step b), identifying at least a portion of the particles from each subset and determining whether those particles have analytes captured thereto. As noted above, the initial step of the assay—capturing the analytes to identifiable, distinguishable subsets of particles—is performed separately for the different samples, e.g., in different tubes or different wells. The particles are combined (e.g., into a single tube or well) for the final read step, and are optionally combined for any processing required to detect the analytes before the read step (e.g., they can be combined prior to addition of a detection reagent).

The methods can be further multiplexed, for example, by using third, fourth, etc. distinguishable subsets of particles to capture third, fourth, etc. analytes from third, fourth, etc. samples and/or by using two or more distinguishable subsets of particles to capture two or more analytes from one or more of the samples. Additional variations on the methods can be employed, as described for the embodiments below.

Another general class of embodiments also provides methods of detecting analytes of interest. In this class of embodiments, a first sample comprising or putatively comprising a first group of one or more analytes and a second sample comprising or putatively comprising a second group of one or more analytes are provided. A first and a second population of particles (microspheres, microbeads, etc.) are also provided.

The first population of particles includes one or more subsets of particles. In embodiments in which the population comprises two or more subsets, a plurality of the particles in each subset are distinguishable from a plurality of the particles in the other subsets. The particles in each subset comprise a capture molecule configured to capture one of the analytes of the first group. In embodiments in which the first population comprises two or more subsets of particles, the capture molecule on each subset is different from those on the other subsets of the first population; each subset of particles can thus capture a different, predetermined analyte.

Similarly, the second population of particles also includes one or more subsets of particles. A plurality of the particles in each subset of the second population are distinguishable from a plurality of the particles in the subsets of the first population. In addition, in embodiments in which the second population comprises two or more subsets, a plurality of the particles in each subset of the second population are distinguishable from a plurality of the particles in the other subsets of the second population. The particles in each subset of the second population comprise a capture molecule configured to capture one of the analytes of the second group. In embodiments in which the second population comprises two or more subsets of particles, the capture molecule on each subset of the second population is different from those on the other subsets of the second population.

The first sample and the first population of particles are contacted with each other, and any analyte of the first group present in the first sample is captured on a selected subset of the first population of particles (i.e., the subset comprising the capture molecule configured to capture that analyte). The second sample and the second population of particles are contacted, and any analyte of the second group present in the second sample is captured on a selected subset of the second population of particles (i.e., the subset comprising the capture molecule configured to capture that analyte). The two populations are separately contacted with their corresponding samples, e.g., in separate containers (tubes, wells, etc.) and/or in separate operations.

The first and second populations of particles, along with any captured analytes, are then combined. Which subsets of particles have an analyte of interest captured thereon is then detected. Since a correlation exists between a particular subset of particles and a particular analyte from a particular sample, which subsets of particles bear captured analytes indicates which analytes were present in the first and second samples.

The methods are useful for multiplex detection of analytes, optionally highly multiplex detection. Thus, the first group of analytes to be detected from the first sample optionally comprises two or more, three or more, five or more, 10 or more, 20 or more, 30 or more, 40 or more, 50 or more, or even 100 or more analytes, and a like number of distinguishable subsets of particles are provided in the first population. Similarly, the second group of analytes to be detected from the second sample optionally comprises two or more, three or more, five or more, 10 or more, 20 or more, 30 or more, 40 or more, 50 or more, or even 100 or more analytes, and a like number of distinguishable subsets of particles are provided in the second population. Similarly, the methods optionally include providing a third (fourth, fifth, etc.) sample comprising or suspected of comprising a third (fourth, fifth, etc.) group of one (two, three, four, etc.) or more analytes, and providing a third (fourth, fifth, etc.) population comprising one (two, three, four, etc.) or more subsets of particles distinguishable from each other and from those of the other populations and comprising capture molecules configured to capture the analytes of the third (fourth, fifth, etc.) group. The additional samples and particle populations are contacted separately, and then combined with the first and second populations prior to detection as described above. It will be evident that the number of particle populations, subsets of particles in each population, etc. can be varied as desired for the particular application of interest.

The capture molecule for a particular analyte can be essentially any molecule (or complex comprising a molecule) that can be configured to capture the analyte, e.g., any molecule that binds specifically to the analyte or that indirectly captures the analyte. For example, a capture molecule can comprise a polynucleotide (e.g., a polynucleotide capture probe, a nucleic acid binding site for a transcription factor, or an aptamer), a polypeptide (e.g., an antibody, a recombinant protein, an SH2 or PTB domain for capturing a tyrosine-phosphorylated polypeptide, an SH3 domain for capturing a proline rich polypeptide, a 14-3-3 domain for capturing a serine-phosphorylated polypeptide, a chromodomain for capturing a lysine-methylated polypeptide, a bromodomain for capturing a lysine-acetylated polypeptide, or a synthetic peptide), a substrate analog and/or a small molecule. The capture molecules can be configured to capture their respective analytes directly or indirectly. Thus, in one aspect, the analytes bind directly to the capture molecules. In another aspect, the analytes bind directly to molecules which are in turn bound directly to the capture molecules. Similarly, the analytes can bind to molecules which are bound via other molecules to the capture molecules.

As noted, the subsets of the first population comprise different capture molecules from each other, and the subsets of the second population likewise comprise different capture molecules from other subsets of the second population. In some embodiments, subsets of the first and second populations comprise different capture molecules from each other as well, e.g., in embodiments in which the capture molecules bind directly to the analytes and the analytes of the first and second groups are different. In other embodiments, there is overlap between the capture molecules on one or more subsets of the first and second populations. Thus, in one class of embodiments, the capture molecule on a subset of the particles of the second population is substantially identical to the capture molecule on a subset of the first population. Optionally, the capture molecules on each of the two or more subsets of the particles in the second population are substantially identical to the capture molecules on subsets of the first population. This configuration can be employed, for example, when the capture molecules bind directly to the analytes and the analytes of the first and second groups are the same, or when the capture molecules capture the analytes indirectly, as described in greater detail below.

The analytes can be essentially any molecules, complexes, etc. whose detection and/or quantitation is desired. Exemplary analytes include, but are not limited to, polypeptides (e.g., specific polypeptides, nucleic acid binding proteins, specific posttranslationally modified forms of specific polypeptides, such as phosphorylated, glycosylated, acetylated, ubiquitinated, sumoylated, hydroxylated, or methylated forms, antibodies, etc.), nucleic acids (e.g., DNAs, RNAs, mRNAs, ribosomal RNAs, microRNAs, transcription factor binding sites, and genomic DNAs or RNAs), drugs, compounds, chemicals, and small molecules.

The methods are optionally employed to compare the presence (or amount) of analytes between samples from different sources. Thus, in one class of embodiments, the analytes of the first group and the analytes of the second group represent the same group of target molecules derived from different sources. In other embodiments, the analytes of the first group and the analytes of the second group are different target molecules.

Analytes captured on the particles are optionally detected by associating a label with the analytes. In some embodiments, each analyte comprises a label or has a label associated with it before the analytes are captured on the particles, while in other embodiments, the label is associated with the analytes after capture but before the particle populations are combined. In such embodiments, detecting which subsets of particles have an analyte captured thereon comprises identifying at least a portion of the particles from each subset and detecting the presence or absence of the label on those particles. For many applications, however, associating the label with the analytes after their capture on the particles and after combination of the particle populations is more convenient, requires fewer manipulations, and results in consumption of fewer reagents. Thus, in one aspect, detecting which subsets of particles have an analyte of interest captured on the particles involves, after combination of the particle populations, associating a label with any of the analytes captured on the particles, identifying at least a portion of the particles from each subset, and detecting the presence or absence of the label on those particles. Typically, the label is provided as part of a detection reagent (e.g., a molecule or complex) that binds, directly or indirectly through other molecules, to one or more of the analytes. Thus, in one class of embodiments, a detection reagent comprising the label is provided and contacted with the combined populations of particles, whereby the detection reagent binds directly or indirectly to any analyte captured on the particles, thereby associating the label with any analyte captured on the particles. Exemplary detection reagents include, but are not limited to, labeled antibodies, labeled polynucleotides, and labeled biotin-binding moieties such as avidin or streptavidin.

The methods can be qualitative or quantitative. For example, fluorescent signal from a detection reagent comprising a fluorescent label can be detected to indicate the presence or absence of the detection reagent and therefore of the corresponding analyte(s), or the fluorescent signal can be quantitated to quantitate the analyte(s). Thus, in one class of embodiments, an intensity of the signal from the label is measured, and the intensity of the signal for a given subset of particles is correlated with a quantity of the corresponding analyte of interest present.

A number of exemplary assays can be adapted to the practice of the present invention. In one exemplary class of embodiments, the analytes are nucleic acids; the capture molecules are polynucleotide capture probes; capturing any analytes of the first group present in the first sample on a selected subset of the particles in the first population comprises i) providing one or more subsets of two or more capture extenders, wherein each subset of capture extenders is configured to hybridize to one of the nucleic acid analytes of the first group, and wherein the capture extenders in each subset are configured to hybridize to one of the capture probes on the particles of the first population, and ii) hybridizing any nucleic acid analyte of the first group present in the first sample to its corresponding subset of capture extenders and hybridizing the subset of capture extenders to its corresponding capture probe, whereby the nucleic acid analyte is captured on the selected subset of particles comprising that capture probe; capturing any analytes of the second group present in the second sample on a selected subset of the particles in the second population comprises i) providing one or more subsets of two or more capture extenders, wherein each subset of capture extenders is configured to hybridize to one of the nucleic acid analytes of the second group, and wherein the capture extenders in each subset are configured to hybridize to one of the capture probes on the particles of the second population, and ii) hybridizing any nucleic acid analyte of the second group present in the second sample to its corresponding subset of capture extenders and hybridizing the subset of capture extenders to its corresponding capture probe, whereby the nucleic acid analyte is captured on the selected subset of particles comprising that capture probe; and detecting which subsets of particles have an analyte of interest captured on the particles comprises i) associating a label with any analyte captured on the particles by hybridizing one or more label extenders and a label probe system comprising the label to any nucleic acid analyte captured on the particles, ii) identifying at least a portion of the particles from each subset, and iii) detecting the presence or absence of the label on those particles.

In another exemplary class of embodiments, the analytes are biotinylated nucleic acids, and the capture molecules are polynucleotides, each of which is complementary to one of the nucleic acid analytes. The first sample is provided by isolating a first group of one or more biotinylated nucleic acids bound by one or more transcription factors, and the second sample is similarly provided by isolating a second group of one or more biotinylated nucleic acids bound by one or more transcription factors. Analytes of the first or second group present in the first or second sample are captured on a selected subset of the first or second population of particles by hybridizing any biotinylated nucleic acid analyte present in the first or second sample to its complementary polynucleotide capture molecule, and which subsets of particles have an analyte of interest captured on the particles is detected by binding labeled streptavidin or labeled avidin to the biotinylated nucleic acid analytes, identifying at least a portion of the particles from each subset, and detecting the presence or absence of the label on those particles.

In yet another exemplary class of embodiments, the analytes are tyrosine-phosphorylated polypeptides, and the capture molecules comprise SH2 domains. Which subsets of particles have an analyte of interest captured on the particles can be detected by, for example, i) binding a biotinylated anti-phosphotyrosine antibody to any tyrosine-phosphorylated polypeptide analyte captured on the particles, and binding labeled streptavidin or labeled avidin to the biotinylated anti-phosphotyrosine antibody, ii) identifying at least a portion of the particles from each subset, and iii) detecting the presence or absence of the label on those particles.

The particles are optionally washed at any of various steps to remove unbound material from the particles, e.g., with a solution comprising a buffer, salt, detergent, blocking agent, and/or the like. For example, the particles can be washed after capture of the analytes (e.g., before or after combination of the particle populations) but before the detection step.

A variety of suitable particles are known in the art, and many are commercially available. In one class of embodiments, the particles are microspheres, and the microspheres of each subset are distinguishable from those of the other subsets on the basis of their fluorescent emission spectra, their diameter, or a combination thereof. Additional exemplary suitable particles are described herein.

Essentially any assay based on binding of analytes to distinguishable moieties can be multiplexed or further multiplexed using the methods of the present invention, whether the moieties are particles such as those described herein or another type of distinguishable assay component. Accordingly, another general class of embodiments provides methods of detecting analytes of interest. In the methods, a first sample comprising or putatively comprising a first group of one or more analytes and a second sample comprising or putatively comprising a second group of one or more analytes are provided. A first and second set of reporter entities are also provided. (Additional samples and sets of reporter entities are optionally also provided.)

The first set includes one or more reporter entities, each of which is configured to capture a different analyte of the first group. In embodiments in which the first set comprises two or more reporter entities, the reporter entities of the first set are distinguishable from each other. Similarly, the second set includes one or more reporter entities, each of which is configured to capture a different analyte of the second group. In embodiments in which the second set comprises two or more reporter entities, the reporter entities of the second set are distinguishable from each other. Each of the reporter entities of the second set is distinguishable from the reporter entities of the first set.

The first sample and the first set of reporter entities are contacted with each other, and any analyte of the first group present in the first sample is captured to a selected reporter entity of the first set (i.e., the entity configured to capture that analyte). The second sample and the second set of reporter entities are contacted with each other, and any analyte of the second group present in the first sample is captured to a selected reporter entity of the second set (i.e., the entity configured to capture that analyte). The two sets are separately contacted with their corresponding samples, e.g., in separate containers (tubes, wells, etc.) and/or in separate operations.

The first and second sets of reporter entities, along with any captured analytes, are then combined. Which reporter entities have an analyte of interest captured thereon is then detected. Since a correlation exists between a particular reporter entity and a particular analyte from a particular sample, which reporter entities bear captured analytes indicates which analytes were present in the first and second samples.

Essentially all of the features noted for the methods above apply to these embodiments as well, as relevant; for example, with respect to number of analytes per group, groups of analytes, sets of reporter entities, and/or reporter entities per set, type of analytes, source of the samples, inclusion of detection reagent, and/or the like. As for the embodiments above, the analytes of the first and second groups can be the same target molecules from different sources or they can be different target molecules; accordingly, the reporter entities of the first and second sets can be configured to capture the same or different analytes.

As noted, compositions related to, produced by, or of use in the methods are another feature of the invention. For example, one general class of embodiments provides a composition that includes a mixture of at least a first population of particles and a second population of particles. The first population of particles includes one or more subsets of particles. In embodiments in which the population comprises two or more subsets, a plurality of the particles in each subset are distinguishable from a plurality of the particles in the other subsets. The particles in each subset comprise a capture molecule. In embodiments in which the first population comprises two or more subsets of particles, the capture molecule on each subset is different from those on the other subsets of the first population; each subset of particles can thus capture a different, predetermined analyte. Similarly, the second population of particles also includes one or more subsets of particles. A plurality of the particles in each subset of the second population are distinguishable from a plurality of the particles in the subsets of the first population. In addition, in embodiments in which the second population comprises two or more subsets, a plurality of the particles in each subset of the second population are distinguishable from a plurality of the particles in the other subsets of the second population. The particles in each subset of the second population comprise a capture molecule. In embodiments in which the second population comprises two or more subsets of particles, the capture molecule on each subset of the second population is different from those on the other subsets of the second population.

As noted, the subsets of the first population comprise different capture molecules from each other, and the subsets of the second population likewise comprise different capture molecules from other subsets of the second population. In some embodiments, subsets of the first and second populations comprise different capture molecules from each other as well. In other embodiments, however, there is overlap between the capture molecules on one or more subsets of the first and second populations. Thus, in one class of embodiments, the capture molecule on a subset of the particles of the second population is substantially identical to the capture molecule on a subset of the first population. Optionally, the capture molecules on each of the two or more subsets of the particles in the second population are substantially identical to the capture molecules on subsets of the first population.

Optionally, analytes originating from a first sample are captured on (i.e., directly or indirectly bound to) the particles of the first population (e.g., one analyte per particle subset) while analytes originating from a second sample are captured on the particles of the second population. Essentially all of the features noted for the methods above apply to these embodiments as well, as relevant; for example, with respect to number of analytes, groups of analytes, subsets of particles per population, and/or particle populations, type of analytes, source of the samples, type of capture molecules, inclusion of detection reagent, and/or the like.

A related general class of embodiments provides a composition that includes a first group of one or more analytes, which analytes originate from a first sample, a second group of one or more analytes, which analytes originate from a second sample different from the first sample, and a mixture of at least a first population of particles and a second population of particles. The first population of particles includes one or more subsets of particles. In embodiments in which the population comprises two or more subsets, a plurality of the particles in each subset are distinguishable from a plurality of the particles in the other subsets. The particles in each subset comprise a capture molecule, which capture molecule is configured to capture one of the analytes of the first group. In embodiments in which the first population comprises two or more subsets of particles, the capture molecule on each subset is different from those on the other subsets of the first population; each subset of particles can thus capture a different, predetermined analyte. Similarly, the second population of particles also includes one or more subsets of particles. A plurality of the particles in each subset of the second population are distinguishable from a plurality of the particles in the subsets of the first population. In addition, in embodiments in which the second population comprises two or more subsets, a plurality of the particles in each subset of the second population are distinguishable from a plurality of the particles in the other subsets of the second population. The particles in each subset of the second population comprise a capture molecule, which capture molecule is configured to capture one of the analytes of the second group. In embodiments in which the second population comprises two or more subsets of particles, the capture molecule on each subset of the second population is different from those on the other subsets of the second population. Generally, the analytes of the first group are captured on the particles of the first population while the analytes of the second group are captured on the particles of the second population.

Essentially all of the features noted for the methods above apply to the composition embodiments as well, as relevant; for example, with respect to number of analytes, groups of analytes, subsets of particles per population, and/or particle populations, type of analytes, source of the samples, type of capture molecules, inclusion of detection reagent, and/or the like. Thus, for example, the composition optionally includes three or more, five or more, 10 or more, 20 or more, 30 or more, 40 or more, 50 or more, or even 100 or more populations of particles, and each population optionally includes two or more, three or more, five or more, 10 or more, 20 or more, 30 or more, 40 or more, 50 or more, or even 100 or more distinguishable subsets of particles.

Another general class of embodiments provides a composition comprising a first group of one or more analytes, which analytes originate from a first sample, a second group of one or more analytes, which analytes originate from a second sample different from the first sample, and a mixture of at least a first set of reporter entities and a second set of reporter entities. The first set of reporter entities includes one or more reporter entities, each of which is configured to capture a different one of the analytes of the first group. In embodiments in which the first set comprises two or more reporter entities, the reporter entities are distinguishable from each other. Similarly, the second set of reporter entities also comprises one or more reporter entities, each of which is configured to capture a different one of the analytes of the second group. The reporter entities of the second set are distinguishable from those of the first set. In embodiments in which the second set comprises two or more reporter entities, the reporter entities of the second set are distinguishable from each other. Generally, the analytes of the first group are captured to the reporter entities of the first set, while the analytes of the second group are captured to the reporter entities of the second set.

Essentially all of the features noted for the embodiments above apply to these embodiments as well, as relevant; for example, with respect to number of analytes per group, groups of analytes, sets of reporter entities, and/or reporter entities per set, type of analytes and/or reporter entities, source of the samples, inclusion of detection reagent, and/or the like. As for the embodiments above, the analytes of the first and second groups can be the same target molecules from different sources or they can be different target molecules; accordingly, the reporter entities of the first and second sets can be configured to capture the same or different analytes.

Figure 1:
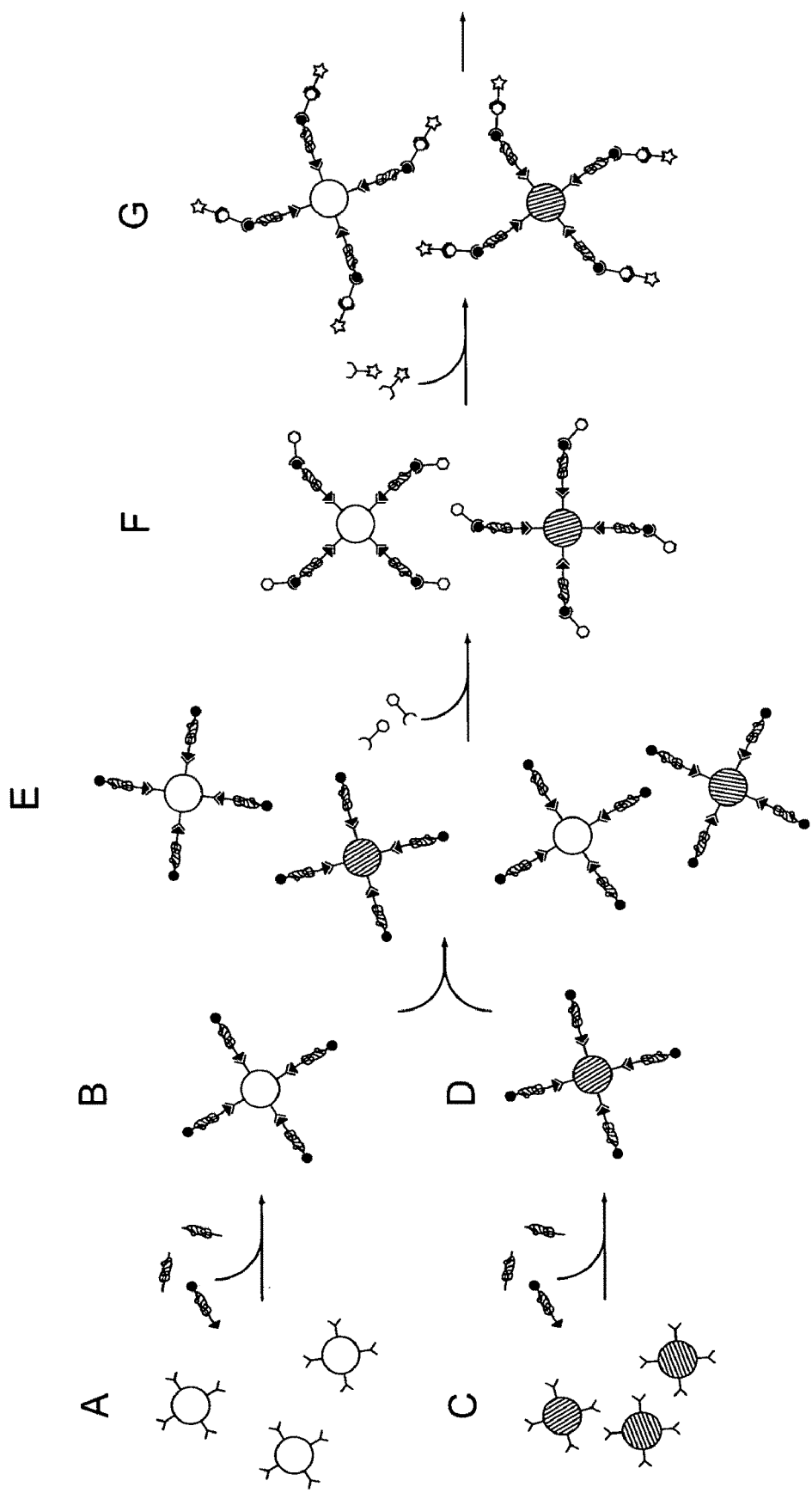
FIG. 1 Panels A-H schematically illustrate a multiplex immunoassay in which different populations of particles include the same capture molecule and are used to capture the same analyte from different samples.
Figure 1:
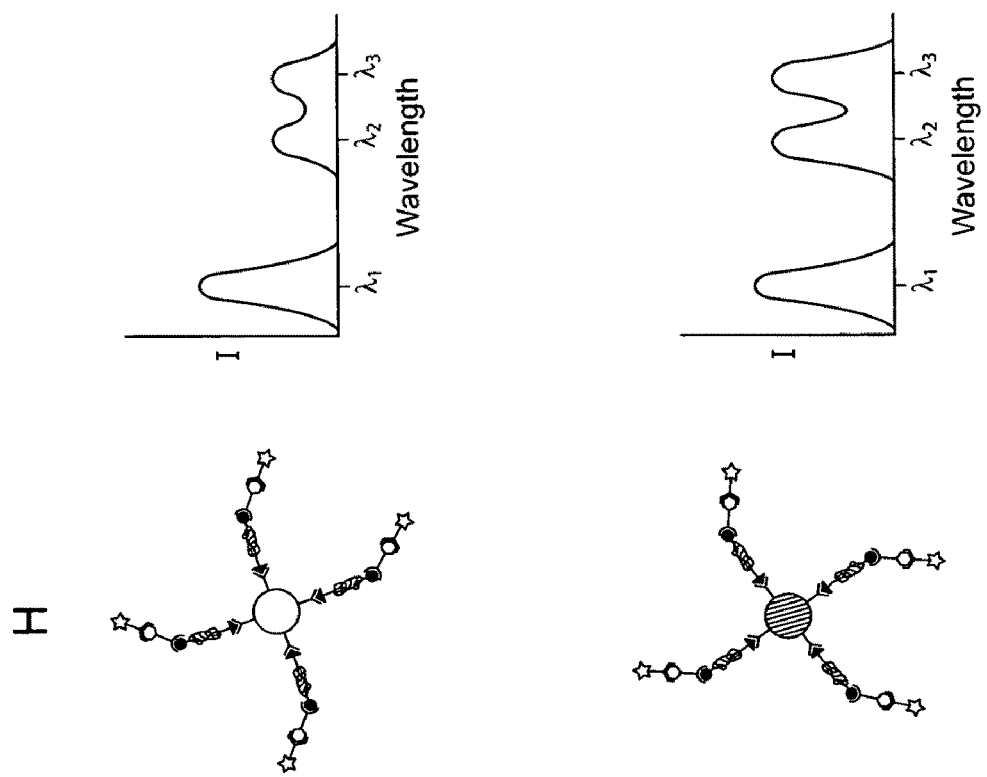

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

An "analyte" is a molecule or complex that is to be detected and/or quantitated. Exemplary analytes include, but are not limited to, polypeptides (e.g., proteins, phosphorylated or other posttranslationally modified forms of a protein, antibodies, etc.) and nucleic acids (e.g., DNAs, RNAs, mRNAs, ribosomal RNAs, microRNAs, transcription factor binding sites, genomic DNAs or RNAs, etc.).

A "capture molecule" is a molecule that is configured to capture a particular analyte of interest (whether through direct or indirect binding to the analyte) and that is tightly bound (e.g., covalently or noncovalently, directly or through a linker, e.g., streptavidin-biotin or the like) to a solid support such as a particle (e.g., a microsphere, microbead, or the like). In some aspects, the capture molecule binds directly to the analyte and is specific for that analyte. In other aspects, the capture molecule binds to one or more molecules that bind in turn to the analyte to specifically capture it. Exemplary capture molecules include, but are not limited to, polypeptides (e.g., antibodies, SH2 and other polypeptide binding domains, short synthetic peptides, and antigens), polynucleotides (e.g., polynucleotide capture probes, transcription factor binding sites, aptamers), antigens, polysaccharides, lipids, and small molecules.

A capture molecule "specific for" an analyte in a mixture of analytes has a higher affinity for that analyte than for any other analyte in the mixture. Typically, the capture molecule binds the analyte for which it is specific at least about 10 times more tightly (and preferably at least about 100 times more tightly, at least about 1000 times more tightly, or even at least about 10,000 times more tightly) than any other analyte in the mixture, e.g., under typical assay conditions. Examples include, but are not limited to, an antibody capture molecule specific for a polypeptide analyte (i.e., an antibody having a higher affinity for that polypeptide than for any other polypeptides in the mixture) or a polynucleotide capture molecule complementary to a nucleic acid analyte. Specificity of the capture molecule for another molecule which is in turn specific for the analyte is analogously defined.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or nucleotide analogs, can be natural or non-natural (e.g., Locked NucleicAcid™, isoG, or isoC nucleotides), and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology—Hybridization with Nucleic Acid Probes, part I chapter 2, "Overview of principles of hybridization and the strategy of nucleic acid probe assays" (Elsevier, New York), as well as in Ausubel, infra.

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "capture extender" or "CE" is a polynucleotide that is capable of hybridizing to a nucleic acid analyte of interest and to a capture probe. The capture extender typically has a first polynucleotide sequence C-1, which is complementary to the capture probe, and a second polynucleotide sequence C-3, which is complementary to a polynucleotide sequence of the nucleic acid analyte of interest. Sequences C-1 and C-3 are typically not complementary to each other. The capture extender is preferably single-stranded.

A "capture probe" or "CP" is a polynucleotide that is capable of hybridizing to at least one capture extender and that is tightly bound (e.g., covalently or noncovalently, directly or through a linker, e.g., streptavidin-biotin or the like) to a solid support (a particle such as a microsphere or the like). The capture probe typically comprises at least one polynucleotide sequence C-2 that is complementary to polynucleotide sequence C-1 of at least one capture extender. The capture probe is preferably single-stranded.

A "label extender" or "LE" is a polynucleotide that is capable of hybridizing to a nucleic acid analyte of interest and to a label probe system. The label extender typically has a first polynucleotide sequence L-1, which is complementary to a polynucleotide sequence of the nucleic acid analyte of interest, and a second polynucleotide sequence L-2, which is complementary to a polynucleotide sequence of the label probe system (e.g., L-2 can be complementary to a polynucleotide sequence of an amplification multimer, a preamplifier, a label probe, or the like). The label extender is preferably single-stranded.

A "label" is a moiety that facilitates detection of a molecule. Common labels in the context of the present invention include fluorescent, luminescent, light-scattering, and/or calorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "label probe system" comprises one or more polynucleotides that collectively comprise a label and a polynucleotide sequence M-1, which is capable of hybridizing to at least one label extender. The label provides a signal, directly or indirectly. Polynucleotide sequence M-1 is typically complementary to sequence L-2 in the label extenders. The label probe system can include a plurality of label probes (e.g., a plurality of identical label probes) and an amplification multimer; it optionally also includes a preamplifier or the like, or optionally includes only label probes, for example.

An "amplification multimer" is a polynucleotide comprising a plurality of polynucleotide sequences M-2, typically (but not necessarily) identical polynucleotide sequences M-2. Polynucleotide sequence M-2 is complementary to a polynucleotide sequence in the label probe. The amplification multimer also includes at least one polynucleotide sequence that is capable of hybridizing to a label extender or to a nucleic acid that hybridizes to the label extender, e.g., a preamplifier. For example, the amplification multimer optionally includes at least one polynucleotide sequence M-1; polynucleotide sequence M-1 is typically complementary to polynucleotide sequence L-2 of the label extenders. Similarly, the amplification multimer optionally includes at least one polynucleotide sequence that is complementary to a polynucleotide sequence in a preamplifier (which in turn includes at least one polynucleotide sequence M-1 complementary to polynucleotide sequence L-2 of the label extenders). The amplification multimer can be, e.g., a linear or a branched nucleic acid. As noted for all polynucleotides, the amplification multimer can include modified nucleotides and/or nonstandard internucleotide linkages as well as standard deoxyribonucleotides, ribonucleotides, and/or phosphodiester bonds. Suitable amplification multimers are described, for example, in U.S. Pat. No. 5,635,352, U.S. Pat. No. 5,124,246, U.S. Pat. No. 5,710,264, and U.S. Pat. No. 5,849,481.

A "label probe" or "LP" is a single-stranded polynucleotide that comprises a label (or optionally that is configured to bind to a label) that directly or indirectly provides a detectable signal. The label probe typically comprises a polynucleotide sequence that is complementary to the repeating polynucleotide sequence M-2 of the amplification multimer; however, if no amplification multimer is used in the bDNA assay, the label probe can, e.g., hybridize directly to a label extender.

A "preamplifier" is a nucleic acid that serves as an intermediate between at least one label extender and amplification multimer. Typically, the preamplifier is capable of hybridizing simultaneously to at least one label extender and to a plurality of amplification multimers. The preamplifier can be, e.g., a linear or a branched nucleic acid.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1999), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies, for example. Antibodies include multiple or single chain antibodies, including single chain Fv (sFv or scFv) antibodies in which a variable heavy and a variable light chain are joined together (directly or through a peptide linker) to form a continuous polypeptide, and humanized or chimeric antibodies. Antibodies include polyclonal and monoclonal antibodies.

A "posttranslational modification" of a protein is a transformation (generally an enzymatic transformation) that occurs following translation of some or all of the protein's amino acid residues. Typically, posttranslational modification involves attachment of a small chemical group (or groups) to a functional group of certain amino acid residues (e.g., the epsilon amino group of lysine or the hydroxyl group of serine, threonine, or tyrosine) or to the protein's terminal amino or carboxyl group. Examples include, but are not limited to, phosphorylation, glycosylation, acetylation, lipidation (e.g., prenylation, farnesylation, myristoylation, attachment of a fatty acid or a GPI anchor), ubiquitination, sumoylation, hydroxylation, methylation and nucleotidylation (e.g., ADP-ribosylation).

A "microsphere" is a small spherical, or roughly spherical, particle. A microsphere optionally has a diameter less than about 1000 micrometers (e.g., less than about 100 micrometers, optionally less than about 10 micrometers). The microsphere can comprise any of a variety of materials (e.g., silica, polystyrene or another polymer) and can optionally have various surface chemistries (e.g., free carboxylic acid, amine, or hydrazide groups, among many others).

A "microorganism" is an organism of microscopic or submicroscopic size. Examples include, but are not limited to, bacteria, fungi, yeast, protozoans, microscopic algae (e.g., unicellular algae), viruses (which are typically included in this category although they are incapable of growth and reproduction outside of host cells), subviral agents, viroids, and mycoplasma.

An "aptamer" is a nucleic acid capable of interacting with a ligand. An aptamer can be, e.g., a DNA or RNA, and can be e.g. a chemically synthesized oligonucleotide. The ligand can be any natural or synthetic molecule.

A variety of additional terms are defined or otherwise characterized herein.

DETAILED DESCRIPTION

One aspect of the present invention provides methods for detecting and optionally quantitating multiple analytes in particle-based assays. The assays can be highly multiplexed, and can detect analytes from a number of samples simultaneously. Compositions, kits, and systems related to or useful in the methods are also described.

Particle-Based Assays

In general, in a conventional multiplex particle-based assay, a mixture of multiple sets of distinguishable particles is added to a sample. Typically, the particles of each set have a fluorescent emission spectrum that is different from the emission spectra of the other particle sets. Each different set of particles is pre-coated with a reagent that is specific for a different analyte of interest, and thus different analytes are captured from the sample to different sets of particles. The analytes are then labeled, generally through addition of one or more fluorescently labeled reagents that bind to the analytes. The fluorescent label used has an emission different from any fluorescent emissions by the particles. The assay is read in a flow cytometer or similar instrument: each particle is identified as a member of a particular set, e.g., on the basis of its fluorescent emission spectrum, and whether that particle has analyte captured on it is determined, e.g., by detecting the presence or absence of fluorescent label on the particle. Since the relationship between a particular particle set and a particular analyte is predetermined by the choice of capture reagent used to coat those particles, the presence of fluorescent label on a given particle is indicative of the presence of a given analyte in the original sample even when a single fluorescent label is used to label all the analytes. See, e.g., U.S. Pat. No. 5,981,180 entitled "Multiplexed analysis of clinical specimens apparatus and methods" to Chandler et al., U.S. Pat. No. 6,449,562 entitled "Multiplexed analysis of clinical specimens apparatus and methods" to Chandler et al., Kellar and Iannone (2002) "Multiplexed microsphere-based flow cytometric assays" Experimental Hematology 30:1227-1237, Fitzgerald (2001) "Assays by the score" The Scientist 15 [11]:25, and Fulton et al. (1997) "Advanced multiplexed analysis with the FlowMetrix™ system" Clinical Chemistry 43:1749-1756.

In such conventional particle-based assays, when analytes from different samples are to be detected and compared, particles are contacted with each sample, processed, and read separately. In the methods of the present invention, however, different populations of particles are contacted with each sample separately, optionally combined before or during processing steps for detection of the analyte, and then read together. Analytes from different samples can thus be detected simultaneously, with concomitant savings in both processing and read times and reagent costs. The increased speed and decreased costs of the particle-based multiplex assays of the invention renders them suitable for even high throughput applications, including primary screening.

Methods of Detecting Multiple Analytes

Accordingly, one general class of embodiments provides methods of detecting analytes of interest. The methods include a) capturing a first analyte from a first sample on a first subset of particles (microspheres, microbeads, etc.), and separately capturing a second analyte from a second sample on a second subset of particles, wherein the particles of the second subset are distinguishable from those of the first subset; b) after step a), combining the first and second subsets of particles; and c) after step b), identifying at least a portion of the particles from each subset and determining whether those particles have analyte captured thereto. As noted above, the initial step of the assay—capturing the analytes to identifiable, distinguishable subsets of particles—is performed separately for the different samples, e.g., in different tubes or different wells of a multiwell plate (or different plates). The particles are combined (e.g., into a single tube or well) for the final read step, and are optionally combined for any processing required to detect the analytes before the read step (e.g., they can be combined prior to addition of a detection reagent).

The methods can be further multiplexed, for example, by using third, fourth, etc. distinguishable subsets of particles to capture third, fourth, etc. analytes from third, fourth, etc. samples and/or by using two or more distinguishable subsets of particles to capture two or more analytes from one or more of the samples. Additional variations on the methods can be employed, as described for the embodiments below.

Another general class of embodiments also provides methods of detecting analytes of interest. In this class of embodiments, a first sample comprising or putatively comprising a first group of one or more analytes and a second sample comprising or putatively comprising a second group of one or more analytes are provided. A first and a second population of particles (microspheres, microbeads, etc.) are also provided. (Additional samples and populations of particles are optionally also provided, as noted below.)

The first population of particles includes one or more subsets of particles (e.g., one for each different analyte in the first group). In embodiments in which the population comprises two or more subsets, a plurality of the particles in each subset are distinguishable from a plurality of the particles in the other subsets. (Typically, substantially all of the particles in each subset are distinguishable from substantially all of the particles in every other subset.) The particles in each subset comprise a capture molecule configured to capture one of the analytes of the first group. In embodiments in which the first population comprises two or more subsets of particles, the capture molecule on each subset is typically different from those on the other subsets of the first population (e.g., is configured to capture a different analyte); each subset of particles can thus capture a different, predetermined analyte.

Similarly, the second population of particles also includes one or more subsets of particles (e.g., one for each different analyte in the second group). A plurality of the particles in each subset of the second population are distinguishable from a plurality of the particles in the subsets of the first population. In addition, in embodiments in which the second population comprises two or more subsets, a plurality of the particles in each subset of the second population are distinguishable from a plurality of the particles in the other subsets of the second population. (Typically, substantially all of the particles in each subset are distinguishable from substantially all of the particles in every other subset.) The particles in each subset of the second population comprise a capture molecule configured to capture one of the analytes of the second group. In embodiments in which the second population comprises two or more subsets of particles, the capture molecule on each subset is typically different from those on the other subsets of the second population.

The first sample and the first population of particles are contacted with each other, and any analyte of the first group present in the first sample is captured on a selected subset of the first population of particles (i.e., the subset comprising the capture molecule configured to capture that analyte). The second sample and the second population of particles are contacted, and any analyte of the second group present in the second sample is captured on a selected subset of the second population of particles (i.e., the subset comprising the capture molecule configured to capture that analyte). The two populations are separately contacted with their corresponding samples, e.g., in separate containers (tubes, wells, etc.) and/or in separate operations.

The first and second populations of particles, along with any captured analytes, are then combined. Which subsets of particles have an analyte of interest captured thereon is then detected. Since a correlation exists between a particular subset of particles and a particular analyte from a particular sample, which subsets of particles bear captured analytes indicates which analytes were present in the first and second samples.

As noted previously, the methods are useful for multiplex detection of analytes, optionally highly multiplex detection. Thus, the first group of analytes to be detected from the first sample optionally comprises two or more, three or more, five or more, 10 or more, 20 or more, 30 or more, 40 or more, 50 or more, or even 100 or more analytes, and a like number of subsets of particles are provided in the first population. Thus, the first population optionally includes two or more, three or more, five or more, 10 or more, 20 or more, 30 or more, 40 or more, 50 or more, or even 100 or more distinguishable subsets of particles. Similarly, the second group of analytes to be detected from the second sample optionally comprises two or more, three or more, five or more, 10 or more, 20 or more, 30 or more, 40 or more, 50 or more, or even 100 or more analytes, and the second population optionally includes two or more, three or more, five or more, 10 or more, 20 or more, 30 or more, 40 or more, 50 or more, or even 100 or more distinguishable subsets of particles.

Similarly, the methods optionally include providing a third (fourth, fifth, etc.) sample comprising or suspected of comprising a third (fourth, fifth, etc.) group of one (two, three, four, etc.) or more analytes, and providing a third (fourth, fifth, etc.) population comprising one (two, three, four, etc.) or more subsets of particles distinguishable from each other and from those of the other populations and comprising capture molecules configured to capture the analytes of the third (fourth, fifth, etc.) group. Optionally, three or more, four or more, five or more, 10 or more, 20 or more, 30 or more, 40 or more, 50 or more, or even 100 or more samples, groups of analytes (each of which optionally includes one or more, two or more, three or more, five or more, 10 or more, 20 or more, 30 or more, 40 or more, 50 or more, or even 100 or more analytes), and particle populations (each of which optionally includes one or more, two or more, three or more, five or more, 10 or more, 20 or more, 30 or more, 40 or more, 50 or more, or even 100 or more subsets of particles) are provided. The additional samples and particle populations are contacted separately, and then combined with the first and second populations prior to detection as described above. It will be evident that the number of particle populations, subsets of particles in each population, etc. can be varied as desired for the particular application of interest. As just a few non-limiting examples, using the methods one, two, or a few analytes can be detected in a large number of samples, a large number of analytes can be detected from two or a few samples, 5-10 analytes can be detected from 5-10 samples, or 30-50 analytes can be detected from 2-10 or 2-20 samples (using, e.g., at least five populations having at least five subsets each, at least eight populations having at least eight subsets each, or at least ten populations having at least ten subsets each), limited essentially only by the number of available distinguishable particle sets. It will be evident that the various populations can, but need not, each include the same number of subsets of particles.

The capture molecule for a particular analyte can be essentially any molecule (or complex comprising a molecule) that can be configured to capture the analyte, e.g., any molecule that binds specifically to the analyte or that indirectly captures the analyte. For example, a capture molecule can comprise a polynucleotide (e.g., a polynucleotide capture probe, a nucleic acid binding site for a transcription factor, or an aptamer), a polypeptide (e.g., an antibody, a recombinant protein, an SH2 or PTB domain for capturing a tyrosine-phosphorylated polypeptide, an SH3 domain for capturing a proline rich polypeptide, a 14-3-3 domain for capturing a serine-phosphorylated polypeptide, a chromodomain for capturing a lysine-methylated polypeptide, a bromodomain for capturing a lysine-acetylated polypeptide, or a synthetic peptide), a substrate analog (e.g., a molecule that is a structural analog of an enzyme's substrate but that reacts very slowly or not at all and thus inhibits the enzyme by occupying its active site) and/or a small molecule (e.g., a ligand). A single subset of particles typically (but not necessarily) comprises a single type of capture molecule, while different subsets can comprise the same or different types of capture molecules. For example, one subset can comprise an antibody specific for a first protein while a second subset comprises an antibody specific for a second protein, or one subset can comprise an antibody specific for a first protein while a second subset comprises a single-stranded or double-stranded oligonucleotide binding site for a second protein. The capture molecules can be covalently or noncovalently associated with the particles, as described in greater detail in the "Microspheres and Other Particles" section below.

The capture molecules can be configured to capture their respective analytes directly or indirectly. Thus, in one aspect, the analytes bind directly to the capture molecules. For example, in this class of embodiments, the capture molecules can be antibodies specific for different analytes or polynucleotides complementary to different nucleic acid analytes. See, for example, the immunoassay, transcription factor, and phosphotyrosine polypeptide embodiments described below. In another aspect, the analytes bind directly to molecules which are in turn bound directly to the capture molecules. For example, the capture molecules can be polynucleotides complementary to other polynucleotides which also have regions complementary to nucleic acid analytes. See, e.g., the bDNA embodiments described below. Similarly, the analytes can bind to molecules which are bound via other molecules to the capture molecules.

As noted, the subsets of the first population comprise different capture molecules from each other, and the subsets of the second population likewise comprise different capture molecules from other subsets of the second population. In some embodiments, subsets of the first and second populations comprise different capture molecules from each other as well, e.g., in embodiments in which the capture molecules bind directly to the analytes and the analytes of the first and second groups are different. In other embodiments, there is overlap between the capture molecules on one or more subsets of the first and second populations. Thus, in one class of embodiments, the capture molecule on a subset of the particles of the second population is substantially identical to the capture molecule on a subset of the first population (e.g., the capture molecules can be the same, or they can have substantially identical polynucleotide or polypeptide sequences and/or about the same specificity and affinity for a given analyte; substantially identical sequences have a specified percentage of amino acid residues or nucleotides that are the same when compared and aligned for maximum correspondence, as measured using one of the sequence comparison algorithms available to persons of skill or by visual inspection, typically 95% or more, 97% or more, or even 99% or more). Optionally, the capture molecules on each of the two or more subsets of the particles in the second population are substantially identical to the capture molecules on subsets of the first population. This configuration can be employed, for example, when the capture molecules bind directly to the analytes and the analytes of the first and second groups are the same, or when the capture molecules capture the analytes indirectly, as will be described in greater detail below (see, e.g., the section entitled "Branched-Chain DNA Assays" below). In embodiments in which more than two populations of particles are employed, the capture molecules can, e.g., be the same or substantially identical from population to population, the capture molecules can be the same for some populations (or some subsets thereof) and different for others, or different populations can employ entirely different capture molecules.

The analytes can be essentially any molecules, complexes, etc. whose detection and/or quantitation is desired. Exemplary analytes include, but are not limited to, polypeptides (e.g., specific polypeptides, nucleic acid binding proteins, specific posttranslationally modified forms of specific polypeptides, such as phosphorylated, glycosylated, acetylated, ubiquitinated, sumoylated, hydroxylated, or methylated forms, antibodies, etc.), nucleic acids (e.g., DNAs, RNAs, mRNAs, ribosomal RNAs, microRNAs, transcription factor binding sites, and genomic DNAs or RNAs), drugs, compounds, chemicals, and small molecules. The analytes can comprise, for example, endogenous cellular proteins (e.g., an intracellular protein, a plasma membrane protein and/or a secreted protein encoded by the cell's nuclear, mitochondrial and/or chloroplast genome), proteins encoded by an infectious agent (e.g., a pathogenic virus, bacterium, protist, fungus or the like), endogenous nucleic acids (e.g., genomic DNA or mRNA), and/or nucleic acids derived from microorganisms (pathogenic or otherwise, e.g., bacterial or viral genomic RNA or DNA, plasmid DNA, or other extragenomic DNA). As just a few examples, the analytes can be derived from one or more of an animal, a human, a plant, a cultured cell, a microorganism, a virus, a bacterium, or a pathogen. The methods can thus be employed to determine protein or mRNA expression levels, presence or level of posttranslational modifications on proteins, presence or activity of nucleic acid binding proteins, presence or identity of pathogens, genotype, SNP detection, gene copy number, or enzyme activity, as just a few examples.

The methods are optionally employed to compare the presence (or amount) of analytes between samples from different sources. Thus, in one class of embodiments, the analytes of the first group and the analytes of the second group represent the same group of target molecules derived from different sources. For example, the analytes of the first and second groups can represent the same polypeptides or nucleic acids obtained from two different cell samples, tissues, or organisms; the methods can thus be used to compare expression of a particular protein or mRNA in different cell types or in treated versus untreated cells, as just one example. Different analytes can be of the same or different general types (e.g., all proteins, all nucleic acids, or a combination thereof).

In other applications, the methods are optionally employed to achieve a greater degree of multiplexing than can be achieved by conventional assays. For example, particle-based immunoassays can be limited in terms of the number of analytes that can be specifically captured from a single sample by cross-reactivity of the antibodies used as capture molecules. This can be overcome by the methods of the invention, where different populations of particles can have different capture molecules and thus capture different groups of analytes, e.g., from different sample aliquots of a single initial sample. Accordingly, in one class of embodiments, the analytes of the first group and the analytes of the second group are different target molecules.

As indicated above, the first and second (and optional third, fourth, etc.) samples can be identical (e.g., different aliquots of a single initial solution) or different (e.g., from different or differently treated cell lines, cell types, tissues, or organisms). The samples can be obtained or prepared from essentially any desired source. For example, a sample can be derived from an animal (e.g., a mammal, an invertebrate or an insect), a human, a plant, a cultured cell, and/or a microorganism. The sample can be derived, e.g., from a tissue, a biopsy or a tumor, e.g., from a human patient. The sample can comprise, for example, one or more of a cell lysate (e.g., a lysate of cultured cells, a tissue lysate or a lysate of peripheral blood cells), an intercellular fluid, a conditioned culture medium, or a bodily fluid (e.g., blood, serum, saliva, urine, sputum or spinal fluid).

Analytes captured on the particles are typically detected by associating a label with the analytes. In some embodiments, each analyte comprises a label or has a label associated with it before the analytes are captured on the particles, while in other embodiments, the label is associated with the analytes after capture but before the particle populations are combined. In such embodiments, detecting which subsets of particles have an analyte captured thereon comprises identifying at least a portion of the particles from each subset and detecting the presence or absence of the label on those particles. For many applications, however, associating the label with the analytes after their capture on the particles and after combination of the particle populations is more convenient, requires fewer manipulations, and results in consumption of fewer reagents. Thus, in one aspect, detecting which subsets of particles have an analyte of interest captured on the particles involves, after combination of the particle populations, associating a label with any of the analytes captured on the particles, identifying at least a portion of the particles from each subset, and detecting the presence or absence of the label on those particles. Typically, the label is provided as part of a detection reagent (e.g., a molecule or complex) that binds, directly or indirectly through other molecules, to one or more of the analytes. Thus, in one class of embodiments, a detection reagent comprising the label is provided and contacted with the combined populations of particles, whereby the detection reagent binds directly or indirectly to any analyte captured on the particles, thereby associating the label with any analyte captured on the particles.

In some embodiments, the detection reagent binds directly to one or more of the analytes (e.g., for each analyte a labeled antibody or labeled polynucleotide can be provided that binds specifically to that analyte, or a labeled antibody that binds to an epitope common to all the analytes can be employed as a detection reagent), while in other embodiments the detection reagent binds to one or more molecules that are in turn bound to the analytes (e.g., each analyte can be recognized by a primary antibody specific for that analyte and the detection reagent can be labeled secondary antibody that can bind to all of the primary antibodies, or nucleic acid analytes can be recognized by biotinylated polynucleotides and the detection reagent can be labeled streptavidin). Exemplary detection reagents include, but are not limited to, nucleic acids (e.g., polynucleotide probes or aptamers), polypeptides (e.g., antibodies, synthetic peptides, or protein domains), substrate analogs, and/or small molecules. In exemplary useful embodiments, the detection reagent is a labeled antibody (e.g., an antibody against a particular polypeptide or other molecule, anti-digoxigenin used to bind digoxigenin-containing DNA or other molecules, or anti-fluorescein used to recognize fluorescein-labeled molecules), a labeled polynucleotide, or a labeled biotin-binding moiety such as avidin or streptavidin (e.g., streptavidin-phycoerythrin).

Fluorescent labels are typically preferred for ease of detection. Fluorescent emission by the label is typically distinguishable from any fluorescent emission by the particles; many suitable fluorescent label-fluorescent particle combinations are possible, and selection of an appropriate combination for a particular application is routine for one of skill. Fluorescent emission by the label can be conveniently detected, and subsets of particles identified, using, e.g., a flow cytometer or similar instrument. When multiple detection reagents are used to detect the presence of the analytes, the label for each of the detection reagents is typically but not necessarily the same.

The methods can be qualitative or quantitative. For example, fluorescent signal from a detection reagent comprising a fluorescent label can be detected to indicate the presence or absence of the detection reagent and therefore of the corresponding analyte(s), or the fluorescent signal can be quantitated to quantitate the analyte(s). Thus, in one class of embodiments, an intensity of the signal from the label is measured, and the intensity of the signal for a given subset of particles is correlated with a quantity of the corresponding analyte of interest present. One of skill can determine appropriate conditions for a quantitative assay by methods known in the art (e.g., using non-limiting concentrations of capture molecules and detection reagents, appropriate controls, and the like; for example, microspheres that have captured analytes from a sample can be analyzed in parallel with control microsphere sets, e.g., microspheres exposed to known amounts of a control analyte).

As another example, rather than detecting analytes captured on the particles by associating a label with the analytes, detection can, e.g., be based on competitive binding. In a competitive format where a given analyte is to be detected, a labeled version of the analyte is provided (typically, a fixed amount of the labeled analyte, or of each labeled analyte in embodiments in which there is more than one per group, is contacted with the particles and the sample). Unlabeled analyte present in the test sample (e.g., the first or second sample) is then measured by its ability to compete with the labeled analyte in the assay. Typically, the unlabeled analyte, when present in the sample, blocks the ability of the labeled analyte to bind to the corresponding capture molecule because that binding site is already occupied. (That is, the labeled version of the analyte and any analyte present in the sample compete for a limited amount of the capture molecule. Limiting the amount of available capture molecule is conveniently achieved, e.g., by limiting the number of particles employed.) Thus, in a competitive assay, less label captured and measured in the assay means more of the unlabeled analyte is present in the test sample; the amount of analyte in the test sample is inversely related to the amount of label measured in the competitive format. Competitive formats can be particularly useful, e.g., where a matched pair of antibodies (or other molecules suitable for use, e.g., as a capture molecule and detection reagent) are not available or for detection of a small analyte (e.g., where simultaneous binding of a capture molecule and a detection reagent is hindered or precluded by steric hindrance). As for the noncompetitive formats above, the label is optionally a fluorescent label, and the assay can be quantitative or qualitative.

The particles are optionally washed at any of various steps to remove unbound material from the particles, e.g., with a solution comprising a buffer, salt, detergent, blocking agent, and/or the like. For example, the particles can be washed after capture of the analytes (e.g., before or after combination of the particle populations) but before the detection step. In certain embodiments, washing is conveniently performed after combination of the particle populations, particularly where capture of analyte(s) to the capture molecule(s) is slow, analyte concentration is low, and/or the particles are pelleted during combination such that they present less available surface area to the solution. For other embodiments, e.g., where analyte concentration is high and/or binding is fast, washing is optionally prior to combination of the populations. The particles can also or instead be washed during the detection step, for example, after addition of the detection reagent but before detection of the label.

A variety of suitable particles are known in the art, and many are commercially available. In one class of embodiments, the particles are microspheres, and typically the microspheres of each subset are distinguishable from those of the other subsets on the basis of their fluorescent emission spectra, their diameter (i.e., their size), or a combination thereof. See the section entitled "Microspheres and Other Particles" hereinbelow for additional details and other exemplary suitable particles.

It will be evident that essentially any particle-based assay can be multiplexed or further multiplexed using the methods of the present invention. A few representative examples are described below to illustrate various aspects of the invention (e.g., detection of different types of analytes, detection when the analytes of the different groups are the same versus when they are different target molecules, direct versus indirect capture of analytes by capture molecules, capture molecule types and configurations, various detection reagents, etc.). While only a few assays are described in detail, it will be evident that other particle-based assays can be similarly adapted to the practice of the present invention by using two or more particle populations including distinguishable particle subsets for two or more samples and combining the populations before the read step in which the particles are identified and analyte thereon identified (and optionally before processing for detection).

Furthermore, essentially any assay based on binding of analytes to distinguishable moieties can be multiplexed or further multiplexed using the methods of the present invention, whether the moieties are particles such as those described herein or another type of distinguishable assay component. Thus, as just one example, the NanoString assay described by Geiss et al. (2008) "Direct multiplexed measurement of gene expression with color-coded probe pairs" Nature Biotechnology 26:317-325 can be further multiplexed, e.g., by combining two or more sets of reporter probes with target mRNAs hybridized thereto with each other prior to their immobilization on a solid support and detection.

Accordingly, one general class of embodiments provides methods of detecting analytes of interest. In the methods, a first sample comprising or putatively comprising a first group of one or more analytes and a second sample comprising or putatively comprising a second group of one or more analytes are provided. A first and second set of reporter entities are also provided. (Additional samples and sets of reporter entities are optionally also provided.)

The first set includes one or more reporter entities (typically, one for each different analyte in the first group), each of which is configured to capture a different one of the analytes of the first group. In embodiments in which the first set comprises two or more reporter entities, the reporter entities of the first set are distinguishable from each other. Similarly, the second set includes one or more reporter entities (typically, one for each different analyte in the second group), each of which is configured to capture a different one of the analytes of the second group. In embodiments in which the second set comprises two or more reporter entities, the reporter entities of the second set are distinguishable from each other. Each of the reporter entities of the second set is distinguishable from the reporter entities of the first set.

The first sample and the first set of reporter entities are contacted with each other, and any analyte of the first group present in the first sample is captured to a selected reporter entity of the first set (i.e., the entity configured to capture that analyte). The second sample and the second set of reporter entities are contacted with each other, and any analyte of the second group present in the first sample is captured to a selected reporter entity of the second set (i.e., the entity configured to capture that analyte). The two sets are separately contacted with their corresponding samples, e.g., in separate containers (tubes, wells, etc.) and/or in separate operations.

The first and second sets of reporter entities, along with any captured analytes, are then combined. Which reporter entities have an analyte of interest captured thereon is then detected. Since a correlation exists between a particular reporter entity and a particular analyte from a particular sample, which reporter entities bear captured analytes indicates which analytes were present in the first and second samples.

A reporter entity can be essentially any entity or assay component that is distinguishable by one or more identifying characteristics (e.g., sequence, size, fluorescence, or bar code) and to which an analyte can be captured. Exemplary reporter entities include, but are not limited to, particles (e.g., as for the embodiments described above) and nucleic acids (e.g., nucleic acids distinguishable by their different sequences, such as the reporter probes of Geiss et al. supra). A reporter entity can include a label (e.g., the reporter entity can be a fluorescently labeled microbead or nucleic acid) or it can be configured to bind a label or another labeled entity. The reporter entities can bind directly to the analytes to capture them or they can capture the analytes indirectly, as for the embodiments described above.

Essentially all of the features noted for the methods above apply to these embodiments as well, as relevant; for example, with respect to number of analytes per group, groups of analytes, sets of reporter entities, and/or reporter entities per set, type of analytes, source of the samples, inclusion of detection reagent, and/or the like. As for the embodiments above, the analytes of the first and second groups can be the same target molecules from different sources or they can be different target molecules; accordingly, the reporter entities of the first and second sets can be configured to capture the same or different analytes (or a combination thereof).

Immunoassays

A simple particle-based immunoassay in which a single target molecule is detected from two different samples is schematically illustrated in FIG. 1. As shown in Panels A-B, a first population of microspheres is provided and contacted with a first sample comprising the analyte. In this example, since only a single analyte is to be detected, the particle population includes only a single subset of microspheres comprising a capture molecule specific for the analyte (in this example, a polypeptide having two epitopes, one represented by a triangle and the other by a circle). The analyte is captured on the microspheres by direct binding of the analyte to the capture molecule. Similarly, in Panels C-D, the analyte is captured from a second sample on a second population of particles, which also includes only a single subset of microspheres, distinguishable from those of the first population/subset but bearing the same capture molecule.

The first and second populations are then combined, as shown in Panel E. Material not bound to the particles is removed, e.g., by washing before or after combination of the populations. A biotinylated antibody that recognizes the analyte is provided (biotin is represented by a hexagon) and bound to the analyte, as shown in Panel F, and then a fluorescently labeled streptavidin detection reagent is provided and bound in turn to the antibody, as shown in Panel G. (The label is represented by a star.) The mixture is then analyzed on a flow cytometer or other instrument designed to identify each particle species (and therefore the sample from which the captured analyte originated) and measure the detection reagent, as shown in Panel H. In this example, the microsphere subsets are distinguishable by their differing fluorescent emission spectra (schematically illustrated in Panel H by the differing intensities (I) of emission at $\lambda_2$ and $\lambda_3$). Emission by the detection reagent (schematically illustrated at $\lambda_1$) is distinguishable from emission by the microspheres. As noted previously, the method is optionally quantitative, since the intensity of emission by the detection reagent is proportional to the amount of detection reagent bound to a captured protein (and therefore, under appropriate conditions, to the amount of that protein initially present in each sample).

A number of variations on this example will immediately be evident. For example, the detection antibody can itself comprise a label instead of being biotinylated and indirectly capturing a label, a labeled secondary antibody can be bound to the detection antibody, or a biotinylated secondary antibody can be bound to the detection antibody and then detected with labeled streptavidin. More than one analyte can be detected from one or both samples by including additional microsphere subsets with appropriate capture molecules in the first and/or second populations; the additional analytes can be detected with the same detection antibody if they share a common epitope, or with additional detection antibodies if not. Additional microsphere populations can be included to detect analyte(s) from additional samples. As noted previously, the same or different analytes (or a combination thereof) can be detected from the different samples. As noted above, immunoassays (or other assays of the invention) can also be based on competitive binding.

Branched-Chain DNA Assays

Particle-based branched-chain DNA (bDNA) assays can be employed to detect nucleic acid analytes. bDNA signal amplification technology has been used, e.g., to detect and quantify mRNA transcripts in cell lines and to determine viral loads in blood. The bDNA assay is a sandwich nucleic acid hybridization procedure that enables direct measurement of mRNA expression, e.g., from crude cell lysate. It provides direct quantification of nucleic acid molecules at physiological levels. Several advantages of the technology distinguish it from other DNA/RNA amplification technologies, including linear amplification, good sensitivity and dynamic range, great precision and accuracy, simple sample preparation procedure, and reduced sample-to-sample variation.

In brief, in a typical bDNA assay for gene expression analysis, a target mRNA whose expression is to be detected is released from cells and captured by a Capture Probe (CP) on a solid surface through synthetic oligonucleotide probes called Capture Extenders (CEs). Each capture extender has a first polynucleotide sequence that can hybridize to the target mRNA and a second polynucleotide sequence that can hybridize to the capture probe. Typically, two or more capture extenders are used. Probes of another type, called Label Extenders (LEs), hybridize to different sequences on the target mRNA and to sequences on an amplification multimer. Additionally, Blocking Probes (BPs) are often used to reduce non-specific target probe binding. A probe set for a given mRNA thus consists of CEs, LEs, and optionally BPs for the target mRNA. The CEs, LEs, and BPs are complementary to nonoverlapping sequences in the target mRNA, and are typically, but not necessarily, contiguous.

Signal amplification begins with the binding of the LEs to the target mRNA. An amplification multimer is then typically hybridized to the LEs. The amplification multimer has multiple copies of a sequence that is complementary to a label probe (it is worth noting that the amplification multimer is typically, but not necessarily, a branched-chain nucleic acid; for example, the amplification multimer can be a branched, forked, or comb-like nucleic acid or a linear nucleic acid). A label, for example, alkaline phosphatase (or a fluorescent label), is covalently attached to each label probe. (Alternatively, the label can be noncovalently bound to the label probes.) In the final step, labeled complexes are detected, e.g., by the alkaline phosphatase-mediated degradation of a chemilumigenic substrate (or fluorescent emission by the label); the amount of chemiluminescence (or fluorescence) is proportional to the level of mRNA expressed from the target gene.

In the preceding example, the amplification multimer and the label probes comprise a label probe system. In another example, the label probe system also comprises a preamplifier, e.g., as described in U.S. Pat. No. 5,635,352 and U.S. Pat. No. 5,681,697, which further amplifies the signal from a single target mRNA molecule. In yet another example, the label extenders hybridize directly to the label probes and no amplification multimer or preamplifier is used, so the signal from a single target mRNA molecule is only amplified by the number of distinct label extenders that hybridize to that mRNA.

Basic bDNA assays for single targets have been well described. See, e.g., U.S. Pat. No. 4,868,105 to Urdea et al. entitled "Solution phase nucleic acid sandwich assay"; U.S. Pat. No. 5,635,352 to Urdea et al. entitled "Solution phase nucleic acid sandwich assays having reduced background noise"; U.S. Pat. No. 5,681,697 to Urdea et al. entitled "Solution phase nucleic acid sandwich assays having reduced background noise and kits therefor"; U.S. Pat. No. 5,124,246 to Urdea et al. entitled "Nucleic acid multimers and amplified nucleic acid hybridization assays using same"; U.S. Pat. No. 5,624,802 to Urdea et al. entitled "Nucleic acid multimers and amplified nucleic acid hybridization assays using same"; U.S. Pat. No. 5,849,481 to Urdea et al. entitled "Nucleic acid hybridization assays employing large comb-type branched polynucleotides"; U.S. Pat. No. 5,710,264 to Urdea et al. entitled "Large comb type branched polynucleotides"; U.S. Pat. No. 5,594,118 to Urdea and Horn entitled "Modified N-4 nucleotides for use in amplified nucleic acid hybridization assays"; U.S. Pat. No. 5,093,232 to Urdea and Horn entitled "Nucleic acid probes"; U.S. Pat. No. 4,910,300 to Urdea and Horn entitled "Method for making nucleic acid probes"; U.S. Pat. No. 5,359,100; U.S. Pat. No. 5,571,670; U.S. Pat. No. 5,614,362; U.S. Pat. No. 6,235,465; U.S. Pat. No. 5,712,383; U.S. Pat. No. 5,747,244; U.S. Pat. No. 6,232,462; U.S. Pat. No. 5,681,702; U.S. Pat. No. 5,780,610; U.S. Pat. No. 5,780,227 to Sheridan et al. entitled "Oligonucleotide probe conjugated to a purified hydrophilic alkaline phosphatase and uses thereof"; U.S. patent application Publication No. US2002172950 by Kenny et al. entitled "Highly sensitive gene detection and localization using in situ branched-DNA hybridization"; Wang et al. (1997) "Regulation of insulin preRNA splicing by glucose" Proc Nat Acad Sci USA 94:4360-4365; Collins et al. (1998) "Branched DNA (bDNA) technology for direct quantification of nucleic acids: Design and performance" in Gene Quantification, F Ferre, ed.; and Wilber and Urdea (1998) "Quantification of HCV RNA in clinical specimens by branched DNA (bDNA) technology" Methods in Molecular Medicine: Hepatitis C 19:71-78. In addition, kits for performing basic bDNA assays (Quanti-Gene® kits, comprising instructions and reagents such as amplification multimers, alkaline phosphatase labeled label probes, chemilumigenic substrate, capture probes immobilized on a solid support, and the like) are commercially available, e.g., from Panomics, Inc. (on the world wide web at www (dot) panomics (dot) com). Software for designing probe sets for a given mRNA target (i.e., for designing the regions of the CEs, LEs, and optionally BPs that are complementary to the target) is also commercially available (e.g., ProbeDesigner™ from Panomics, Inc.; see also Bushnell et al. (1999) "ProbeDesigner: for the design of probe sets for branched DNA (bDNA) signal amplification assays Bioinformatics 15:348-55).

Multiplex bDNA assays have also been described. See commonly owned U.S. application publication 2006/0286583 entitled "Multiplex branched-chain DNA assays" by Luo et al. for description of capture extender designs that facilitate particle-based multiplex detection in bDNA assays, and commonly owned U.S. application publication 2006/0263769 entitled "Multiplex capture of nucleic acids" by Luo et al. for description of capture of nucleic acid analytes generally. See also commonly owned U.S. application publication 2007/0015188 entitled "Multiplex detection of nucleic acids" by Luo et al. for additional details regarding design of label extenders and label probe systems in bDNA assays. QuantiGene® Plex kits for performing basic multiplex bDNA assays comprising instructions and reagents such as preamplifiers, amplification multimers, label probes, capture probes immobilized on microspheres, and the like are commercially available, e.g., from Panomics, Inc.

Multiplex bDNA assays can be adapted to the methods of the present invention. Thus, in one exemplary class of embodiments, the analytes are nucleic acids; the capture molecules are polynucleotide capture probes; capturing any analytes of the first group present in the first sample on a selected subset of the particles in the first population comprises i) providing one or more subsets of one or more (preferably two or more) capture extenders (i.e., one subset for each analyte), wherein each subset of capture extenders is configured to hybridize to one of the nucleic acid analytes of the first group, and wherein the capture extenders in each subset are configured to hybridize to one of the capture probes on the particles of the first population, and ii) hybridizing any nucleic acid analyte of the first group present in the first sample to its corresponding subset of capture extenders and hybridizing the subset of capture extenders to its corresponding capture probe, whereby the nucleic acid analyte is captured on the selected subset of particles comprising that capture probe; capturing any analytes of the second group present in the second sample on a selected subset of the particles in the second population comprises i) providing one or more subsets of one or more (preferably two or more) capture extenders (i.e., one subset for each analyte), wherein each subset of capture extenders is configured to hybridize to one of the nucleic acid analytes of the second group, and wherein the capture extenders in each subset are configured to hybridize to one of the capture probes on the particles of the second population, and ii) hybridizing any nucleic acid analyte of the second group present in the second sample to its corresponding subset of capture extenders and hybridizing the subset of capture extenders to its corresponding capture probe, whereby the nucleic acid analyte is captured on the selected subset of particles comprising that capture probe; and detecting which subsets of particles have an analyte of interest captured on the particles comprises i) associating a label with any analyte captured on the particles by hybridizing one or more label extenders (generally two or more) and a label probe system comprising the label to any nucleic acid analyte captured on the particles, ii) identifying at least a portion of the particles from each subset, and iii) detecting the presence or absence of the label on those particles.

Figure 2:
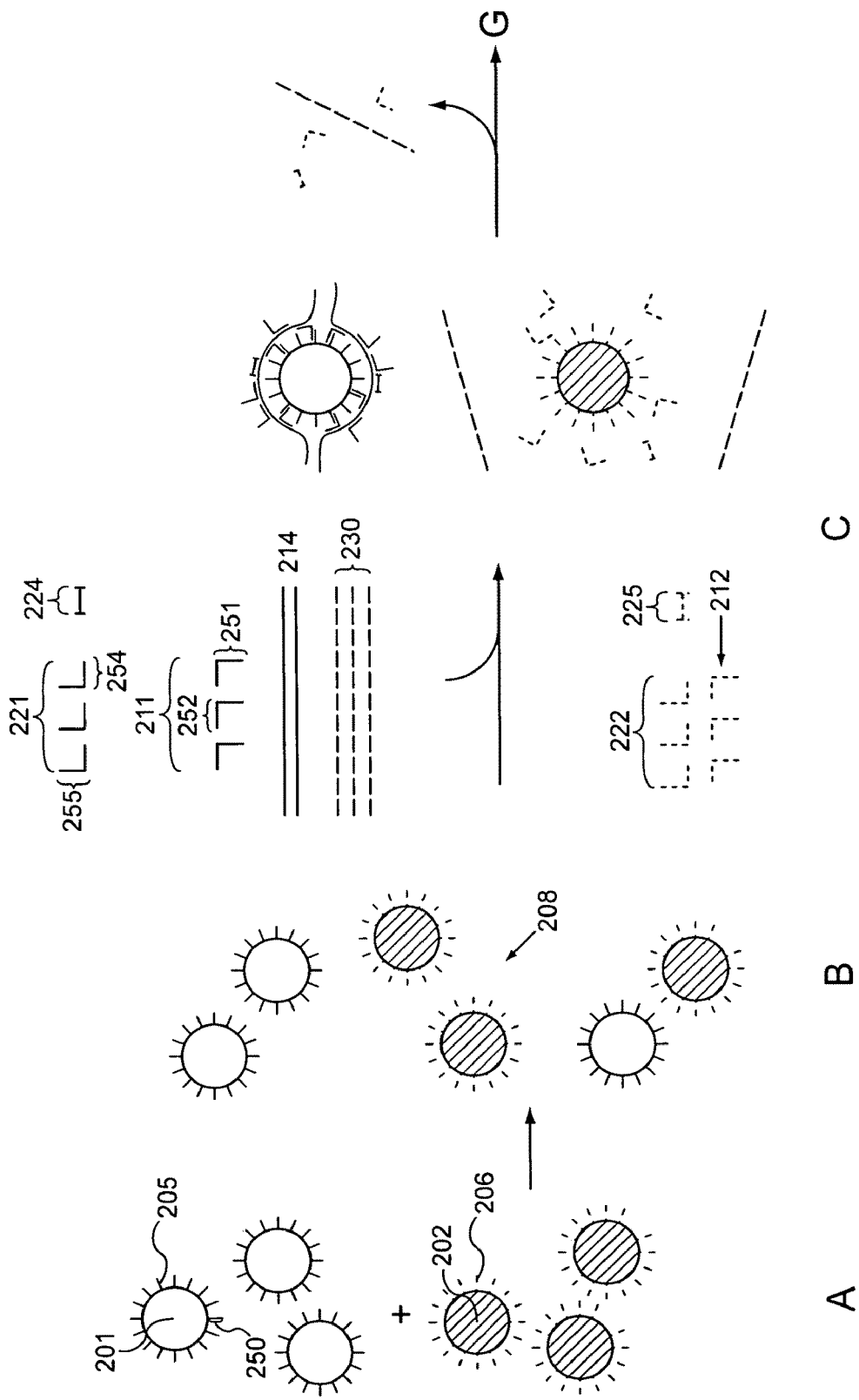
FIG. 2 Panels A-I schematically illustrate a multiplex bDNA assay in which different populations of particles include the same set of capture molecules and are used to capture the same group of nucleic acid analytes from different samples.
Figure 2:
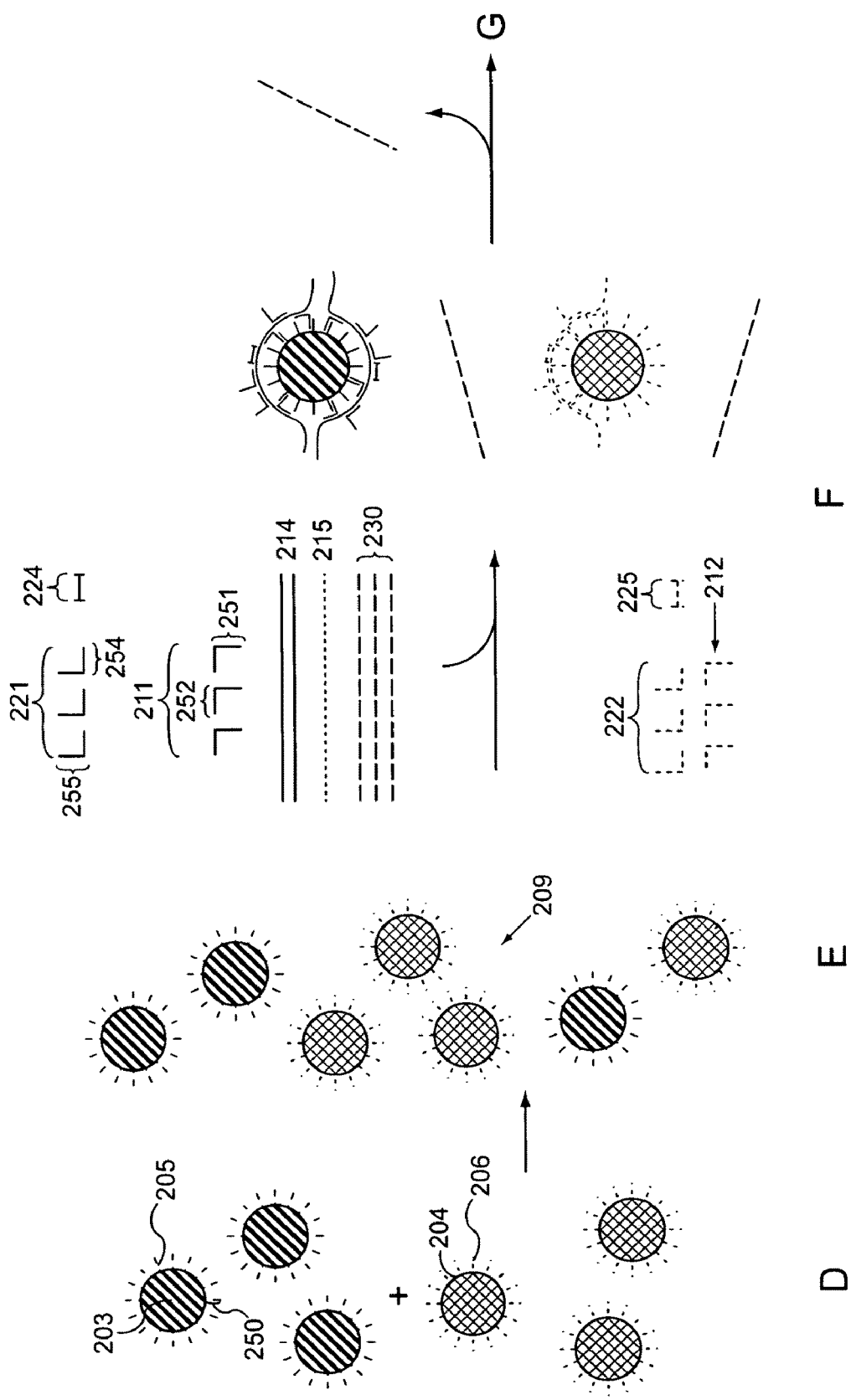
Figure 2:
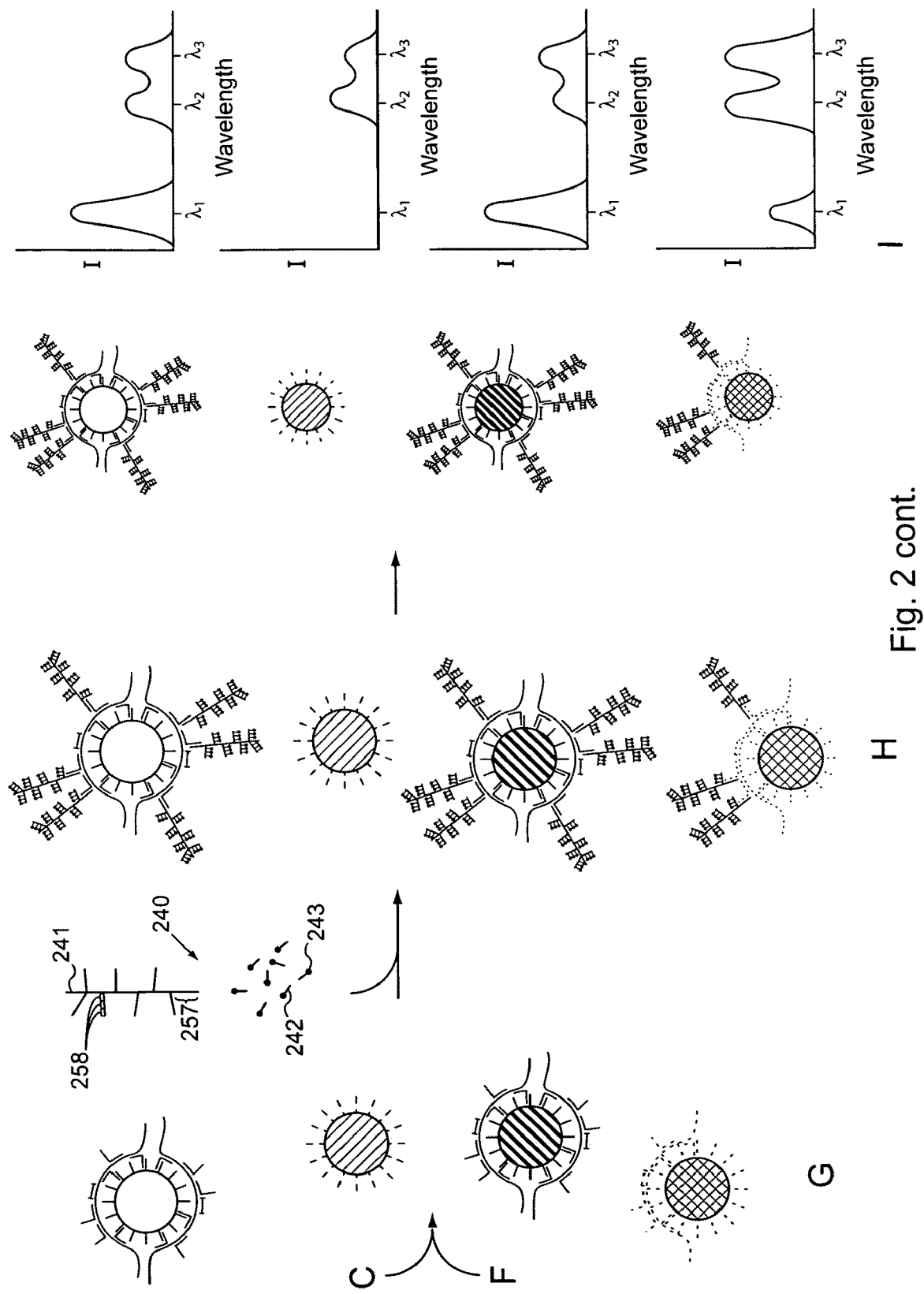

An exemplary embodiment in which two nucleic acid analytes are detected from two different samples is schematically illustrated in FIG. 2. Panel A illustrates two distinguishable subsets of microspheres 201 and 202, which have associated therewith capture probes 205 and 206, respectively. Each capture probe includes a sequence C-2 (250), which is different from subset to subset of microspheres. The two subsets of microspheres are mixed to form first pooled population 208 (Panel B). A subset of three capture extenders is provided for each nucleic acid analyte of interest; subset 211 for nucleic acid 214 and subset 212 for nucleic acid 215 which is not present in the exemplary first sample. Each capture extender includes sequences C-1 (251, complementary to the respective capture probe's sequence C-2) and C-3 (252, complementary to a sequence in the corresponding nucleic acid of interest). Two subsets of label extenders (221 and 222 for nucleic acids 214 and 215, respectively) and two subsets of blocking probes (224 and 225 for nucleic acids 214 and 215, respectively) are also provided. Each label extender includes sequences L-1 (254, complementary to a sequence in the corresponding nucleic acid of interest) and L-2 (255, complementary to M-1). Non-target nucleic acids 230 are also present in the sample of nucleic acids. It will be evident that double-stranded nucleic acids of interest will typically be denatured before hybridization with capture extenders, label extenders, and the like.

Nucleic acids 214 and 215 (when present in the sample) are hybridized to their corresponding subset of capture extenders (211 and 212, respectively), and the capture extenders are hybridized to the corresponding capture probes (205 and 206, respectively), capturing nucleic acids 214 and 215 (when present) on microspheres 201 and 202, respectively (Panel C). Materials not bound to the microspheres (e.g., capture extenders 212, nucleic acids 230, etc.) are optionally separated from the microspheres by washing (before or, more typically, after combination of the two populations).

As shown in Panel D, two additional distinguishable subsets of microspheres 203 and 204, which have associated therewith capture probes 205 and 206, respectively, are also provided. (Note that one capture probe is therefore present on both microspheres 201 and 203, while another capture probe is present on both microspheres 202 and 204.) The two subsets of microspheres are mixed to form second pooled population 209 (Panel E). Since the same nucleic acid analytes are to be detected in the second sample as in the first in this example, capture extender subsets 211 and 212 are again provided for nucleic acids 214 and 215, respectively, as are label extender subsets 221 and 222 and blocking probe subsets 224 and 225. Non-target nucleic acids 230 are also present in the second sample.

Nucleic acids 214 and 215 are hybridized to their corresponding subset of capture extenders (211 and 212, respectively), and the capture extenders are hybridized to the corresponding capture probes (205 and 206, respectively), capturing nucleic acids 214 and 215 on microspheres 203 and 204, respectively (Panel F). Materials not bound to the microspheres (e.g., nucleic acids 230) are optionally separated from the microspheres by washing (before or, more typically, after combination of the two populations).

The first and second populations of microspheres are combined, as shown in Panel G. Next, label probe system 240 including amplification multimer 241 (which includes sequences M-1 257 and M-2 258) and label probe 242 (the detection reagent) which contains label 243 is hybridized to label extenders 221 and 222, which are hybridized to nucleic acids 214 and 215, respectively (Panel H). Materials not captured on the microspheres are optionally removed by washing the microspheres. Microspheres from each subset are identified, e.g., by their fluorescent emission spectrum ($\lambda_2$ and λ₃, Panel I), and the presence or absence of the label on each subset of microspheres is detected (λ₁, Panel I). Since each nucleic acid analyte from each sample is associated with a distinct subset of microspheres, the presence of the label on a given subset of microspheres correlates with the presence of the corresponding nucleic acid in a particular original sample. As noted previously, the method is optionally quantitative, since the intensity of emission by the label is proportional to the amount of label probe bound to a captured nucleic acid analyte (and therefore, under appropriate conditions, to the amount of that nucleic acid initially present in each sample).

As depicted in FIG. 2, all of the label extenders in all of the subsets typically include an identical sequence L-2. Optionally, however, different label extenders (e.g., label extenders in different subsets) can include different sequences L-2. Also as depicted in FIG. 2, each capture probe typically includes a single sequence C-2 and thus hybridizes to a single capture extender. Optionally, however, a capture probe can include two or more sequences C-2 and hybridize to two or more capture extenders. Similarly, as depicted, each of the capture extenders in a particular subset typically includes an identical sequence C-1, and thus only a single capture probe is needed for each subset of particles; however, different capture extenders within a subset optionally include different sequences C-1 (and thus hybridize to different sequences C-2, within a single capture probe or different capture probes on the surface of the corresponding subset of particles). A preamplifier is optionally included.

Capture probes, capture extenders, label extenders, preamplifiers, amplification multimers, and/or label probes optionally comprise at least one non-natural nucleotide. For example, a capture probe and the corresponding capture extender optionally comprise, at complementary positions, at least one pair of non-natural nucleotides that base pair with each other but that do not Watson-Crick base pair with the bases typical to biological DNA or RNA (i.e., A, C, G, T, or U), e.g., isoG, isoC, and other nucleotides used in the AEGIS system (Artificially Expanded Genetic Information System, available from EraGen Biosciences, www (dot) eragen (dot) com; see, e.g., U.S. Pat. No. 6,001,983, U.S. Pat. No. 6,037,120, and U.S. Pat. No. 6,140,496). As another example, the polynucleotides can include one or more Locked NucleicAcid™ (LNA) nucleotides (available from Exiqon A/S, www (dot) exiqon (dot) com; see, e.g., SantaLucia Jr. (1998) Proc Natl Acad Sci 95:1460-1465); LNA Watson-Crick base pair with the bases typical to biological DNA or RNA but confer increased thermal stability and discriminatory power on the resulting duplexes. Use of such non-natural nucleotides can, for example, reduce background and/or simplify probe design by decreasing cross hybridization, or it can permit use of shorter polynucleotides when the non-natural base pairs have higher binding affinities than do natural base pairs. (In general, such non-natural nucleotides are optionally included in polynucleotide capture molecules and/or detection reagents in any of the embodiments herein.)

A number of variations on this example will immediately be evident. For example, additional subsets of microspheres, capture extenders, label extenders, and optional blocking probes can be provided for detection of additional analytes in each sample. Similarly, additional populations of microspheres can be added to detect analytes (from the same or different groups) from additional samples.

Figure 3:
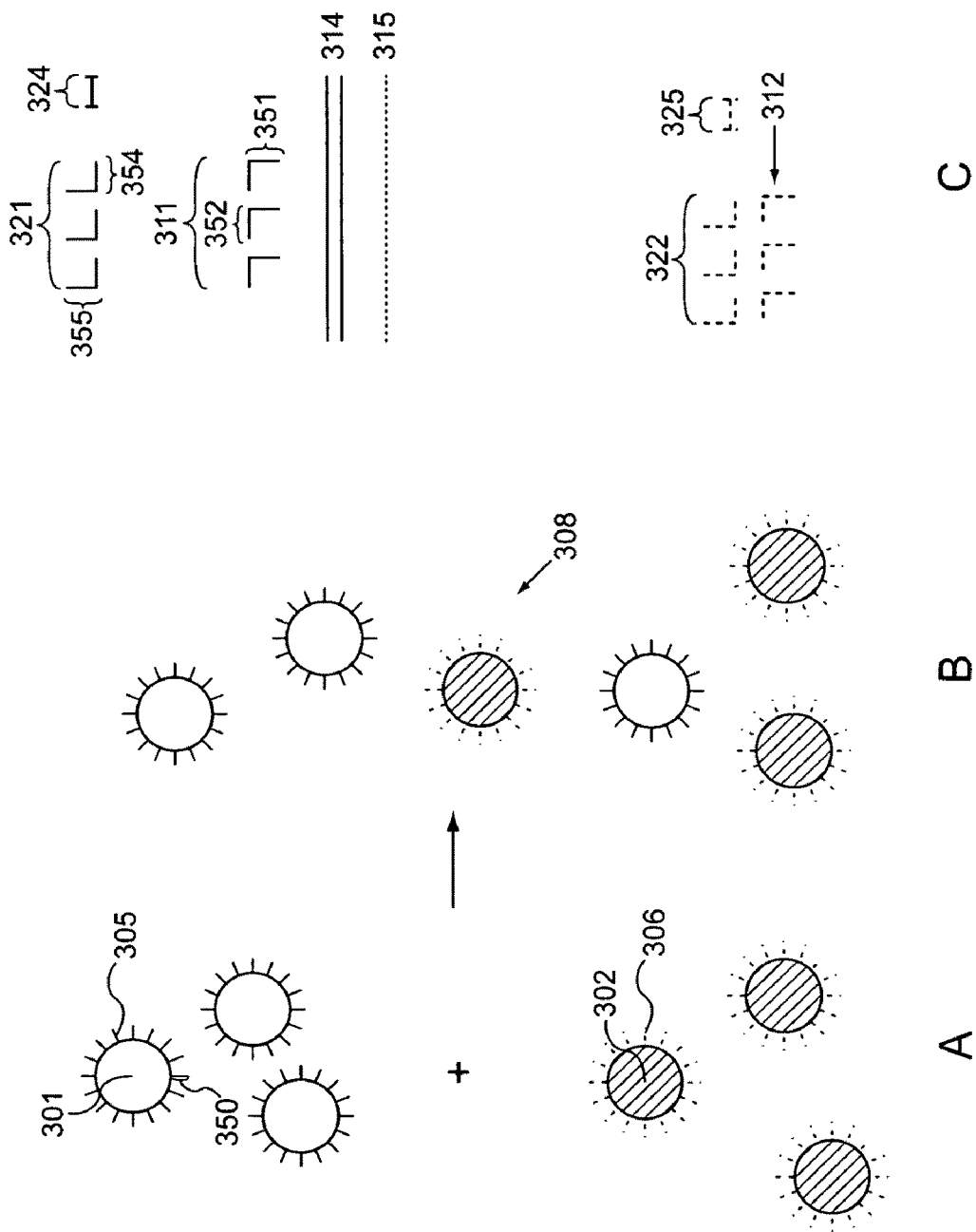
FIG. 3 Panels A-F schematically illustrate initial steps of a multiplex bDNA assay in which different populations of particles include the same set of capture molecules but are used to capture different groups of nucleic acid analytes through different sets of capture extenders.
Figure 3:
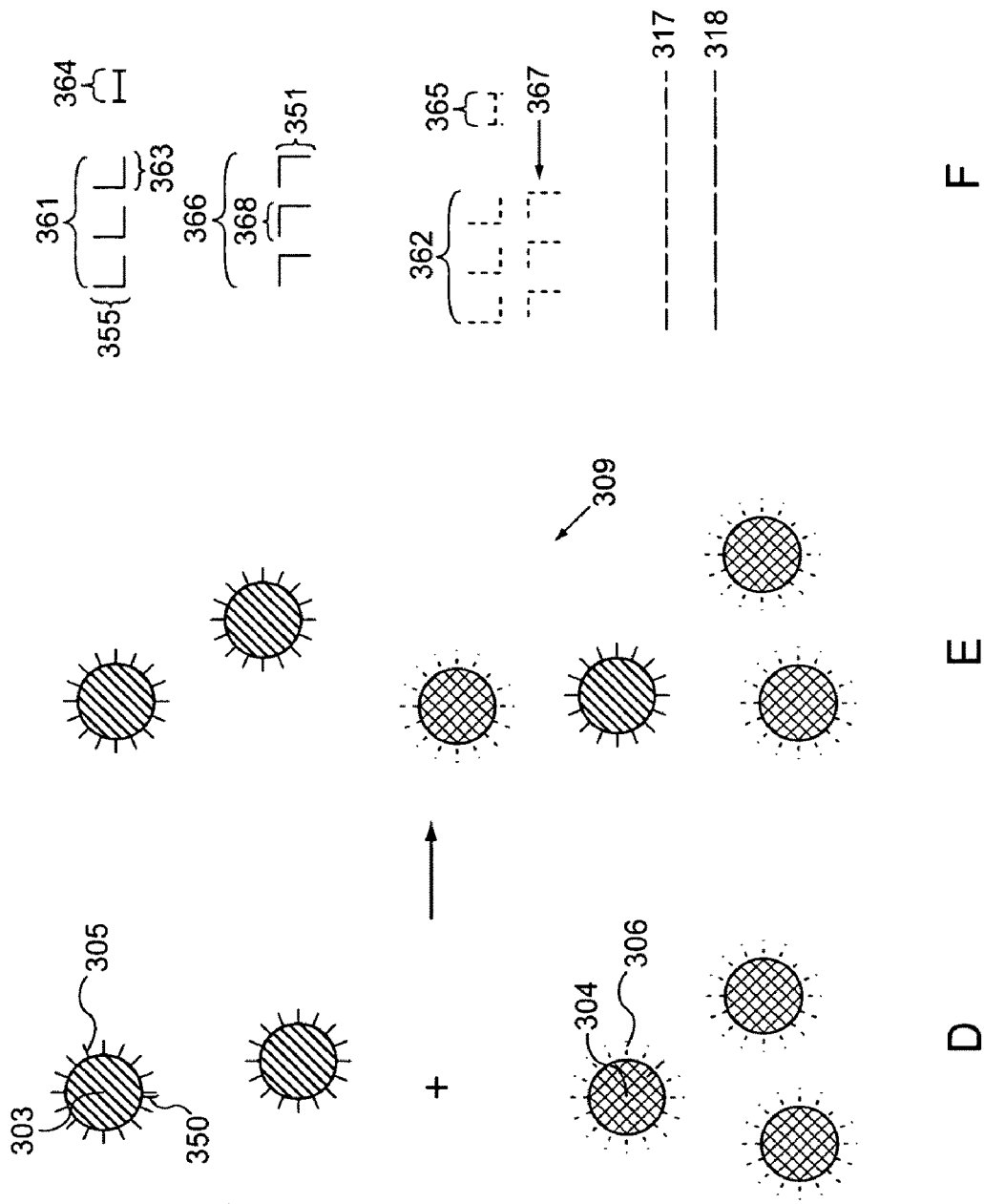
Figure 4A:
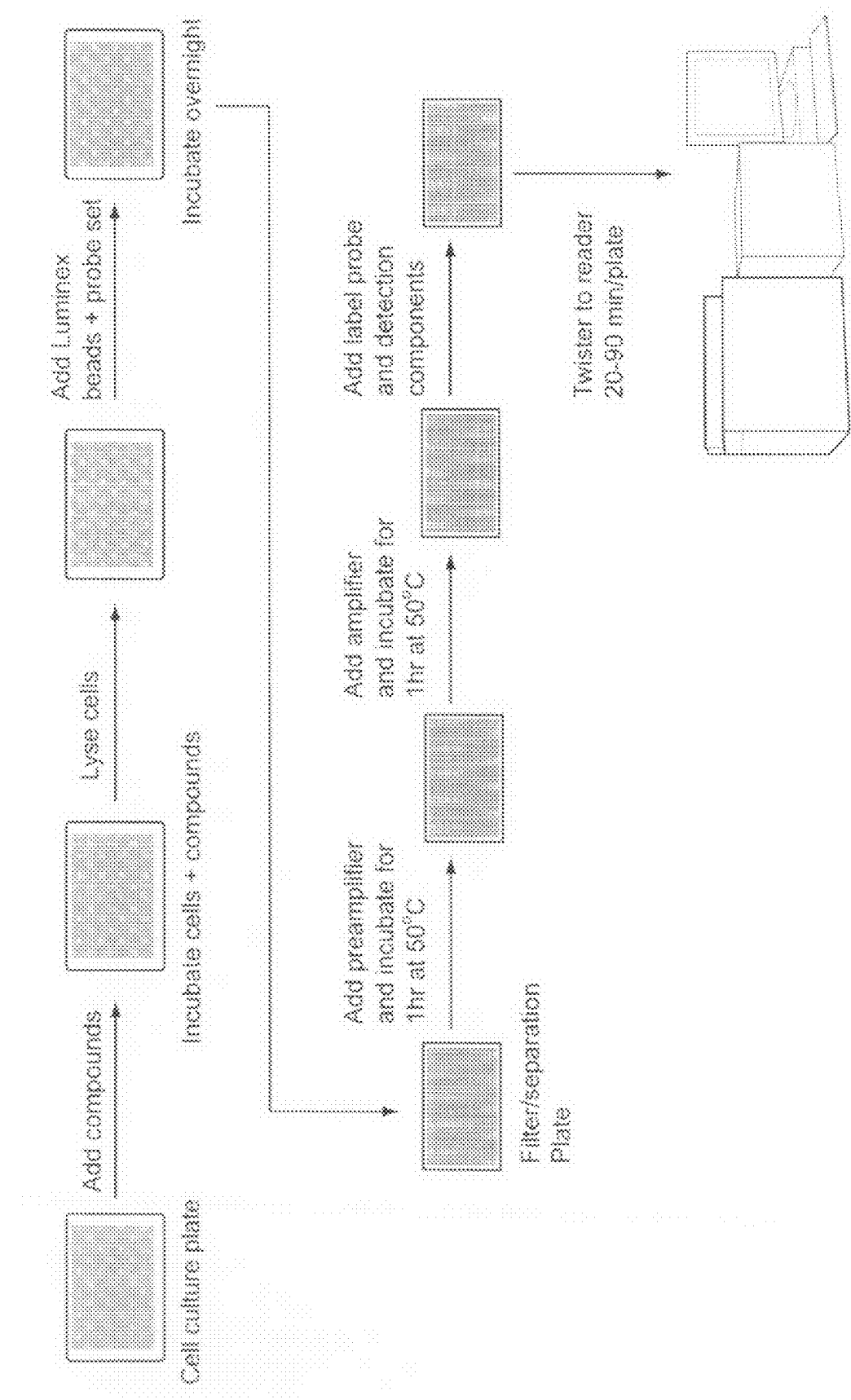
FIG. 4 Panel A schematically illustrates an exemplary workflow for a current multiplex bDNA assay. Panel B schematically illustrates a set of particles and associated capture probes for an exemplary 8×8 plex assay according to the present invention. Panels C-E schematically illustrate an exemplary workflow for an 8×8 multiplex bDNA assay of the present invention.
Figure 4B:
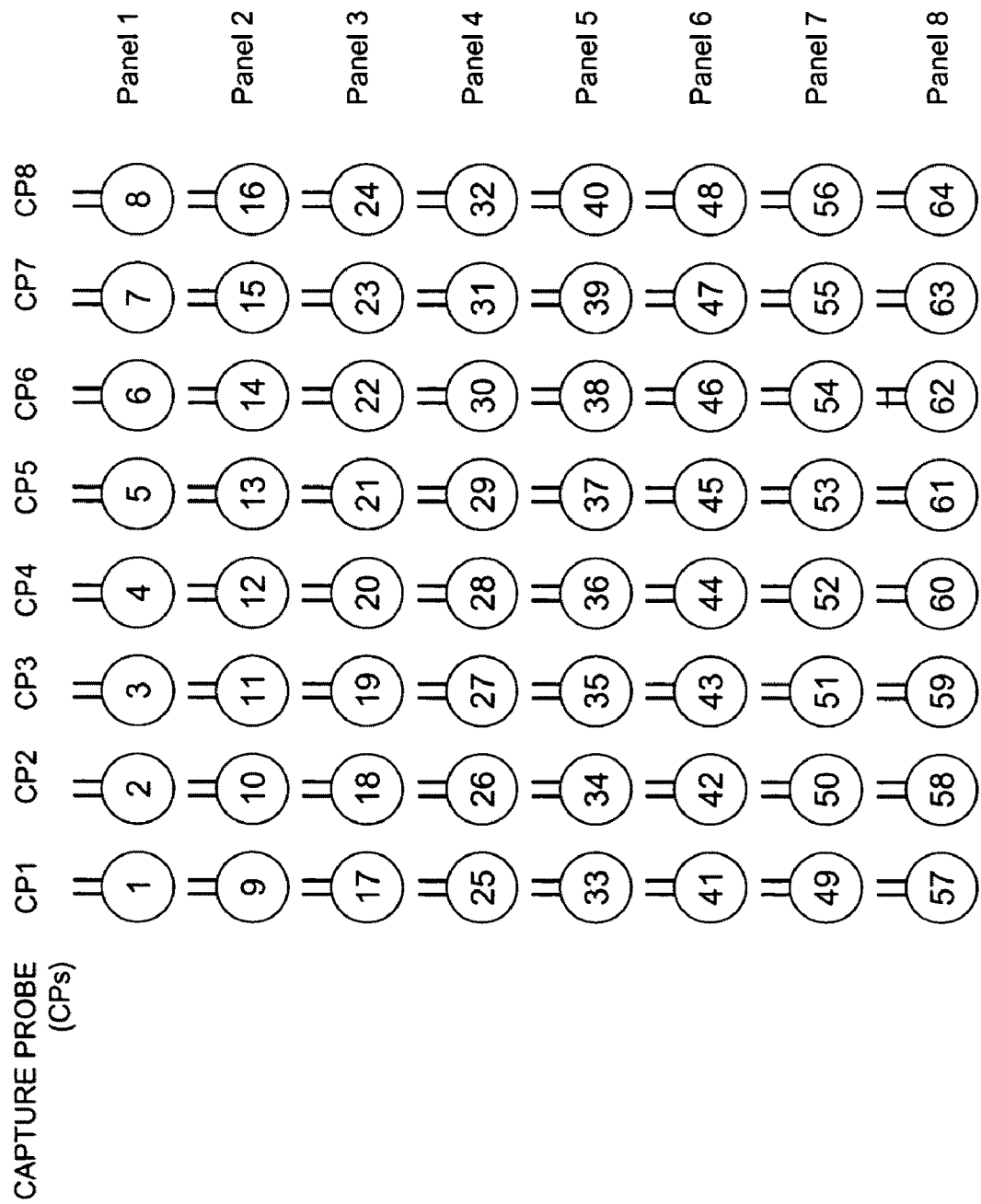
Figure 4C:
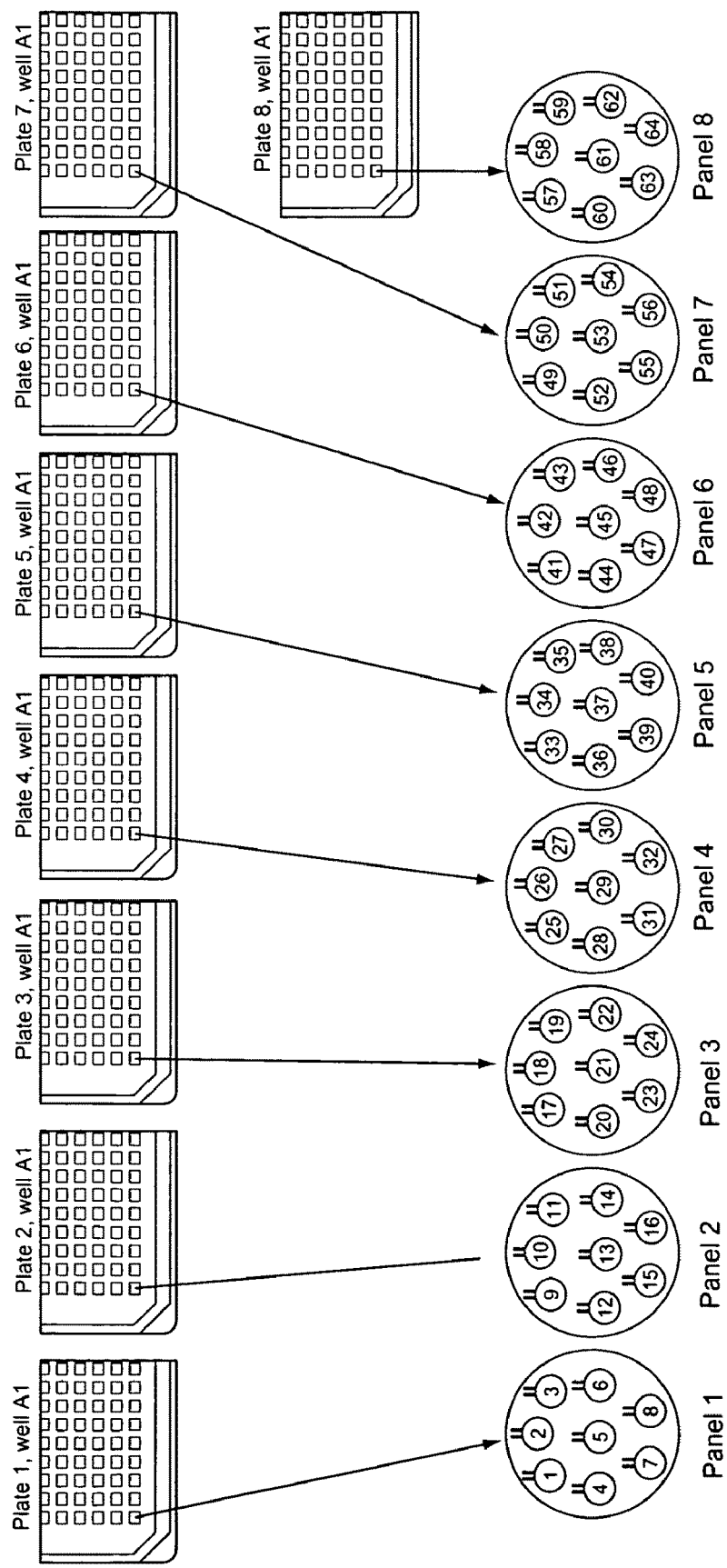
Figure 4D:
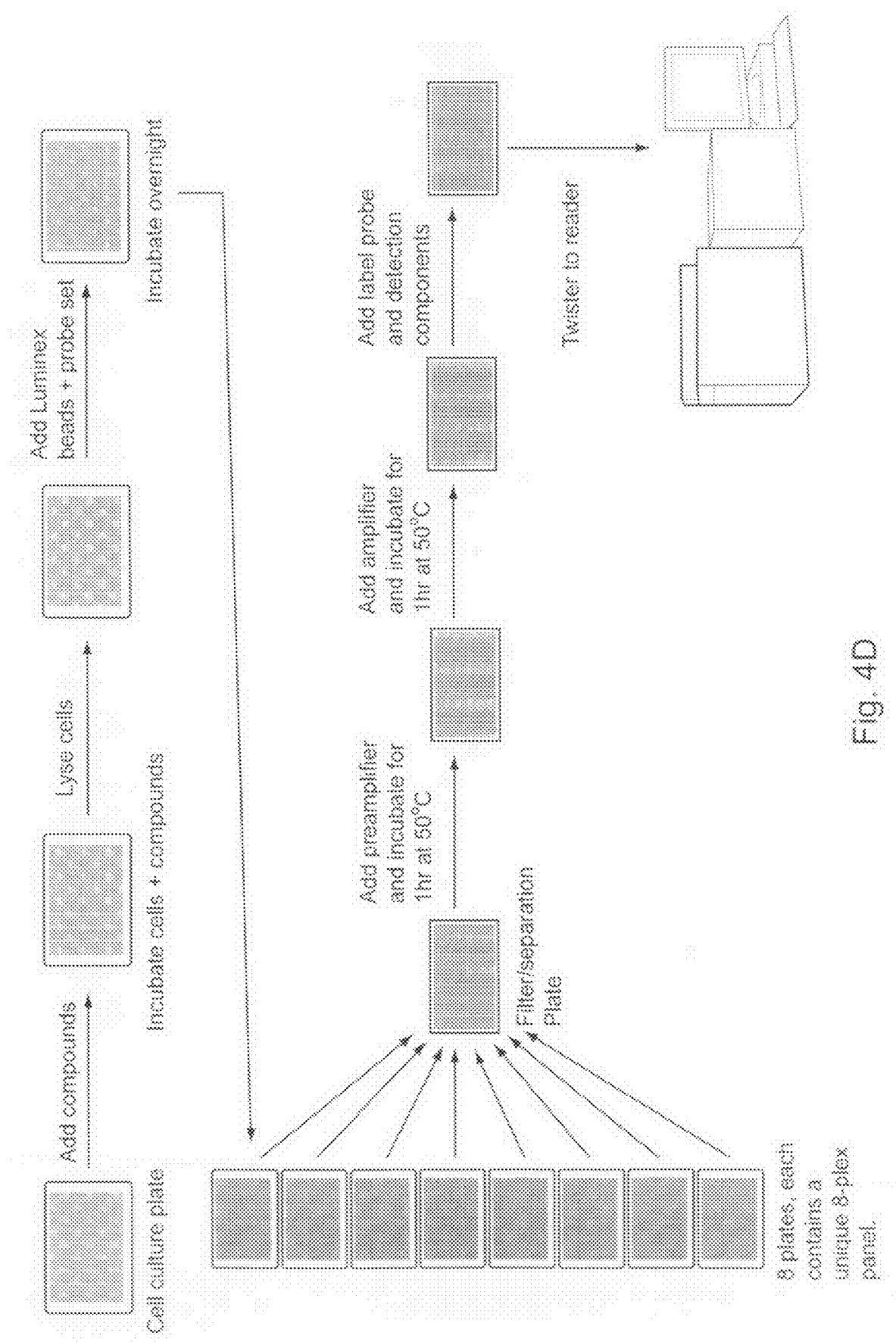
Figure 4E:
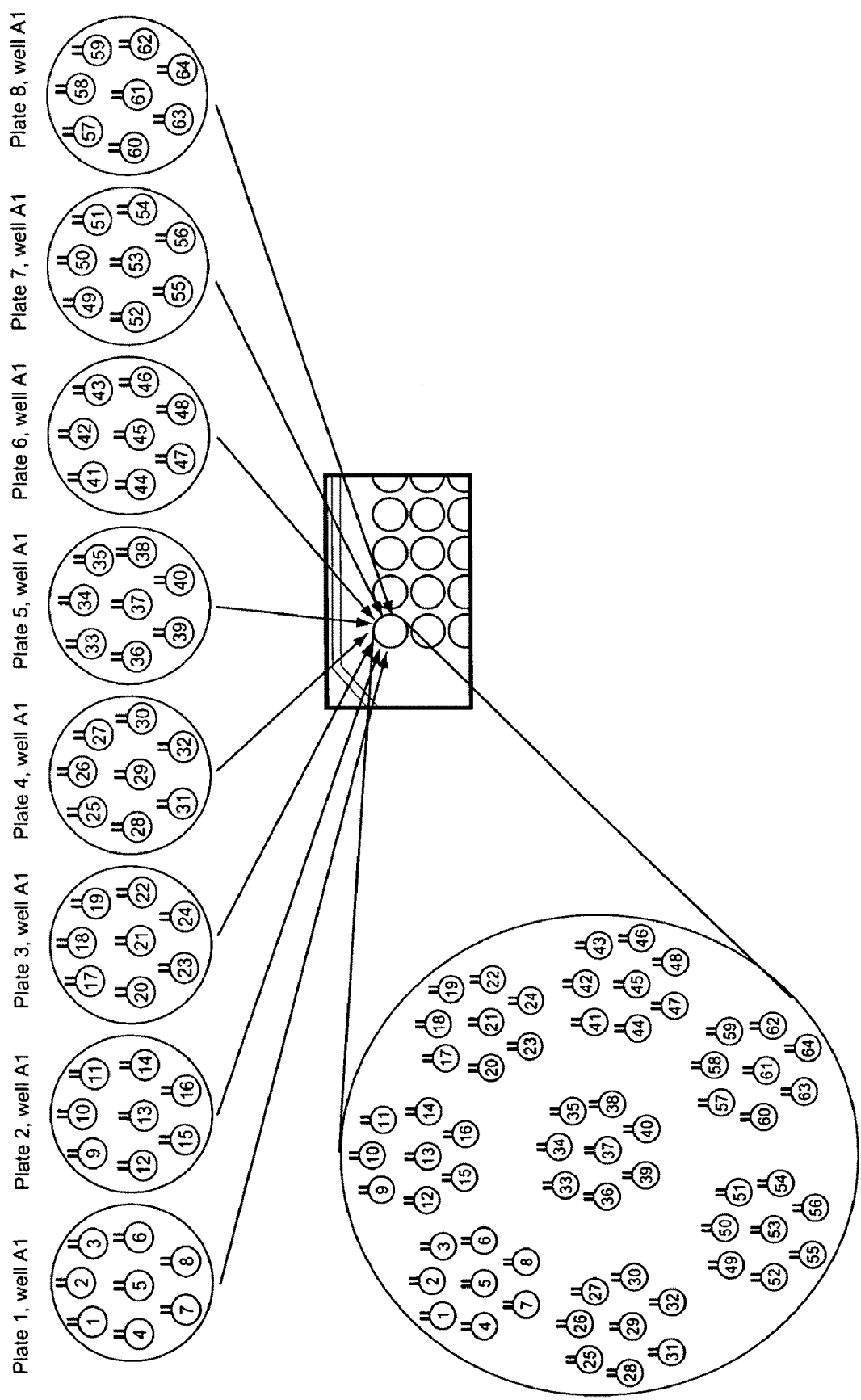

In FIG. 2, the same nucleic acid analytes are detected from two different samples. In contrast, FIG. 3 schematically illustrates the first few steps of an example in which different nucleic acid analytes are detected from two samples (which are optionally from identical or different sources). FIG. 3 Panel A illustrates two distinguishable subsets of microspheres 301 and 302, which have associated therewith capture probes 305 and 306, respectively. Each capture probe includes a sequence C-2 (350), which is different from subset to subset of microspheres. The two subsets of microspheres are mixed to form first pooled population 308 (Panel B). As shown in Panel C, a subset of three capture extenders is provided for each nucleic acid analyte of interest; subset 311 for nucleic acid 314 and subset 312 for nucleic acid 315. Each capture extender includes sequences C-1 (351, complementary to the respective capture probe's sequence C-2) and C-3 (352, complementary to a sequence in the corresponding nucleic acid of interest). Two subsets of label extenders (321 and 322 for nucleic acids 314 and 315, respectively) and two subsets of blocking probes (324 and 325 for nucleic acids 314 and 315, respectively) are also provided. Each label extender includes sequences L-1 (354, complementary to a sequence in the corresponding nucleic acid of interest) and L-2 (355, complementary to M-1).

As shown in Panel D, two additional distinguishable subsets of microspheres 303 and 304, which have associated therewith capture probes 305 and 306, respectively, are also provided. (Note that one capture probe is therefore present on both microspheres 301 and 303, while another capture probe is present on both microspheres 302 and 304.) The two subsets of microspheres are mixed to form second pooled population 309 (Panel E). In this example, however, nucleic acids 317 and 318 (not 314 and 315) are to be detected from the second sample. Therefore, as shown in Panel F, subset 366 of capture extenders is provided for nucleic acid analyte 317 and subset 367 for nucleic acid 318. Each capture extender includes sequences C-1 (351, complementary to the respective capture probe's sequence C-2) and C-3 (368, complementary to a sequence in the corresponding nucleic acid of interest). Two subsets of label extenders (361 and 362 for nucleic acids 317 and 318, respectively) and two subsets of blocking probes (364 and 365 for nucleic acids 317 and 318, respectively) are also provided. Each label extender includes sequences L-1 (363, complementary to a sequence in the corresponding nucleic acid of interest) and L-2 (355, complementary to M-1).

The remaining steps of the assay proceed basically as in the example illustrated in FIG. 2, with capture of the analytes through hybridization, addition of the label probe system, etc.

In embodiments in which different nucleic acid analytes are to be detected by different particle populations, the capture probes on the different populations are optionally different. Using the same set of capture probes on all the populations, as shown in FIG. 3, however, simplifies design of the assay; since only the target-specific ends of the capture extenders and label extenders need to be varied (i.e. sequences C-3 and L-1), only a limited number of C-1/C-2 sequence pairs must be designed and tested. This concept also simplifies probe design for multiplex bDNA assays (or other nucleic acid assays involving capture probes) in general; instead of having to design m·n C-1/C-2 sequence pairs to assay m·n nucleic acid targets, m panels of n targets can instead be assayed using the instant methods, requiring design of only n C-1/C-2 pairs. (For example, 64 target nucleic acids can be assayed using eight panels each of which detects eight targets by employing the same set of eight capture probes across all eight panels; see FIG. 4 Panel B.)

The methods of the invention offer additional advantages for multiplexing bDNA assays. FIG. 4 Panels A-E compare a conventional multiplex bDNA assay with a multiplex bDNA assay of the invention. Panel A illustrates a typical workflow for an exemplary conventional multiplex bDNA assay. Cells in a multiwell plate are optionally incubated with test compounds and then lysed. Microsphere and probe sets (CEs, LEs, and BPs) for each target nucleic acid are added and incubated overnight. The next day, the assay mixture is transferred to a filter plate, preamplifier, amplification multimer, and label probe are added, and the assay is read. Automated liquid and/or plate handling systems (e.g., Twister) can be employed to expedite performance of the assay, but readout is generally limited by the speed of the detector; a typical plate reader may take 20-90 minutes to read a 96-well plate or 2-4 hours to read a 384-well plate, for example. In contrast, Panels B-E illustrate a typical workflow for an exemplary bDNA assay using the instant methods. Panel B exemplifies an 8·8 format design, in which eight panels of eight microspheres each are employed. Each of the eight panels includes eight unique beads, each with one of eight zip code polynucleotide capture probes. Each panel uses the same set of eight capture probes, permitting the same C-1 capture extender ends to be used regardless of whether the same set of eight nucleic acids or different sets of eight nucleic acids are to be detected by the different panels. The total of 64 different microsphere sets can be differentiated, e.g., by their spectral signature. As shown in Panel C, the eight panels are initially handled in separate containers (e.g., a designated well or all the wells of different multiwell plates, where each plate contains a unique panel from 1-8); for example, as shown in Panel D, the microsphere subsets and probe sets (CEs, LEs, and BPs) for each of the eight nucleic acids for each panel of target nucleic acids are separately incubated overnight. (As noted above, if the nucleic acid target analytes are the same for the eight panels, the same probe sets can be employed; otherwise, different probe set mixtures are used.) The panels are then combined, such that all 64 microsphere sets are present in a single well (Panel E), and the preamplifier, amplification multimer, and label probe are added and the assay is read (Panel D). Combining the eight plates after the overnight hybridization into a single plate for processing the second day can be conveniently performed, e.g., with a high-throughput pipetting system. After combination, each well of the single filter/separation plate now contains eight eight-plex panels, for a total of 64 unique color-coded beads (or other distinguishable particles).

Advantages of this method (and related methods herein) include that it 1) reduces the number of plates processed in the second day (by eight-fold, in this example), 2) reduces read times by eight-fold, since only one plate is read instead of eight, 3) reduces cost of reagents, plates, labor, and equipment on the second day, which is significant since currently approximately 70% of reagent cost is incurred on the second day (this cost can be even greater with multiplex immunoassays), 4) requires less space, which is particularly significant when performing high throughput screening assays, and 5) improves inter-assay precision by processing eight first day incubated plates in a single plate on the second day of processing (e.g., in the four incubations and wash steps typical for the second day of processing).

Transcription Factor Assay

As yet another example, particle-based assays for activated transcription factors can be multiplexed using the methods of the invention. For example, oligonucleotide binding sites bound by transcription factors from each of two or more samples can be separated from sites not recognized by transcription factors in the samples, and the bound sites from all the samples can then be identified simultaneously using the methods of the invention, thereby indicating which active transcription factors were present in the original samples.

Accordingly, in one exemplary class of embodiments, the analytes are biotinylated nucleic acids, and the capture molecules are polynucleotides, each of which is complementary to one of the nucleic acid analytes. The first sample is provided by isolating a first group of one or more biotinylated nucleic acids bound by one or more transcription factors, and the second sample is similarly provided by isolating a second group of one or more biotinylated nucleic acids bound by one or more transcription factors. Analytes of the first or second group present in the first or second sample are captured on a selected subset of the first or second population of particles by hybridizing any biotinylated nucleic acid analyte present in the first or second sample to its complementary polynucleotide capture molecule, and which subsets of particles have an analyte of interest captured on the particles is detected by binding labeled streptavidin or labeled avidin to the biotinylated nucleic acid analytes, identifying at least a portion of the particles from each subset, and detecting the presence or absence of the label on those particles.

Figure 5:
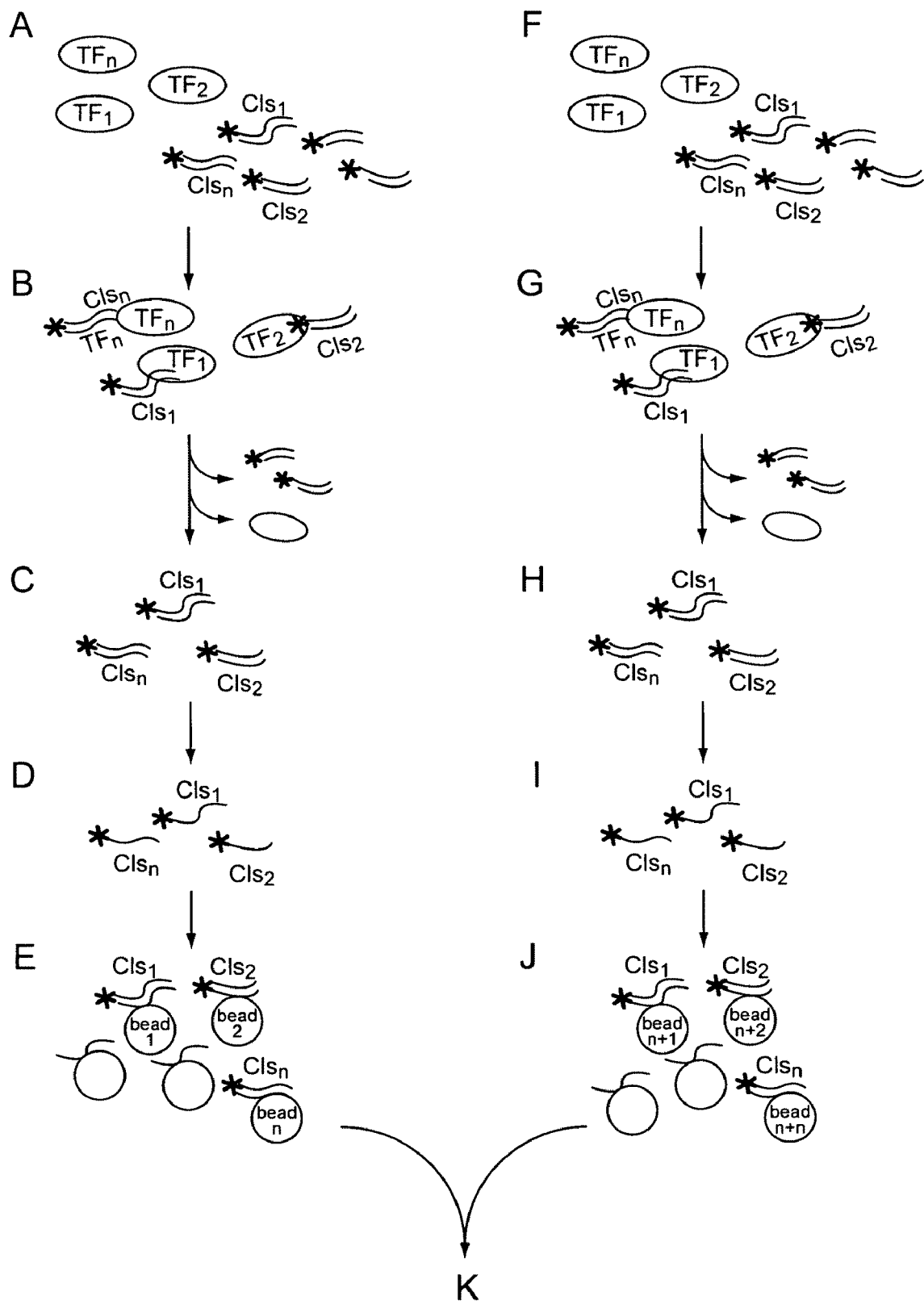
FIG. 5 Panels A-M schematically illustrate an assay in which transcription factor binding sites are identified by capture on particles bearing polynucleotide capture molecules.
Figure 5:
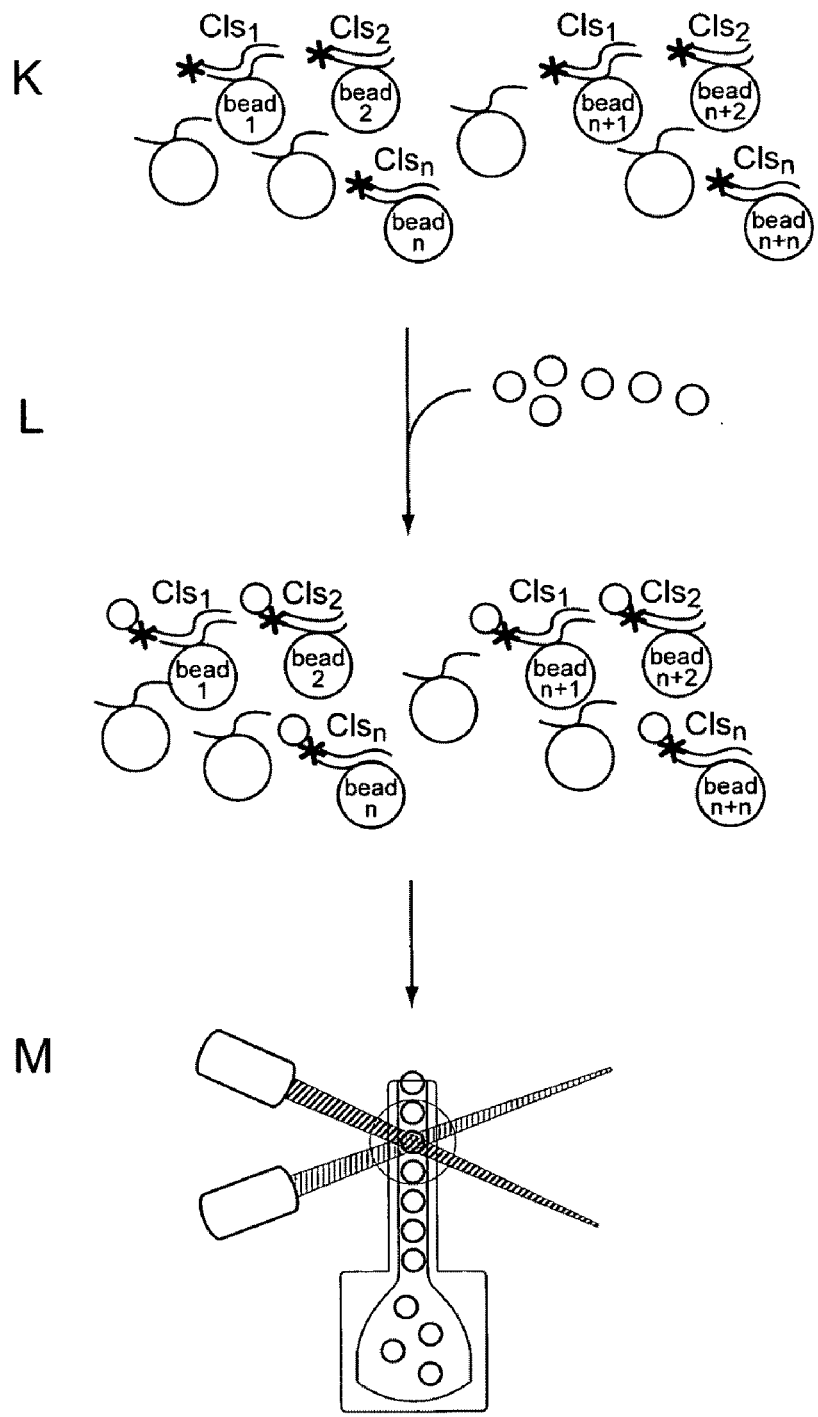

An exemplary embodiment in which the activation state of a set of transcription factors is detected in each of two samples is schematically illustrated in FIG. 5. The initial steps of the assay for one of the two samples are shown in FIG. 5 Panels A-E. As shown in Panel A, double-stranded oligonucleotide binding sites biotinylated on one strand (cis element probes, shown as $CIS_1$-$CIS_n$, with biotin represented by an asterisk) are incubated with a first sample comprising or suspected of comprising one or more activated transcription factors, e.g., with nuclear extract or whole cell lysate, e.g., in a 96 well plate or similar container. As shown in Panel B, active transcription factors present in the sample bind their respective sites. Probes bound by transcription factors are then separated from those not recognized by transcription factors, e.g., on a nitrocellulose plate or by differential mobility on an agarose gel; see U.S. Pat. No. 6,924,113 entitled "Method and kit for isolating DNA probes that bind to activated transcription factors" to Xianqiang Li. For example, when a separation plate is used, the transcription factor-probe mixture is transferred to the plate, and transcription factor-probe complexes are retained on the plate while unbound probes are washed away. The probes that were bound by transcription factors are then separated from the transcription factors, e.g., by denaturation (Panel C). Next the double-stranded probes are denatured, e.g., by heat, (Panel D) and the biotinylated strands are hybridized to complementary polynucleotide capture probes (Panel E). Each capture probe is present on a distinguishable subset of particles, e.g., fluorescently coded microspheres.

This first population of particles, with its captured biotinylated analytes, is then mixed with the other population(s), in this example, a second population produced by analogous operations performed on a second sample (FIG. 5 Panels F-J). The combined populations are shown in Panel K. To the combined populations of particles streptavidin-phycoerythrin (or a similar labeled biotin binding moiety, small circle) is added as the detection reagent (Panel L), and the assay is read (Panel M), e.g., in a flow cytometer or Luminex reader. Microspheres from each subset are identified, e.g., by their fluorescent emission spectrum, and the presence or absence of the label on each subset of microspheres is detected. Since each oligonucleotide binding site from a particular sample is associated with a distinct, preselected subset of microspheres, the presence of label on a given subset of microspheres correlates with the presence of the corresponding activated transcription factor in the original sample. As noted above, the assay is optionally quantitative.

Variations on the methods will be evident. For example, additional populations of particles may be employed to detect transcription factor activity in additional samples and/or different populations can bear different capture probes to detect different sets of transcription factor binding sites (from the same or different samples). As another example, the oligonucleotide binding sites can themselves be labeled (instead of biotinylated), obviating the need for a separate detection reagent, or a different detection reagent can be employed (e.g., anti-digoxigenin for digoxigenin-containing sites). In addition, analogous methods can be applied to detection of other nucleic acid binding proteins.

A nucleic acid binding site specific for a particular protein can comprise essentially any sequence and type of nucleic acid that can be recognized and specifically bound by that protein. For example, the nucleic acid binding site can comprise single-stranded DNA, double-stranded DNA, single-stranded RNA and/or double-stranded RNA, as appropriate for the particular protein (e.g., a single-stranded, double-stranded or hairpin DNA or RNA oligonucleotide comprising a binding site for the protein). Appropriate binding sites for many proteins (particularly sequence-specific double-stranded DNA binding proteins) have been described in the literature, and an appropriate binding site can be determined for any sequence-specific nucleic acid binding protein by methods known in the art. For example, gel mobility shift assays and/or chemical or DNase footprinting can be used to identify a physiologically relevant binding site, or binding site selection can be performed to select a consensus high affinity binding site. See, e.g., Sambrook (infra), Ausubel (infra), Kosugi and Ohashi (2002) Plant J 30:337-348, Johannesson et al. (2001) Plant Mol Biol 45:63-73, Steadman et al. (2000) Nucleic Acids Res 28:2389-95, and Wolfe et al. (1999) J Mol Biol 285: 1917-34.

The polynucleotide capture probe (or, in other aspects in which nucleic acid binding proteins are captured to particles through binding to capture molecules themselves comprising nucleic acid binding sites, the nucleic acid binding sites) can be covalently or noncovalently associated with the particles, as described in greater detail in the "Microspheres and Other Particles" section below. For example, an oligonucleotide comprising a free amino group (introduced during synthesis) can be covalently coupled to carboxylate-modified particles via a carbodiimide coupling method, or a biotinylated nucleic acid can be noncovalently associated with streptavidin-modified particles.

Tyrosine-Phosphorylated Polypeptide/SH2 Assay

In another exemplary class of embodiments, the analytes are tyrosine-phosphorylated polypeptides, and the capture molecules comprise (e.g., are) SH2 domains. Which subsets of particles have an analyte of interest captured on the particles can be detected by, for example, i) binding a biotinylated anti-phosphotyrosine antibody to any tyrosine-phosphorylated polypeptide analyte captured on the particles, and binding labeled streptavidin or labeled avidin to the biotinylated anti-phosphotyrosine antibody, ii) identifying at least a portion of the particles from each subset, and iii) detecting the presence or absence of the label on those particles.

Figure 6:
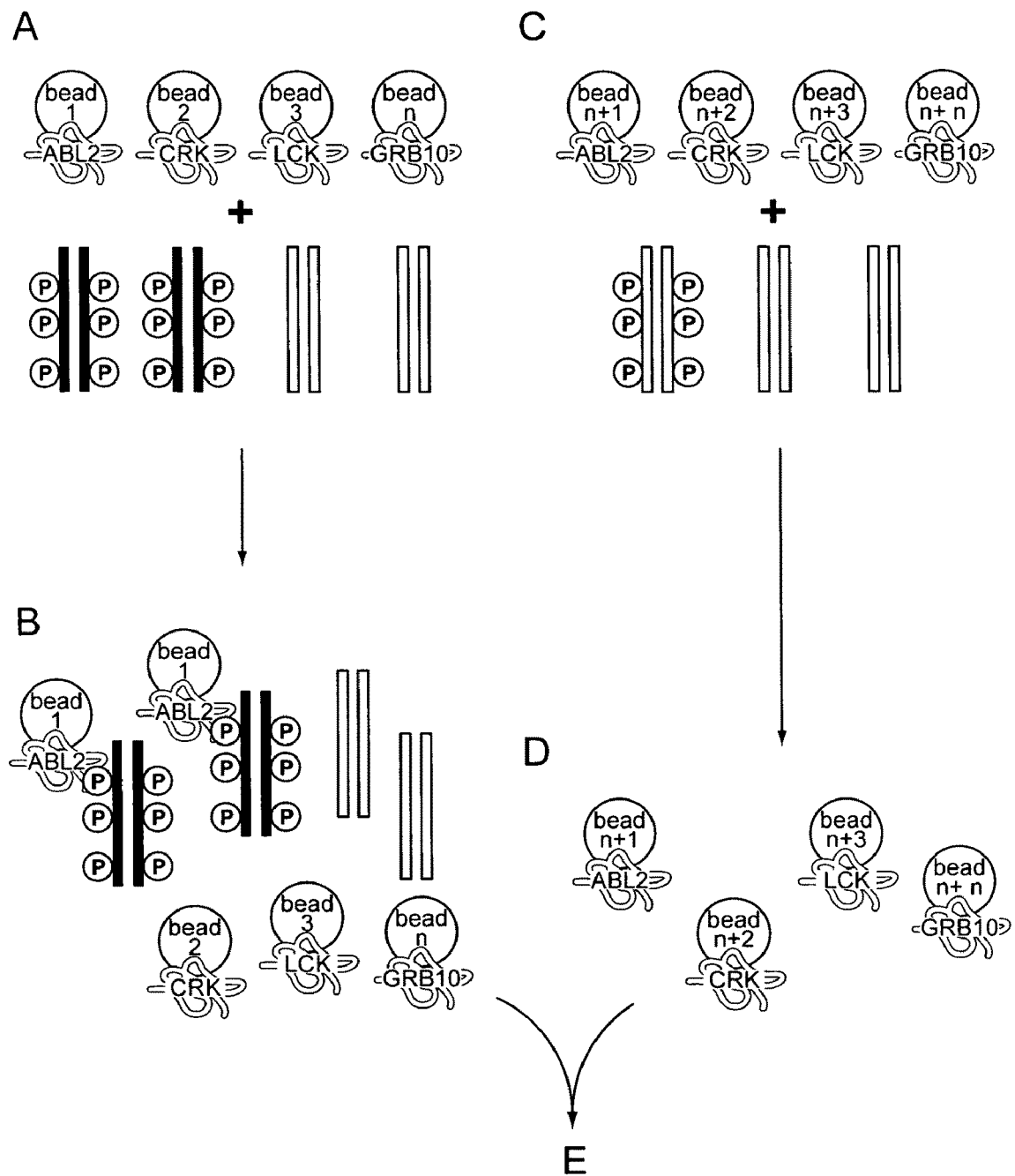
FIG. 6 Panels A-G schematically illustrate an assay in which tyrosine-phosphorylated polypeptides are detected by capture on particles having SH2 capture molecules.
Figure 6:
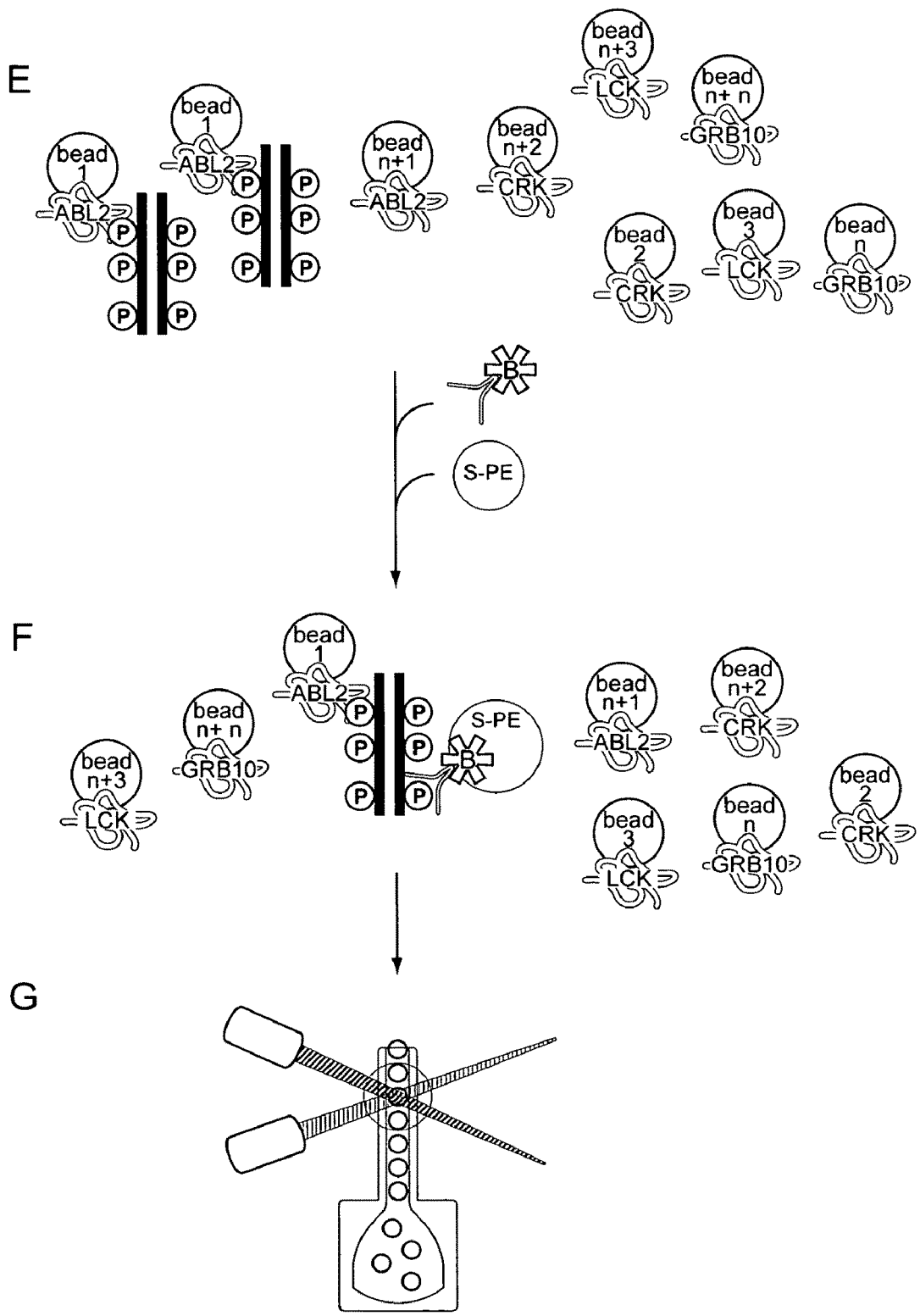

An exemplary embodiment is schematically illustrated in FIG. 6 for two populations of particles. (See also Yaoi et al. (2006) "Src Homology 2 Domain-based High Throughput Assays for Profiling Downstream Molecules in Receptor Tyrosine Kinase Pathways" Molecular & Cellular Proteomics 5.5 959-968 for description of related singleplex assays.) The initial steps of the assay for one of two samples and populations of particles are illustrated in FIG. 6 Panels A-B. As shown in Panel A, a first population of microspheres is provided, where each distinguishable subset of microspheres has a different SH2 domain conjugated to its surface. The first population is contacted with a first sample (e.g., a treated cell lysate) comprising or suspected of comprising tyrosine-phosphorylated (P) polypeptides. As shown in Panel B, each of the tyrosine-phosphorylated polypeptides is captured by its corresponding SH2 domain to a selected subset of microspheres. The first population, with bound polypeptides, is then mixed with the second population also comprising bound tyrosine-phosphorylated polypeptides, e.g., from untreated cell lysate for comparison, produced by analogous operations on a second sample as schematically illustrated in Panels C-D. The combined populations are shown in Panel E. Proteins not captured on the microspheres are removed, for example, by washing before or after combination of the populations. A biotin-conjugated (B) anti-phosphotyrosine antibody and then a streptavidin-phycoerythrin detection reagent (S-PE, or similar labeled biotin binding moiety) are added (Panel F), and the assay is read (Panel G), e.g., in a flow cytometer or Luminex reader. Microspheres from each subset are identified, e.g., by their fluorescent emission spectrum, and the presence or absence of the label on each subset of microspheres is detected. Since each tyrosine-phosphorylated polypeptide from a particular sample is associated with a distinct, preselected subset of microspheres, the presence of label on a given subset of microspheres correlates with the presence of the corresponding tyrosine-phosphorylated polypeptide in that original sample. Beads that do not have any bound phosphotyrosine proteins will have little or no label (e.g., PE) fluorescence. As noted above, the assay is optionally quantitative.

This class of embodiments is conceptually similar to the immunoassays described above, except that the analytes are captured to the particles by SH2 domains rather than by antibodies. Thus, as for the immunoassay embodiments above, a number of variations on this example will immediately be evident. For example, the detection antibody can itself comprise a label instead of being biotinylated and indirectly capturing a label, a labeled secondary antibody can be bound to the detection antibody, or a biotinylated secondary antibody can be bound to the detection antibody and then detected with labeled streptavidin. Additional analytes can be detected from one or both samples by including additional microsphere subsets with appropriate SH2 capture molecules in the first and/or second populations; the additional analytes can be detected with the same detection antibody if they share a common epitope, or with additional detection antibodies if not. Different analytes can be detected from the different samples. Additional microsphere populations, including the same or different capture molecules, can be included to detect analytes from additional samples. In these (and other embodiments described herein), SH2 domains, rather than antibodies, are optionally employed as detection reagents for tyrosine-phosphorylated polypeptides. In addition, it will be evident that other protein binding domains can be used as capture molecules and/or detection reagents in similar assays, e.g., PTB domains for tyrosine-phosphorylated polypeptides, SH3 domains for proline rich polypeptides, 14-3-3 domains for serine-phosphorylated polypeptides, chromodomains for lysine-methylated polypeptides, and bromodomains for lysine-acetylated polypeptides. Combinations of domains (e.g., different domains on different subsets or populations) can also be employed. Essentially any of the hundreds of known protein interaction domains can be employed, not just SH2 domains. Thus, in one class of embodiments, the capture molecules comprise protein interaction domains (protein domains that mediate protein-protein interactions).

SH2 domains are one of the many protein domain families that mediate protein-protein interactions in signal transduction. These domains, which are generally defined by a conserved region of approximately 100 amino acid residues, specifically recognize and bind to phosphotyrosine-containing ligands. SH2 domains can be found in enzymes, adaptor proteins, regulatory subunits of signaling proteins, scaffold proteins, transcription factors and oncogenic proteins, for example. Examples include, but are not limited to, the 3BP2, NSP1, ABL2, GRB2, BTK, P55G-D1, GRAP, P85A-D1, CRK, P85A-D2, CRKL, P85B-D1, DAPP1, P85B-D2, FYN, PLCG1-D1, GRB10, PTPN11-D2, GRB14, PTPN6-D2, CSK, SOCS2, VAV3, STAP2, LCK, SYK-D2, LCP2, TNS, MATK, and SHC1 SH2 domains.

SH2 domains, as well as other polypeptide binding domains such as the PTB, SH3, 14-3-3, chromo- and bromo-domains noted above, have been well described in the literature. For example, the specificity of various SH2 domains for sequences surrounding the phosphorylated tyrosine residue has been determined. See, e.g., a list of phosphopeptide binding domains at folding (dot) cchmc (dot) org/online/SEPdomaindatabase (dot) htm; a list of protein interaction domains at pawsonlab (dot) mshri (dot) on (dot) ca/index.php?option=com_content&task=view&id=30&Itemid=68; a list of protein domains at www (dot) cellsignal (dot) com/reference/domain/index (dot) asp, which includes consensus binding sites, exemplary peptide ligands, and exemplary binding partners, e.g., for SH-2, 14-3-3, PTB, and WW domains; Kuriyan and Cowburn (1997) "Modular peptide recognition domains in eukaryotic signaling" Annu. Rev. Biophys. Biomol. Struct. 26:259-288; Sharma et al. (2002) "Protein-protein interactions: Lessons learned" Curr. Med. Chem.—Anti-Cancer Agents 2:311-330; Pawson et al. (2001) "SH2 domains, interaction modules and cellular wiring" Trends Cell Biol. 11:504-11; Forman-Kay and Pawson (1999) "Diversity in protein recognition by PTB domains" Curr Opin Struct Biol. 9:690-5; and Fu et al. (2000) "14-3-3 Proteins: Structure, Function, and Regulation" Annual Review of Pharmacology and Toxicology 40:617-647. A large number of such domains from a variety of different proteins have been described, and others can readily be identified, e.g., through sequence alignment, structural comparison, and similar techniques, as is well known in the art. Common sequence repositories for known proteins include GenBank and Swiss-Prot, and other repositories can easily be identified by searching the internet. Similarly, antibodies against phosphotyrosine, phosphoserine, phosphothreonine and/or other posttranslational modifications are well known in the art; many are commercially available, and others can be generated by established techniques.

Compositions, Kits and Systems

Compositions, kits, and systems related to, produced by, or of use in the methods are another feature of the invention. For example, one general class of embodiments provides a composition that includes a mixture of at least a first population of particles and a second population of particles. The first population of particles includes one or more subsets of particles. In embodiments in which the population comprises two or more subsets, a plurality of the particles in each subset are distinguishable from a plurality of the particles in the other subsets. The particles in each subset comprise a capture molecule. In embodiments in which the first population comprises two or more subsets of particles, the capture molecule on each subset is typically different from those on the other subsets of the first population; each subset of particles can thus capture a different, predetermined analyte. Similarly, the second population of particles also includes one or more subsets of particles. A plurality of the particles in each subset of the second population are distinguishable from a plurality of the particles in the subsets of the first population. In addition, in embodiments in which the second population comprises two or more subsets, a plurality of the particles in each subset of the second population are distinguishable from a plurality of the particles in the other subsets of the second population. The particles in each subset of the second population comprise a capture molecule. In embodiments in which the second population comprises two or more subsets of particles, the capture molecule on each subset of the second population is typically different from those on the other subsets of the second population.

As noted, the subsets of the first population comprise different capture molecules from each other, and the subsets of the second population likewise comprise different capture molecules from other subsets of the second population. In some embodiments, subsets of the first and second populations comprise different capture molecules from each other as well. In other embodiments, however, there is overlap between the capture molecules on one or more subsets of the first and second populations. Thus, in one class of embodiments, the capture molecule on a subset of the particles of the second population is substantially identical to the capture molecule on a subset of the first population. Optionally, the capture molecules on each of the two or more subsets of the particles in the second population are substantially identical to the capture molecules on subsets of the first population.

Optionally, analytes originating from a first sample are captured on (i.e., directly or indirectly bound to) the particles of the first population (e.g., one analyte per particle subset) while analytes originating from a second sample are captured on the particles of the second population.

A related general class of embodiments provides a composition that includes a first group of one or more analytes, which analytes originate from (e.g., were captured from) a first sample, a second group of one or more analytes, which analytes originate from a second sample different from the first sample, and a mixture of at least a first population of particles and a second population of particles. The first population of particles includes one or more subsets of particles. In embodiments in which the population comprises two or more subsets, a plurality of the particles in each subset are distinguishable from a plurality of the particles in the other subsets. The particles in each subset comprise a capture molecule, which capture molecule is configured to capture one of the analytes of the first group. In embodiments in which the first population comprises two or more subsets of particles, the capture molecule on each subset is typically different from those on the other subsets of the first population; each subset of particles can thus capture a different, predetermined analyte. Similarly, the second population of particles also includes one or more subsets of particles. A plurality of the particles in each subset of the second population are distinguishable from a plurality of the particles in the subsets of the first population. In addition, in embodiments in which the second population comprises two or more subsets, a plurality of the particles in each subset of the second population are distinguishable from a plurality of the particles in the other subsets of the second population. The particles in each subset of the second population comprise a capture molecule, which capture molecule is configured to capture one of the analytes of the second group. In embodiments in which the second population comprises two or more subsets of particles, the capture molecule on each subset of the second population is typically different from those on the other subsets of the second population. Generally, the analytes of the first group are captured on (i.e., directly or indirectly bound to) the particles of the first population (e.g., one analyte per particle subset) while the analytes of the second group are captured on the particles of the second population.

Essentially all of the features noted for the methods above apply to the composition embodiments as well, as relevant; for example, with respect to number of analytes, groups of analytes, subsets of particles per population, and/or particle populations, type of analytes, source of the samples, type of capture molecules, inclusion of detection reagent, and/or the like. Thus, for example, the composition optionally includes three or more, five or more, 10 or more, 20 or more, 30 or more, 40 or more, 50 or more, or even 100 or more populations of particles, and each population optionally includes two or more, three or more, five or more, 10 or more, 20 or more, 30 or more, 40 or more, 50 or more, or even 100 or more distinguishable subsets of particles.

Another general class of embodiments provides a composition comprising a first group of one or more analytes, which analytes originate from a first sample, a second group of one or more analytes, which analytes originate from a second sample different from the first sample, and a mixture of at least a first set of reporter entities and a second set of reporter entities. The first set of reporter entities includes one or more reporter entities, each of which is configured to capture a different one of the analytes of the first group. In embodiments in which the first set comprises two or more reporter entities, the reporter entities are distinguishable from each other. Similarly, the second set of reporter entities also comprises one or more reporter entities, each of which is configured to capture a different one of the analytes of the second group. The reporter entities of the second set are distinguishable from those of the first set. In embodiments in which the second set comprises two or more reporter entities, the reporter entities of the second set are distinguishable from each other. Generally, the analytes of the first group are captured to (i.e., indirectly or directly bound to) the reporter entities of the first set (e.g., one type of analyte per entity), while the analytes of the second group are captured to the reporter entities of the second set.

Essentially all of the features noted for the embodiments above apply to these embodiments as well, as relevant; for example, with respect to number of analytes per group, groups of analytes, sets of reporter entities, and/or reporter entities per set, type of analytes and/or reporter entities, source of the samples, inclusion of detection reagent, and/or the like. As for the embodiments above, the analytes of the first and second groups can be the same target molecules from different sources or they can be different target molecules; accordingly, the reporter entities of the first and second sets can be configured to capture the same or different analytes (or a combination thereof).

Another group of embodiments provide a composition that includes a mixture of at least a first set of reporter entities and a second set of reporter entities. The first set of reporter entities includes one or more entities. In embodiments in which the first set comprises two or more reporter entities, the reporter entities are distinguishable from each other, and each of the entities is configured to capture a different analyte from a first group of analytes. Similarly, the second set of reporter entities also includes one or more entities. The reporter entities of the second set are distinguishable from those of the first set. In addition, in embodiments in which the second set comprises two or more reporter entities, the reporter entities of the second set are distinguishable from each other, and each of the entities is configured to capture a different analyte from a second group of analytes. The entities of the first and second sets can be configured to capture different groups of analytes (i.e., the first and second groups of analytes are not the same), or the entities of the first and second sets can be configured to capture the same analytes (i.e., the first and second groups of analytes are the same), or a combination thereof. Optionally, analytes originating from a first sample are captured to (i.e., directly or indirectly bound to) the entities of the first set while analytes originating from a second sample are captured on the entities of the second set. Again, essentially all of the features noted for the embodiments above apply to these embodiments as well, as relevant.

Yet another general class of embodiments provides a kit for detecting analytes of interest. The kit includes first and second (and optionally third, fourth, etc) populations of particles comprising capture molecules, as described above, packaged in one or more containers. The kit optionally also includes instructions for using the kit to capture and detect the analytes, at least one detection reagent, one or more buffered solutions (e.g., lysis buffer, diluent, hybridization buffer, and/or wash buffer), standards comprising one or more analytes at known concentration, and/or the like. Essentially all of the features noted for the methods above apply to the kits as well, as relevant; for example, with respect to number of analytes to be detected, groups of analytes, subsets of particles per population, and/or particle populations, type of analytes, source of the samples, type of capture molecules, type of detection reagent, and/or the like.

Another general class of embodiments also provides a kit for detecting analytes of interest. The kit includes first and second (and optionally third, fourth, etc) sets of reporter entities, as described above, packaged in one or more containers. The kit optionally also includes instructions for using the kit to capture and detect the analytes, at least one detection reagent, one or more buffered solutions (e.g., lysis buffer, diluent, hybridization buffer, and/or wash buffer), standards comprising one or more analytes at known concentration, and/or the like. Essentially all of the features noted for the methods above apply to the kits as well, as relevant; for example, with respect to number of analytes per group, groups of analytes, sets of reporter entities, and/or reporter entities per set, type of analytes and/or reporter entities, source of the samples, type of detection reagent, and/or the like.

In one aspect, the invention includes systems, e.g., systems used to practice the methods herein and/or comprising the compositions described herein, optionally in high-throughput mode. The system can include, e.g., a fluid and/or particle handling element, a fluid and/or particle containing element, a laser for exciting a fluorescent label and/or fluorescent particles, a detector for detecting light emissions from a chemiluminescent reaction or fluorescent emissions from a fluorescent label and/or fluorescent particles, and/or a robotic element that moves other components of the system from place to place as needed (e.g., a multiwell plate handling element). For example, in one class of embodiments, a composition of the invention is contained in a flow cytometer, a Luminex 100™ or HTS™ instrument, a BeadXpress™ instrument, a microplate reader, or like instrument.

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or laser). The computer can also receive data from other components of the system, e.g., from a detector, and can interpret the data, provide it to a user in a human readable format, or use that data to initiate further operations, in accordance with any programming by the user.

Labels

A wide variety of labels are well known in the art and can be adapted to the practice of the present invention. For example, luminescent labels and light-scattering labels (e.g., colloidal gold particles) have been described. See, e.g., Csaki et al. (2002) "Gold nanoparticles as novel label for DNA diagnostics" Expert Rev Mol Diagn 2:187-93. As noted above, fluorescent labels are typically preferred, however, for ease of detection.

A number of fluorescent labels are well known in the art, including but not limited to, hydrophobic fluorophores (e.g., phycoerythrin, rhodamine, Alexa Fluor 488 and fluorescein), green fluorescent protein (GFP) and variants thereof (e.g., cyan fluorescent protein and yellow fluorescent protein), and quantum dots. See e.g., Haughland (2003) Handbook of Fluorescent Probes and Research Products, Ninth Edition or Web Edition, from Molecular Probes, Inc., or The Handbook: A Guide to Fluorescent Probes and Labeling Technologies, Tenth Edition or Web Edition (2006) from Invitrogen (available on the world wide web at probes (dot) invitrogen (dot) com/handbook) for descriptions of fluorophores emitting at various different wavelengths (including tandem conjugates of fluorophores that can facilitate simultaneous excitation and detection of multiple labeled species). For use of quantum dots as labels for biomolecules, see e.g., Dubertret et al. (2002) Science 298:1759; Nature Biotechnology (2003) 21:41-46; and Nature Biotechnology (2003) 21:47-51.

Labels can be introduced to molecules, e.g. polypeptides, polynucleotides, or small molecules, during synthesis or by postsynthetic reactions by techniques established in the art. For example, kits for fluorescently labeling proteins, antibodies, and polynucleotides with various fluorophores are available from Invitrogen Corp. (probes (dot) invitrogen (dot) com), and fluorophore-containing phosphoramidites for use in nucleic acid synthesis are commercially available. Similarly, signals from the labels (e.g., absorption by and/or fluorescent emission from a fluorescent label) can be detected by essentially any method known in the art. For example, multicolor detection, detection of FRET, fluorescence polarization, and the like, are well known in the art.

Microspheres and Other Particles

Microspheres are preferred particles in certain embodiments described herein since they are generally stable, are widely available in a range of materials, surface chemistries, and uniform sizes, and can be fluorescently dyed. Microspheres can be distinguished from each other by identifying characteristics such as their size (diameter) and/or their fluorescent emission spectra, for example.

Luminex Corporation (www (dot) luminexcorp (dot) com), for example, currently offers 100 sets of uniform diameter polystyrene microspheres and plans to offer additional sets. The microspheres of each set are internally labeled with a distinct ratio of two or more fluorophores. A flow cytometer or other suitable instrument can thus be used to classify each individual microsphere according to its predefined fluorescent emission ratio. Fluorescently-coded microsphere sets are also available from a number of other suppliers, including Radix Biosolutions (www (dot) radixbiosolutions (dot) com) and Upstate Biotechnology (www (dot) upstatebiotech (dot) com). Alternatively, Beckman Coulter (www (dot) beckmancoulter (dot) com), BD Biosciences (www (dot) bd (dot) com) and Bangs Laboratories, Inc. (www (dot) bangslabs (dot) com) offer microsphere sets distinguishable by a combination of fluorescence and size. As another example, microspheres can be distinguished on the basis of size alone, but fewer sets of such microspheres can be multiplexed in an assay because aggregates of smaller microspheres can be difficult to distinguish from larger microspheres.

Microspheres with a variety of surface chemistries are commercially available, from the above suppliers and others (e.g., see additional suppliers listed in Kellar and Iannone (2002) "Multiplexed microsphere-based flow cytometric assays" Experimental Hematology 30:1227-1237 and Fitzgerald (2001) "Assays by the score" The Scientist 15[11]: 25). For example, microspheres with carboxyl, hydrazide or maleimide groups are available and permit covalent coupling of molecules (e.g., capture molecules with free amine, carboxyl, aldehyde, sulfhydryl or other reactive groups) to the microspheres; a capture molecule can, e.g., be covalently coupled to carboxylate-modified particles via a carbodiimide coupling method or to maleimide-modified particles via a thiol-maleimide interaction. As another example, microspheres with surface avidin or streptavidin are available and can bind biotinylated capture molecules; similarly, microspheres coated with biotin are available for binding capture molecules conjugated to avidin or streptavidin. Microspheres coated with anti-species antibodies (e.g., with anti-mouse IgG), protein A, and protein G are available for binding antibody capture molecules. Microspheres coated with $Ni^{2+}$ or glutathione are available and permit binding of polyhistidine-tagged or GST-tagged recombinant polypeptides used as capture molecules, respectively. In addition, services that couple capture molecules of the customer's choice to microspheres are commercially available, e.g., from Radix Biosolutions (www (dot) radixbiosolutions (dot) com).

Protocols for using such commercially available microspheres (e.g., methods of covalently coupling proteins and nucleic acids to carboxylated microspheres for use as capture molecules, methods of blocking reactive sites on the microsphere surface that are not occupied by the capture molecules, methods of binding biotinylated capture molecules to avidin-functionalized microspheres, and the like) are typically supplied with the microspheres and are readily utilized and/or adapted by one of skill. In addition, coupling of reagents to microspheres is well described in the literature. For example, see Yang et al. (2001) "BADGE, Beads Array for the Detection of Gene Expression, a high-throughput diagnostic bioassay" Genome Res. 11:1888-98; Fulton et al. (1997) "Advanced multiplexed analysis with the FlowMetrix™ system" Clinical Chemistry 43:1749-1756; Jones et al. (2002) "Multiplex assay for detection of strain-specific antibodies against the two variable regions of the G protein of respiratory syncytial virus" 9:633-638; Camilla et al. (2001) "Flow cytometric microsphere-based immunoassay: Analysis of secreted cytokines in whole-blood samples from asthmatics" Clinical and Diagnostic Laboratory Immunology 8:776-784; Martins (2002) "Development of internal controls for the Luminex instrument as part of a multiplexed seven-analyte viral respiratory antibody profile" Clinical and Diagnostic Laboratory Immunology 9:41-45; Kellar and Iannone (2002) "Multiplexed microsphere-based flow cytometric assays" Experimental Hematology 30:1227-1237; Oliver et al. (1998) "Multiplexed analysis of human cytokines by use of the Flow-Metrix system" Clinical Chemistry 44:2057-2060; Gordon and McDade (1997) "Multiplexed quantification of human IgG, IgA, and IgM with the FlowMetrix system" Clinical Chemistry 43:1799-1801; U.S. Pat. No. 5,981,180 entitled "Multiplexed analysis of clinical specimens apparatus and methods" to Chandler et al. (Nov. 9, 1999); U.S. Pat. No.

6,449,562 entitled "Multiplexed analysis of clinical specimens apparatus and methods" to Chandler et al. (Sep. 10, 2002); and references therein.

Methods of binding analytes to capture molecules coupled to microspheres are also described in the above references, as are methods for producing and using detection reagents. Methods of analyzing microsphere populations (e.g. methods of identifying microsphere subsets by their size and/or fluorescence characteristics, methods of using size to distinguish microsphere aggregates from single uniformly sized microspheres and eliminate aggregates from the analysis, methods of detecting the presence or absence of a fluorescent label on the microsphere subset, and the like) are also well described in the literature. See, e.g., the above references.

Suitable instruments, software, and the like for analyzing microsphere populations to distinguish subsets of microspheres and to detect the presence or absence of a label (e.g., a fluorescently labeled analyte or detection reagent) on each subset are commercially available. For example, flow cytometers are widely available, e.g., from Becton-Dickinson (www (dot) bd (dot) com) and Beckman Coulter (www (dot) beckman (dot) com). Luminex 100™ and Luminex HTS™ systems (which use microfluidics to align the microspheres and two lasers to excite the microspheres and the label) are available from Luminex Corporation (www (dot) luminex-corp (dot) com); the similar Bio-Plex™ Protein Array System is available from Bio-Rad Laboratories, Inc. (www (dot) bio-rad (dot) com). A confocal microplate reader suitable for microsphere analysis, the FMAT™ System 8100, is available from Applied Biosystems (www (dot) appliedbiosystems (dot) com).

As another example of particles that can be adapted for use in the present invention, sets of cylindrical glass microbeads that include optical barcodes are available from Illumina, Inc. (www (dot) illumina (dot) com, as VeraCode™). The optical barcodes are holographically inscribed digital codes that diffract a laser beam incident on the particles, producing an optical signature unique for each set of microbeads. A reader (the BeadXpress™ Reader) designed to identify and analyze the beads is also commercially available from Illumina, Inc. As yet another example of particles suitable for adaptation for use in the present invention, Digital Magnetic Beads™, paramagnetic particles with highly multiplexed barcodes (up to 5,000 distinguishable beads), are available from Maxwell Sensors, Inc. (www (dot) maxwellsensors (dot) com) These digital beads can be decoded by image processing or by a digital readout system including a microfluidic transducer, a bar-code reader and fluorescence detection.

Particles useful in the various methods, compositions, kits, and systems of the invention thus include, but are not limited to, microspheres, microbeads (e.g., non-spherical particles with a dimension similar to that of microspheres), and other beads or particles of regular or irregular shape (e.g., of similar dimension to microspheres, or optionally larger, e.g., up to 5 mm, 10 mm, or even larger), distinguishable by identifying characteristic(s). The particles optionally have additional or other desirable characteristics. For example, the particles can be magnetic or paramagnetic, providing a convenient means for separating the particles from solution, e.g., to simplify separation of the particles from any materials not bound to the particles.

Molecular Biological Techniques

In practicing the present invention, many conventional techniques in molecular biology, microbiology, and recombinant DNA technology are optionally used. These techniques are well known and are explained in, for example, Berger and Kimmel, Guide to Molecular Cloning Techniques, Methods in Enzymology volume 152 Academic Press, Inc., San Diego, Calif., Sambrook et al., Molecular Cloning—A Laboratory Manual (3rd Ed.), Vol. 1-3, Cold Spring Harbor Laboratory, Cold Spring Harbor, N.Y., 2000, and Current Protocols in Molecular Biology, F. M. Ausubel et al., eds., Current Protocols, a joint venture between Greene Publishing Associates, Inc. and John Wiley & Sons, Inc., (supplemented through 2008). Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla.

Making Polynucleotides

Methods of making nucleic acids (e.g., by in vitro amplification, purification from cells, or chemical synthesis), methods for manipulating nucleic acids (e.g., by restriction enzyme digestion, ligation, etc.) and various vectors, cell lines and the like useful in manipulating and making nucleic acids are described in the above references. In addition, methods of making branched polynucleotides (e.g., amplification multimers) are described in U.S. Pat. No. 5,635,352, U.S. Pat. No. 5,124,246, U.S. Pat. No. 5,710,264, and U.S. Pat. No. 5,849,481, as well as in other references mentioned above.

In addition, essentially any polynucleotide (including, e.g., labeled or biotinylated polynucleotides) can be custom or standard ordered from any of a variety of commercial sources, such as The Midland Certified Reagent Company (www (dot) mcrc (dot) com), The Great American Gene Company (www (dot) genco (dot) com), ExpressGen Inc. (www (dot) express-gen (dot) com), Qiagen (oligos (dot) qiagen (dot) com) and many others.

A label, biotin, or other moiety can optionally be introduced to a polynucleotide, either during or after synthesis. For example, a biotin phosphoramidite can be incorporated during chemical synthesis of a polynucleotide. Alternatively, any nucleic acid can be biotinylated using techniques known in the art; suitable reagents are commercially available, e.g., from Pierce Biotechnology (www (dot) piercenet (dot) com). Similarly, any nucleic acid can be fluorescently labeled, for example, by using commercially available kits such as those from Invitrogen Corp. (probes (dot) invitrogen (dot) com) or Pierce Biotechnology (www (dot) piercenet (dot) com) or by incorporating a fluorescently labeled phosphoramidite during chemical synthesis of a polynucleotide.

Aptamers

An aptamer is a nucleic acid capable of interacting with a binding partner, such as a protein, peptide or nucleic acid. Interaction with a nucleic acid ligand includes interactions other than complementary base pairing along the length of the aptamer and the nucleic acid ligand. An aptamer can be, e.g., a DNA or RNA, and can be, e.g., a chemically synthesized oligonucleotide. Aptamers can be selected, designed, etc. for binding various molecules by methods known in the art. For example, aptamers are reviewed in Sun S. (2000) "Technology evaluation: SELEX, Gilead Sciences Inc." Curr Opin Mol. Ther. 2: 100-5; Patel D J, Suri A K. (2000) "Structure, recognition and discrimination in RNA aptamer complexes with cofactors, amino acids, drugs and aminoglycoside antibiotics" J. Biotechnol. 74:39-60; Brody E N, Gold L. (2000) "Aptamers as therapeutic and diagnostic agents" J. Biotechnol. 74:5-13; Hermann T, Patel D J. (2000) "Adaptive recognition by nucleic acid aptamers" Science 287:820-5; Jayasena S D. (1999) "Aptamers: an emerging class of molecules that rival antibodies in diagnostics" Clin Chem. 45:1628-50; and Famulok M, Mayer G. (1999) "Aptamers as tools in molecular biology and immunology" Curr Top Microbiol Immunol. 243:123-36.

Making Polypeptides

Polypeptides (e.g., for use as capture or detection reagents, or for use in raising antibodies) can be obtained by any of a variety of methods known in the art. For example, smaller peptides (e.g., less than 50 amino acids long) are conveniently synthesized by standard chemical techniques and can optionally be chemically or enzymatically ligated to form larger polypeptides. Peptides (including, e.g., fluorescently labeled or biotinylated peptides) can also be custom ordered from a variety of commercial sources, including Biopeptide Co., LLC (www (dot) peptide-synthesis (dot) com), QIAGEN, Inc. (www (dot) merlincustomservices (dot) com) and Research Genetics (www (dot) resgen (dot) com). As another example, RNA encoding the polypeptide can be chemically synthesized (see, e.g., Oligonucleotide Synthesis (1984) Gait ed., IRL Press, Oxford). As yet another example, polypeptides can be purified from biological sources by methods well known in the art; polypeptides can be purified from a natural source or can optionally be produced in their naturally occurring, truncated, or fusion protein forms by recombinant DNA technology using techniques well known in the art (e.g., in vitro recombinant DNA techniques, synthetic techniques and in vivo genetic recombination), e.g., as described in the references above.

In brief, a polypeptide (e.g., a protein, a protein domain, a fusion protein) can be expressed in and purified from a suitable host cell. Expression occurs by placing a nucleotide sequence encoding the polypeptide into an appropriate expression vector, introducing the resulting expression vector into a suitable host cell and culturing the transformed host cell under conditions suitable for expression of the polypeptide; the recombinant polypeptide can then be purified from the host cell. Appropriate expression vectors are known in the art. For example, pET-14b, pcDNA1Amp, and pVL1392 are available from Novagen (www (dot) novagen (dot) com) and Invitrogen (www (dot) invitrogen (dot) com) and are suitable vectors for expression in *E. coli*, COS cells and baculovirus-infected insect cells, respectively. These vectors are illustrative of those that are known in the art. Suitable host cells can be any cell capable of growth in a suitable media and allowing purification of the expressed protein. Examples of suitable host cells include bacterial cells, such as *E. coli, Streptococci, Staphylococci, Streptomyces* and *Bacillus subtilis* cells; fungal cells such as yeast cells, e.g., *Saccharomyces* or *Pichia*, and *Aspergillus* cells; insect cells such as *Drosophila* S2 and *Spodoptera* Sf9 cells, mammalian cells such as CHO, COS, HeLa; and plant cells. Culturing and growth of the transformed host cells can occur under conditions that are known in the art (see, e.g., the references previously noted). The conditions (e.g., temperature and chemicals) will generally depend upon the host cell and the type of vector and promoter used.

Purification of the polypeptide can be accomplished using standard procedures known to and used by those of skill in the art. Generally, the transformed cells expressing the polypeptide are broken and crude purification is performed to remove debris and some contaminating proteins, followed by further purification (e.g., by chromatography) to the desired level of purity. Cells can be broken by known techniques such as homogenization, sonication, detergent lysis and freeze-thaw techniques. The polypeptide can be recovered and purified (partially or substantially to homogeneity) by any of a number of methods well known in the art, including, e.g., ammonium sulfate or ethanol precipitation, centrifugation, acid or base extraction, column chromatography, affinity column chromatography, anion or cation exchange chromatography, phosphocellulose chromatography, high performance liquid chromatography (HPLC), gel filtration, hydrophobic interaction chromatography, hydroxylapatite chromatography, lectin chromatography, gel electrophoresis and the like.

In addition to other references noted herein, a variety of protein purification methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2nd Edition Wiley-Liss, NY; Walker (1996) The Protein Protocols Handbook Humana Press, NJ; Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein.

Well known techniques for refolding proteins can be used if necessary to obtain the active conformation of the protein when the protein is denatured during intracellular synthesis, isolation or purification. Methods of reducing, denaturing and renaturing proteins are well known to those of skill in the art (see the references above and Debinski, et al. (1993) J. Biol. Chem., 268: 14065-14070; Kreitman and Pastan (1993) Bioconjug. Chem., 4: 581-585; and Buchner, et al. (1992) Anal. Biochem., 205: 263-270).

The nucleotide sequence encoding the polypeptide can optionally be fused in-frame to a sequence encoding a module (e.g., a domain or tag) that facilitates purification of the polypeptide and/or facilitates association of the fusion polypeptide with a particle or another reagent. Such modules include, but are not limited to, metal chelating peptides such as histidine-tryptophan modules that allow purification on and/or binding to immobilized metals (e.g., a hexahistidine tag), a sequence which binds glutathione (e.g., GST), a hemagglutinin (HA) tag (corresponding to an epitope derived from the influenza hemagglutinin protein; Wilson, I., et al. (1984) Cell 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the sequence of the invention is useful to facilitate purification.

Any polypeptide can optionally be labeled, biotinylated or coupled with another moiety, either during or after synthesis. For example, a polypeptide can be fluorescently labeled using a commercially available kit, e.g., from Invitrogen Corp. (probes (dot) invitrogen (dot) com) or Pierce Biotechnology (www (dot) piercenet (dot) com). Similarly, a polypeptide can be biotinylated using commercially available kits or reagents, e.g., from Pierce Biotechnology (www (dot) piercenet (dot) com).

Production and Labeling of Antibodies

For the production of antibodies to a particular protein (e.g., for use as a capture and/or detection reagent for that protein), various host animals may be immunized by injection with the polypeptide or a portion thereof (or other immunogenic analyte of interest). Such host animals include, but are not limited to, rabbits, mice and rats, to name but a few. Various adjuvants may be used to enhance the immunological response, depending on the host species; adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a protein or an antigenic functional derivative thereof. For the production of polyclonal antibodies, host animals, such as those described above, may be immunized by injection with the protein, or a portion thereof, supplemented with adjuvants as also described above. The protein can optionally be produced and purified as described herein. For example, recombinant protein can be produced in a host cell, or a synthetic peptide derived from the sequence of the protein can be conjugated to a carrier protein and used as an immunogen. Standard immunization protocols are described in, e.g., Harlow and Lane (1988) Antibodies, A Laboratory Manual, Cold Spring Harbor Publications, New York. Additional references and discussion of antibodies is also found herein.

Monoclonal antibodies (mAbs), which are homogeneous populations of antibodies to a particular antigen, may be obtained by any technique which provides for the production of antibody molecules by continuous cell lines in culture. These include, but are not limited to, the hybridoma technique of Kohler and Milstein (Nature 256:495-497, 1975; and U.S. Pat. No. 4,376,110), the human B-cell hybridoma technique (Kosbor et al. (1983) Immunology Today 4:72; Cole et al. (1983) Proc. Natl. Acad. Sci. USA 80:2026-2030), and the EBV-hybridoma technique (Cole et al. (1985) Monoclonal Antibodies and Cancer Therapy, Alan R. Liss, Inc., pp. 77-96). Such antibodies may be of any immunoglobulin class, including IgG, IgM, IgE, IgA, IgD, and any subclass thereof. The hybridoma producing the mAb of this invention may be cultivated in vitro or in vivo.

In addition, techniques developed for the production of "chimeric antibodies" (Morrison et al. (1984) Proc. Natl. Acad. Sci. USA 81:6851-6855; Neuberger et al. (1984) Nature 312:604-608; Takeda et al. (1985) Nature 314:452-454) by splicing the genes from a mouse antibody molecule of appropriate antigen specificity together with genes from a human antibody molecule of appropriate biological activity, can be used. A chimeric antibody is a molecule in which different portions are derived from different animal species, such as those having a variable or hypervariable region derived from a murine mAb and a human immunoglobulin constant region.

Similarly, techniques useful for the production of "humanized antibodies" can be adapted to produce antibodies to the proteins, fragments or derivatives thereof. Such techniques are disclosed in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429.

In addition, techniques described for the production of single-chain antibodies (U.S. Pat. No. 4,946,778; Bird (1988) Science 242:423-426; Huston et al. (1988) Proc. Natl. Acad. Sci. USA 85:5879-5883; and Ward et al. (1989) Nature 334:544-546) can be used. Single chain antibodies are formed by linking the heavy and light chain fragments of the Fv region via an amino acid bridge, resulting in a single-chain polypeptide.

Antibody fragments which recognize specific epitopes may be generated by known techniques. For example, such fragments include, but are not limited to, the $F(ab')_2$ fragments, which can be produced by pepsin digestion of the antibody molecule, and the Fab fragments, which can be generated by reducing the disulfide bridges of the $F(ab')_2$ fragments. Alternatively, Fab expression libraries may be constructed (Huse et al. (1989) Science 246:1275-1281) to allow rapid and easy identification of monoclonal Fab fragments with the desired specificity.

A large number of antibodies are commercially available. For example, monoclonal and/or polyclonal antibodies against any of a large number of specific proteins, against phosphoserine, against phosphothreonine, against phosphotyrosine, and against any phosphoprotein (i.e., against phosphoserine, phosphothreonine and phosphotyrosine) are available, for example, from Zymed Laboratories, Inc. (www (dot) zymed (dot) com), QIAGEN, Inc. (www (dot) qiagen (dot) com) and BD Biosciences (www (dot) bd (dot) com), among many other sources. In addition, a number of companies offer services that produce antibodies against the desired antigen (e.g., a protein supplied by the customer or a peptide synthesized to order), including Abgent (www (dot) abgent (dot) com), QIAGEN, Inc. (www (dot) merlincustomservices (dot) com) and Zymed Laboratories, Inc. (www (dot) zymed (dot) com).

Optionally, a fluorescent label (e.g., a fluorophore such as fluorescein, Alexa Fluor 488, phycoerythrin or rhodamine) can be chemically coupled to antibodies without altering their binding capacity (e.g., by use of a commercially available kit for labeling antibodies, such as the kits available from Invitrogen Corp. (probes (dot) invitrogen (dot) com) and Pierce Biotechnology (www (dot) piercenet (dot) com)). When activated by illumination with light of a particular wavelength, the fluorescent label on the antibody absorbs the light energy, inducing a state of excitability in the molecule, followed by emission of the light at a characteristic longer wavelength. The emission appears as a characteristic color visually detectable with a light microscope, flow cytometer or other suitable instrument. Such techniques are very well established in the art. Similarly, other moieties such as enzymes, gold particles, biotin, etc. can be coupled to antibodies. For example, kits and reagents for biotinylating antibodies (e.g., for subsequent detection of the biotinylated antibody with fluorescently labeled avidin or streptavidin) are commercially available, e.g., from Pierce Biotechnology (www (dot) piercenet (dot) com). Alternatively, one or more antibodies of a given species can be detected with a labeled anti-species antibody (e.g., mouse antibodies can be detected with a goat anti-mouse antibody).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

4×4 Multiplex bDNA assay

The following sets forth a series of experiments that demonstrate detection of four mRNAs from cell lysate in a bDNA assay using from one to four microsphere populations (or panels) having four distinguishable microsphere subsets each. Panel 1, for example, includes four different sets of fluorescently color-coded beads (Luminex Corp.), each with a different polynucleotide capture probe. Each target mRNA (PPIB, GAPDH, MET, and HEY-1) is thus captured to a different subset of beads. Panels 2, 3, and 4 each contain four different subsets of beads (for a total of 16 distinguishable bead subsets in Panels 1-4), but each panel contains capture probe oligos that are the same as those of Panel 1. Each panel (population) of beads is used to capture target nucleic acids. The panels are then combined in various combinations and processed as outlined above for bDNA assays (see, e.g., FIG. 4 Panels A and D).

Figure 7:
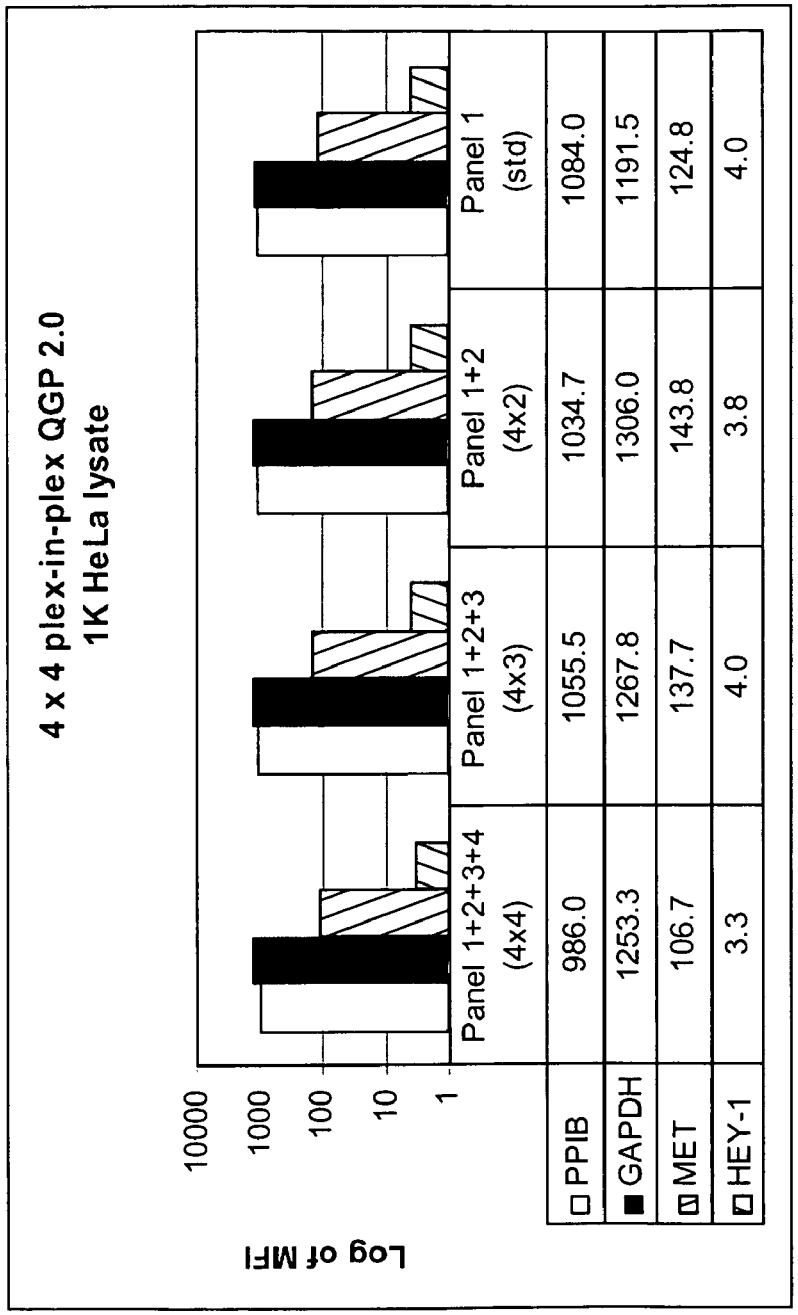
FIG. 7 presents a bar graph comparing results of multiplex assays for four mRNAs in HeLa cell lysates.

As shown in FIG. 7, quantitation of the four nucleic acid targets from HeLa cell lysate by detecting the beads in Panel 1 produced essentially the same results whether Panel 1 was processed and read alone or in combination with Panel 2, Panels 2 and 3, or Panels 2, 3, and 4. HeLa lysates (1000 cells) were added into each well of a 96-well plate containing bead panel 1, 2, 3, or 4 and the corresponding 4-plex probe set (CEs, LEs, and BPs for GAPDH, PPIB, MET, and HEY-1). Each panel contains four different color coded beads. Each panel, however, contains the same four zip code capture probe oligos (one capture probe on each of the four different beads in the panel). After overnight incubation, the plate containing panel 1 was processed as for a conventional bDNA assay as outlined in FIG. 4 Panel A or mixed with plates containing panel 2, panels 2 and 3, or panels 2, 3, and 4 and processed as described in the workflow illustrated in FIG. 4 Panel D. Results for each of the four target mRNAs captured on the beads of panel 1 are comparable regardless of whether the panel was processed separately or processed after combination with the other panels.

Figure 8:
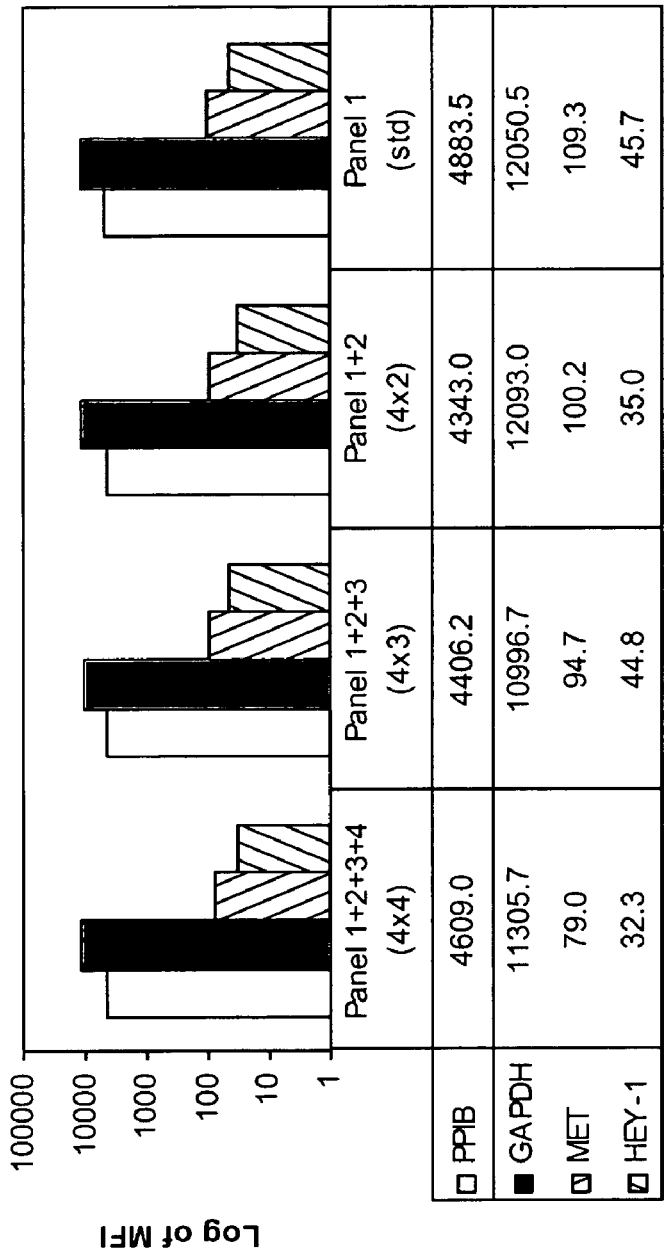
FIG. 8 presents a bar graph comparing results of multiplex assays for four mRNAs in U2OS cell lysates.

Detection from U2OS lysate yielded similar results, as shown in FIG. 8. U2OS lysates (8000 cells) were added into each well of a 96-well plate containing bead panel 1, 2, 3, or 4 and the corresponding 4-plex probe set (CEs, LEs, and BPs for GAPDH, PPIB, MET, and HEY-1). Again, each panel contains four different color coded beads, and the same four zip code capture probe oligos. After overnight incubation, the plate containing panel 1 was processed as for a conventional bDNA assay as outlined in FIG. 4 Panel A or mixed with plates containing panel 2, panels 2 and 3, or panels 2, 3, and 4 and processed as described in the workflow illustrated in FIG. 4 Panel D. Results for each of the four target mRNAs captured on the beads of panel 1 are comparable regardless of whether the panel was processed separately or processed after combination with the other panels.

Example 2

8×8 Multiplex bDNA assay

The following demonstrates detection of eight RNAs in a multiplex assay using eight microsphere populations having eight distinguishable microsphere subsets each. 40,000 copies of in vitro transcribed RNAs (RELA, UGT1A9, ABCC2, CSF2, IL-1b, GAPD, PPIB and bACT) were added to each well of a 384 well plate containing bead panel 1, 2, 3, 4, 5, 6, 7 or 8 and containing the corresponding 8-plex probe set (CEs, LEs, and BPs for the eight target RNAs). Each panel contains eight different color coded beads (for a total of 64 different distinguishable bead subsets in panels 1-8). However, each panel contains the same eight zip code oligos on the beads, as illustrated in FIG. 4 Panel B. After overnight incubation, all eight panels were combined into a single plate and processed according to the workflow illustrated in FIG. 4 Panel D, except that magnetic separation instead of filter separation was employed. (Magnetic beads were employed to facilitate handling.)

Figure 9:
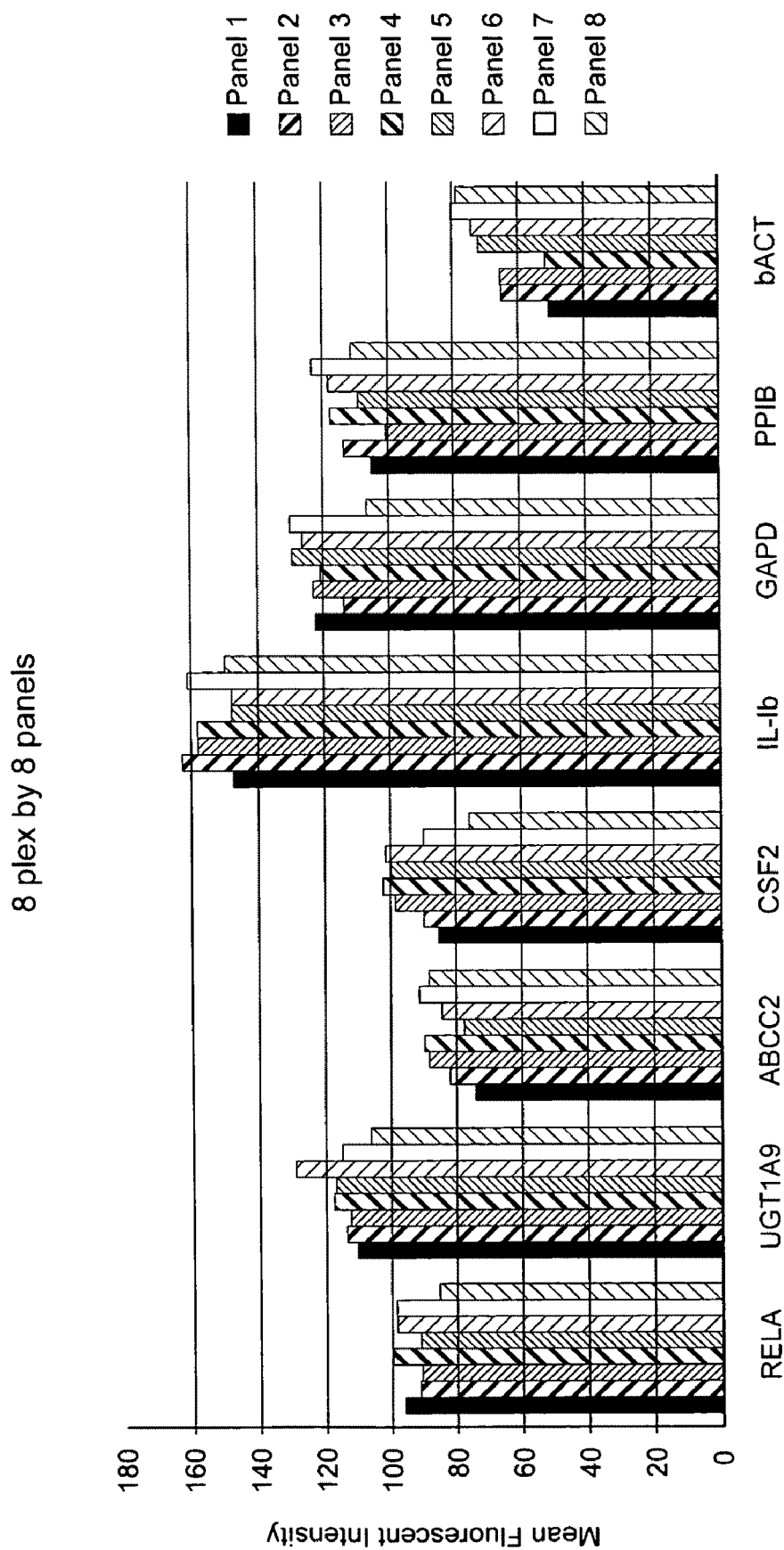
FIG. 9 presents a bar graph comparing results for eight different RNAs across eight panels of beads in a multiplex assay.

As shown in FIG. 9 and Table 1, the results observed for each of the eight target RNAs are reproducible across all eight different populations of beads. Read times, reagent usage, etc. are thus decreased without sacrificing accuracy. Furthermore, since the later processing steps for the beads across the eight panels are performed in the same wells, the inter-panel precision (indicated by the CV) is improved relative to that typically observed for samples processed in different wells.

TABLE 1

| Mean fluorescent intensities for the 8 × 8 assay. | | | | | | | | |
|---|---|---|---|---|---|---|---|---|
| | RELA | UGT1A9 | ABCC2 | CSF2 | IL-Ib | GAPD | PPIB | bACT |
| Panel 1 | 96 | 111 | 74 | 85 | 147 | 123 | 106 | 51 |
| Panel 2 | 91 | 114 | 83 | 90 | 163 | 114 | 114 | 65 |
| Panel 3 | 91 | 113 | 88 | 98 | 158 | 123 | 101 | 66 |
| Panel 4 | 100 | 118 | 90 | 103 | 159 | 121 | 118 | 52 |
| Panel 5 | 91 | 117 | 78 | 100 | 148 | 129 | 109 | 72 |
| Panel 6 | 98 | 129 | 84 | 102 | 148 | 127 | 119 | 74 |
| Panel 7 | 98 | 116 | 91 | 90 | 161 | 130 | 124 | 81 |
| Panel 8 | 86 | 106 | 88 | 76 | 150 | 107 | 112 | 80 |
| Ave[a] | 94 | 116 | 85 | 93 | 154 | 122 | 113 | 68 |
| STDEV[b] | 5.0 | 6.7 | 6.0 | 9.4 | 6.5 | 7.9 | 7.5 | 11.5 |
| CV[c] | 5% | 6% | 7% | 10% | 4% | 6% | 7% | 17% |

[a]Ave: Average of panels 1-8
[b]STDEV: standard deviation
[c]CV: coefficient of variation While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A multiplex analyte detection method, which comprises:
   providing a first sample comprising or putatively comprising a first group of one or more analytes;

providing a second sample comprising or putatively comprising a second group of one or more analytes;

providing a first population of particles comprising one or more subsets of particles, wherein:

each subset of the one or more subsets of particles in the first population comprises a capture molecule that specifically binds to one of the analytes of the first group or to a molecule that in turn binds to the analyte, which capture molecule is different than that on all other subsets of particles in the first population, wherein a different capture molecule and subset of particles is provided for each different analyte in the first group, and a plurality of particles in each subset of the one or more subsets of particles in the first population are distinguishable from a plurality of particles in every other subset of particles in the first population;

providing a second population of particles comprising one or more subsets of particles, wherein:

each subset of the one or more subsets of particles in the second population comprises a capture molecule that specifically binds to one of the analytes of the second group or to a molecule that in turn binds to the analyte, which capture molecule is different than that on all other subsets of particles in the second population, wherein a different capture molecule and subset of particles is provided for each different analyte in the second group, and a plurality of particles in each subset of the one or more subsets of particles in the second population are distinguishable from a plurality of particles in every other subset of particles in the second population and from a plurality of particles in every subset of the first population;

contacting in a first container the first sample and the first population of particles, thereby binding those analytes of the first group that were present in the first sample to the first population of particles;

contacting in a second container the second sample and the second population of particles, thereby binding those analytes of the second group that were present in the second sample to the second population of particles;

combining the first and second populations of particles after contacting them with the samples; and after combining the first and second populations of particles, detecting which subsets of particles have an analyte captured on the particles, thereby indicating which analytes were present in the samples, by:

providing a detection reagent comprising a label, contacting the detection reagent with the combined populations of particles, whereby the detection reagent binds directly or indirectly to the analytes captured on the particles, and identifying at least a portion of the particles from each of the subsets of particles in each of the populations of particles and detecting the presence or absence of the label on those particles, wherein presence of the label on the subset of particles comprising the capture molecule for a particular analyte indicates that that analyte is captured on those particles and therefore indicates that that analyte was present in the sample with which those particles were contacted, thereby detecting multiple analytes.

2. The method according to claim 1, wherein the first sample comprises or putatively comprises a first group of two or more analytes, the second sample comprises or putatively comprises a second group of two or more analytes, the first population of particles comprises two or more subsets of particles, and the second population of particles comprises two or more subsets of particles.

3. The method according to claim 1, wherein the capture molecules on the subsets of the first population of particles are the same as the capture molecules on the subsets of the second population of particles.

4. The method according to claim 1, wherein the analytes are polypeptides or nucleic acids.

5. The method according to claim 1, wherein the analytes of the first group and the analytes of the second group are the same group of target molecules derived from different sources.

6. The method according to claim 1, wherein the detection reagent is a labeled antibody, a labeled polynucleotide, a labeled avidin or a labeled streptavidin.

7. The method according to claim 1, wherein the capture molecules on the first and/or second populations of particles comprise antibodies or polynucleotides.

8. The method according to claim 1, wherein the one or more analytes are nucleic acids and the capture molecules are polynucleotide capture probes;

wherein the contacting steps comprise:

providing a number of subsets of capture extenders equivalent to the number of subsets of particles in the first and second populations of particles, each subset of capture extenders being configured to hybridize simultaneously to one of the analytes and to one of the capture probes, contacting the first sample with the corresponding one or more subsets of capture extenders and with the first population of particles, whereby the one or more analytes are bound to the one or more subsets of particles, and contacting the second sample with the corresponding one or more subsets of capture extenders and with the second population of particles, whereby the one or more analytes are bound to the one or more subsets of particles; and wherein detecting which subsets of particles have an analyte captured on the particles comprises:

hybridizing one or more label extenders and a label probe system comprising a label to the nucleic acid analytes captured on the particles, and identifying at least a portion of the particles from each of the subsets of particles in each of the populations of particles and detecting the presence or absence of the label on those particles, wherein presence of the label on the subset of particles comprising the capture molecule for a particular analyte indicates that that analyte is captured on those particles and therefore indicates that that analyte was present in the sample with which those particles were contacted, thereby detecting multiple analytes.

9. The method according to claim 1, wherein the one or more analytes are biotinylated nucleic acids;

wherein the capture molecules are polynucleotides, each of which is complementary to one of the nucleic acid analytes;

wherein providing a first sample comprising or putatively comprising a first group of one or more analytes comprises isolating a first group of one or more biotinylated nucleic acids bound by one or more transcription factors;

wherein providing a second sample comprising or putatively comprising a second group of one or more analytes comprises isolating a second group of one or more biotinylated nucleic acids bound by one or more transcription factors;

wherein binding those analytes of the first or second group that were present in the first or second sample to the first or second population of particles comprises hybridizing each of the biotinylated nucleic acid analytes present in the first or second sample to its complementary polynucleotide capture molecule;

wherein detecting which subsets of particles have an analyte captured on the particles comprises:
- binding labeled streptavidin or labeled avidin to the biotinylated nucleic acid analytes, and
- identifying at least a portion of the particles from each of the subsets of particles in each of the populations of particles and detecting the presence or absence of the label on those particles, wherein presence of the label on the subset of particles comprising the capture molecule for a particular analyte indicates that that analyte is captured on those particles and therefore indicates that that analyte was present in the sample with which those particles were contacted, thereby detecting multiple analytes.

10. The method according to claim 1, wherein the one or more analytes are tyrosine-phosphorylated polypeptides;

wherein the capture molecules comprise SH2 peptide domains; and wherein detecting which subsets of particles have an analyte captured on the particles comprises:
- contacting, and thereby binding, a biotinylated anti-phosphotyrosine antibody with the tyrosine-phosphorylated polypeptide analytes bound to the particles,
- contacting, and thereby binding, labeled streptavidin or labeled avidin to the biotinylated anti-phosphotyrosine antibody, and
- identifying at least a portion of the particles from each of the subsets of particles in each of the populations of particles and detecting the presence or absence of the label on those particles, wherein presence of the label on the subset of particles comprising the capture molecule for a particular analyte indicates that that analyte is captured on those particles and therefore indicates that that analyte was present in the sample with which those particles were contacted, thereby detecting multiple analytes.

11. The method according to claim 1, further comprising:

providing a third sample comprising or putatively comprising a third group of one or more analytes;

providing a third population of particles comprising one or more subsets of particles, wherein,
- a plurality of particles in each subset of the one or more subsets of particles in the third population are distinguishable from a plurality of particles in every other subset of particles in the third population and from a plurality of particles in every subset of particles in the first and second populations; and
- each subset of the one or more subsets of particles in the third population comprises a capture molecule that specifically binds to one of the analytes in the third group or to a molecule that in turn binds to the analyte, which capture molecule is different than that on all other subsets of particles in the third population of particles, wherein a different capture molecule and subset of particles is provided for each different analyte in the third group;

wherein the contacting steps further comprise contacting the third sample and the third population of particles in a third container, thereby binding those analytes of the third group that were present in the third sample to the third population of particles;

wherein combining the first and second populations of particles comprises combining the first, second, and third populations of particles.

* * * * *